(12) United States Patent
Barnett et al.

(10) Patent No.: US 9,220,761 B2
(45) Date of Patent: Dec. 29, 2015

(54) ALGINATE AND ALGINATE LYASE COMPOSITIONS AND METHODS OF USE

(75) Inventors: Bradley P. Barnett, Baltimore, MD (US); Philippe Gailloud, Towson, MD (US)

(73) Assignee: The John Hopkins University, Baltimore, MD (US)

(*) Notice: Subject to any disclaimer, the term of this patent is extended or adjusted under 35 U.S.C. 154(b) by 1154 days.

(21) Appl. No.: 12/422,637

(22) Filed: Apr. 13, 2009

(65) Prior Publication Data

US 2010/0080788 A1    Apr. 1, 2010

Related U.S. Application Data

(63) Continuation of application No. PCT/US2007/021872, filed on Oct. 11, 2007.

(60) Provisional application No. 60/851,837, filed on Oct. 12, 2006, provisional application No. 60/936,230, filed on Jun. 19, 2007.

(51) Int. Cl.
| | |
|---|---|
| *C12N 9/88* | (2006.01) |
| *A61K 38/51* | (2006.01) |
| *A61K 38/18* | (2006.01) |
| *A61K 38/48* | (2006.01) |
| *A61K 45/06* | (2006.01) |
| *A61K 31/704* | (2006.01) |
| *A61L 27/20* | (2006.01) |
| *A61L 27/38* | (2006.01) |
| *A61L 27/54* | (2006.01) |

(52) U.S. Cl.
CPC .............. *A61K 38/51* (2013.01); *A61K 31/704* (2013.01); *A61K 38/1875* (2013.01); *A61K 38/4893* (2013.01); *A61K 45/06* (2013.01); *A61L 27/20* (2013.01); *A61L 27/3882* (2013.01); *A61L 27/54* (2013.01); *A61L 2300/254* (2013.01); *C12N 9/88* (2013.01)

(58) Field of Classification Search
CPC ................... C12N 9/88; A61K 8/042
USPC ........................................ 435/232; 424/94.1
See application file for complete search history.

(56) References Cited

U.S. PATENT DOCUMENTS

| | | | |
|---|---|---|---|
| 5,582,825 A * | 12/1996 | Sakaguchi et al. ........... | 424/94.5 |
| 2002/0159823 A1 | 10/2002 | Aday et al. | |
| 2002/0197605 A1 | 12/2002 | Nakagawa et al. | |
| 2005/0003503 A1 | 1/2005 | Manyak et al. | |
| 2005/0095428 A1 | 5/2005 | Dicarlo et al. | |
| 2005/0143286 A1 | 6/2005 | Singh et al. | |
| 2005/0165480 A1 | 7/2005 | Jordan et al. | |
| 2006/0159823 A1 | 7/2006 | Melvik et al. | |

FOREIGN PATENT DOCUMENTS

JP    63039589    2/1988

OTHER PUBLICATIONS

Schiller et al. Characterization of the *Pseudomonas aeruginosa* Alginate Lyase Gene (algL); Cloning, Sequencing, and Expression in *Escherichia coli*. J Bacteriol. 1993, vol. 175 (15), p. 4780-4789. Abstract; p. 4785, col. 1, last para; Table 1, and Fig 3.

Ivanova et al. *Pseudoalteromonas issachenkonii* sp. nov., a bacterium that degrades the thallus of a brown alga *Fucus evanescens*. Int J Syst Evol Microbiol. 2002 vol. 52(1), p. 229-234.

Sigma-Aldrich Corp. Retrieved frm the Internet: <URL http://www.enzymedirectory.com/moreinfo.php?id=3353&wc=1>    Other names: alginate lyase, alginase.

International Preliminary Report on Patentability issued in corresponding International Application No. PCT/US2007/021872, Mar. 3, 2009, 18 pages.

* cited by examiner

*Primary Examiner* — Ruth Davis
(74) *Attorney, Agent, or Firm* — Mintz Levin Cohn Ferris Glovsky and Popeo, P.C.; Peter F. Corless; Christopher R. Cowles

(57) ABSTRACT

The invention features alginate and alginate lyase compositions and methods that are useful for the treatment of various conditions and diseases. The invention also provides kits and instructions for use.

19 Claims, 21 Drawing Sheets

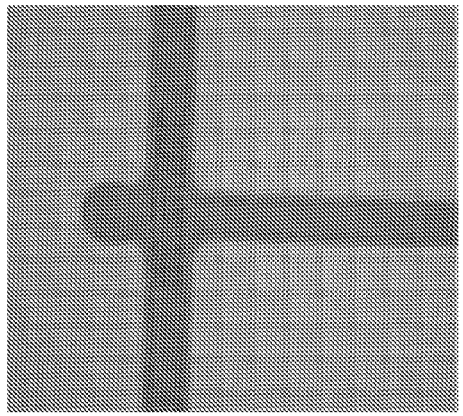 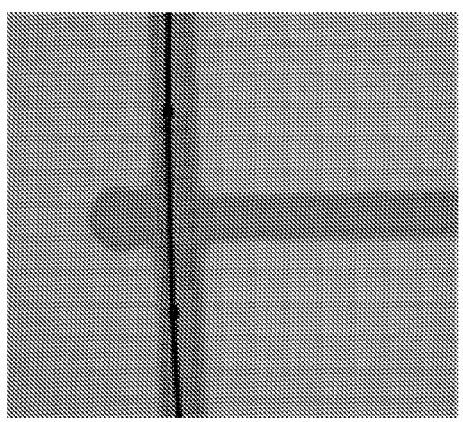 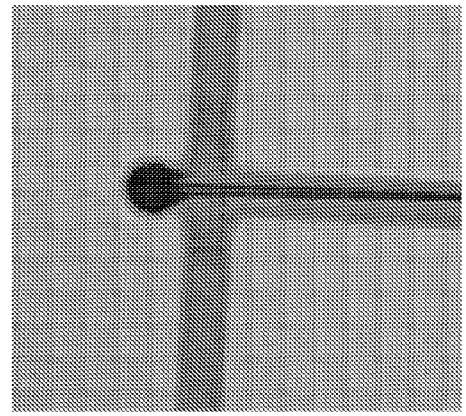 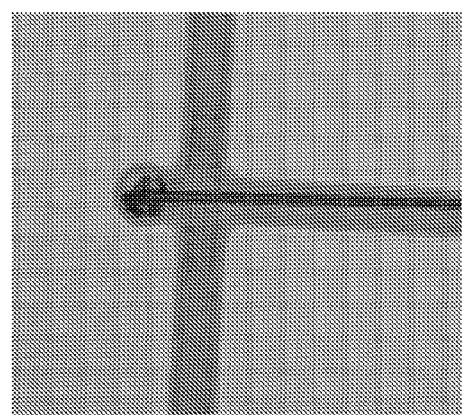 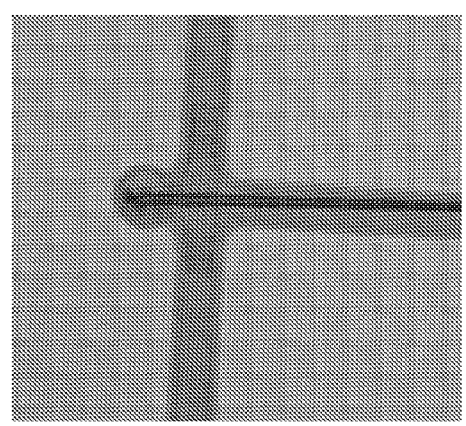
FIG. 1A  FIG. 1B  FIG. 1C  FIG. 1D  FIG. 1E  FIG. 1F

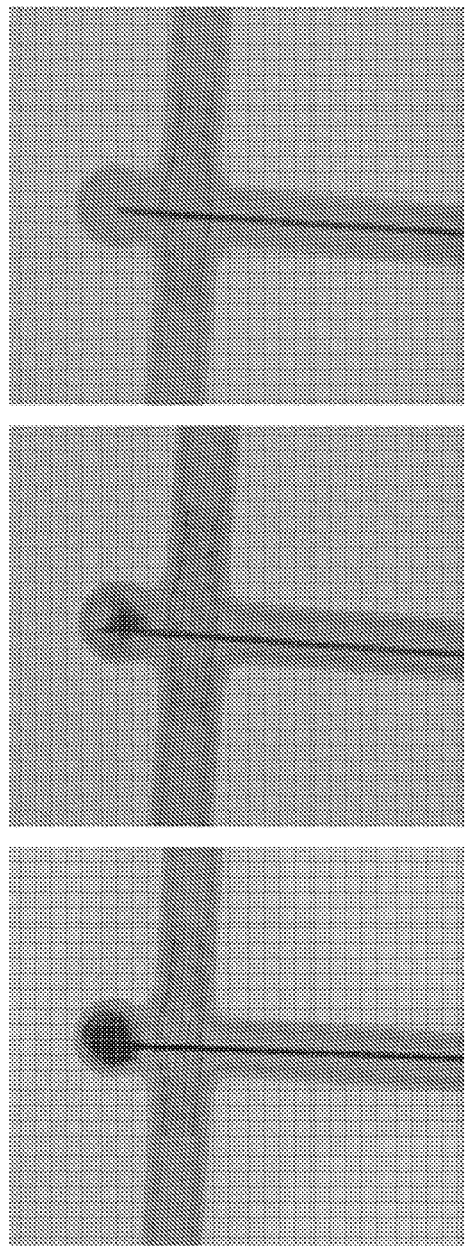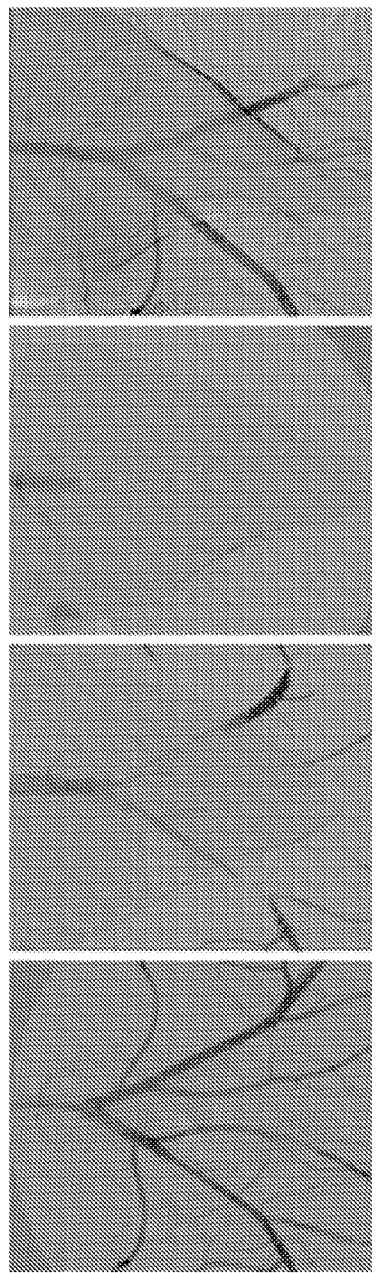

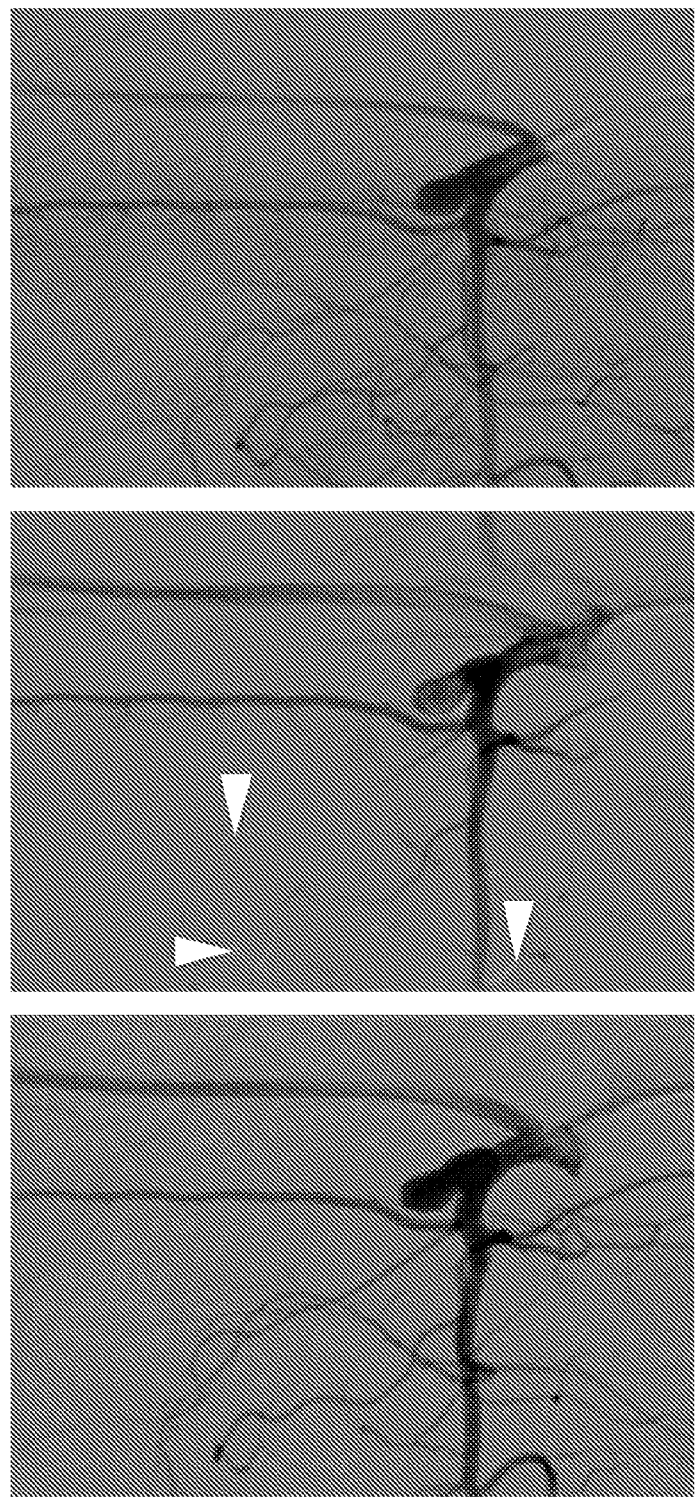

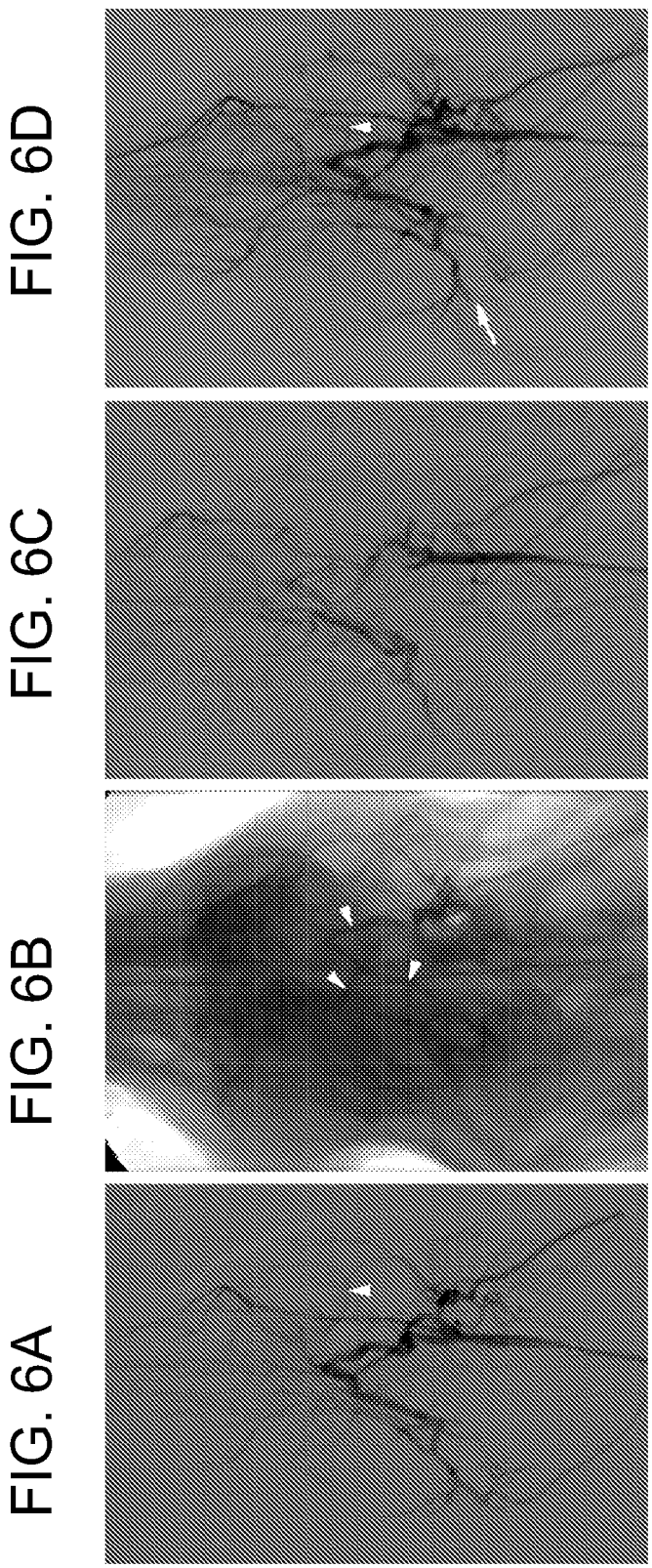

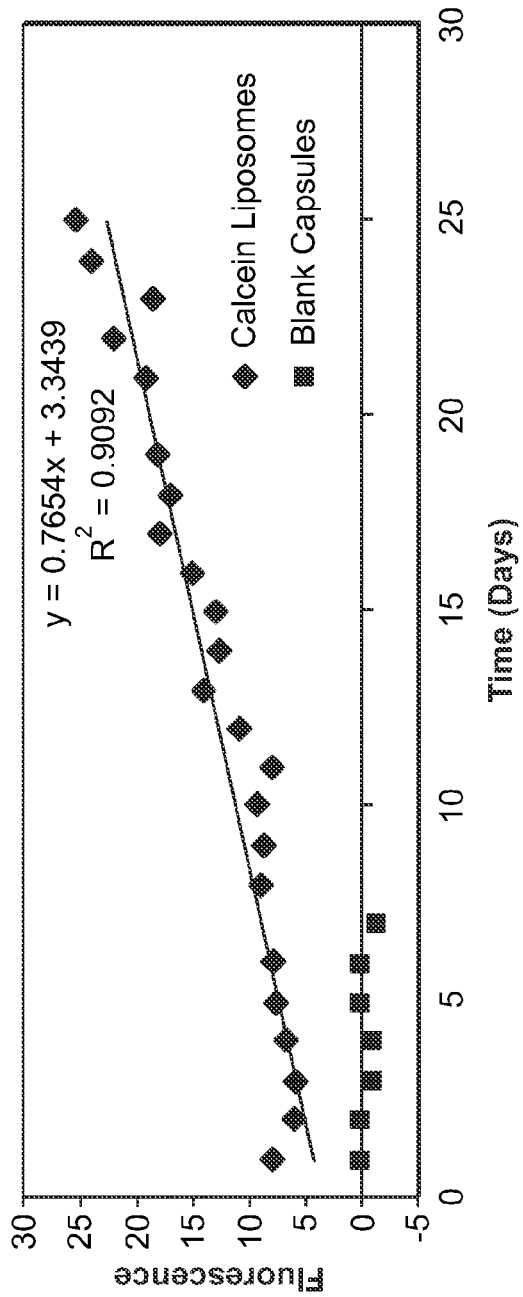

SEQ ID NO: 1 mktshliria lpgalaaall asqvsqaadl vpppgyyaav gerkgsagsc pavpppytgs lvftskyegs dsarathvk aektfrsqik ditdmergat klvtqymrsg rdgdlacaln wmsawaraga lqsddfnhtg ksmrkwalgs lsgaymrlkf sssrplaaha eqsreiedwf arlgtqvvrd wsglplkkin nhsywaawsv mstavvtnrr dlfdwavsef kvaanqvdeq gflpnelkrr qralayhnya lpplamiapf aqvngvdlrq enhgalqrla ervmkgvdde etfeektged qdmtdllkvdn kyawlepyca lyrcepnacs rpkkdrepfn sfrlggevtr vfsreggs

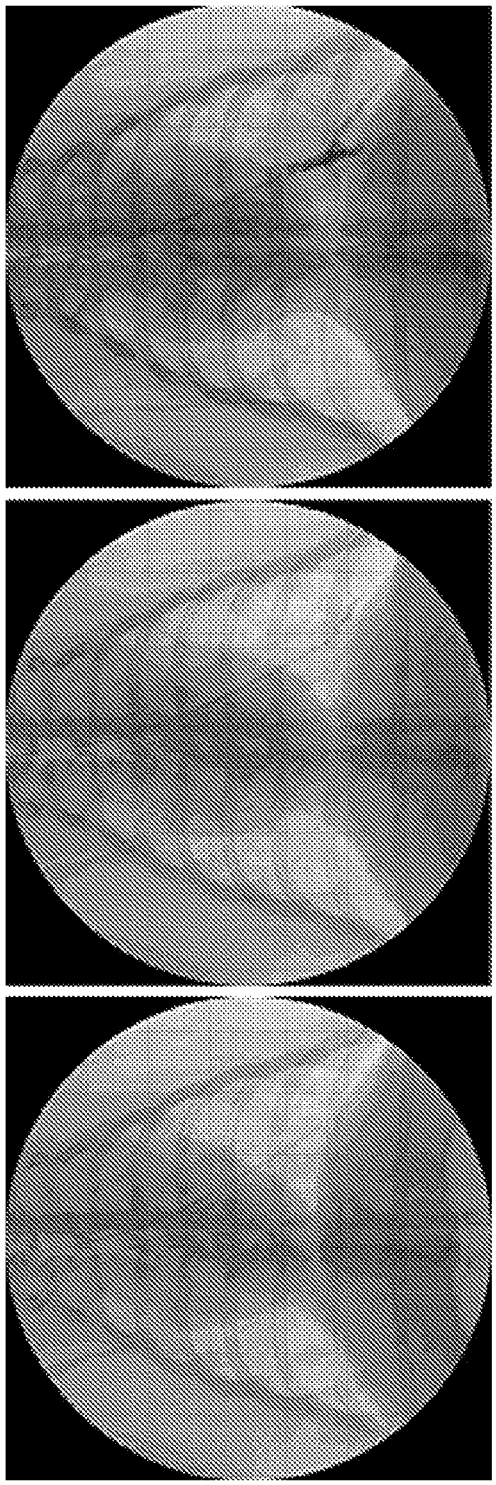

SEQUENCE LISTING

```
<160> NUMBER OF SEQ ID NOS: 1

<210> SEQ ID NO 1
<211> LENGTH: 368
<212> TYPE: PRT
<213> ORGANISM: Pseudomonas aeruginosa

<400> SEQUENCE: 1

Met Lys Thr Ser His Leu Ile Arg Ile Ala Leu Pro Gly Ala Leu Ala
1               5                   10                  15

Ala Ala Leu Leu Ala Ser Gln Val Ser Gln Ala Ala Asp Leu Val Pro
            20                  25                  30

Pro Pro Gly Tyr Tyr Ala Ala Val Gly Glu Arg Lys Gly Ser Ala Gly
        35                  40                  45

Ser Cys Pro Ala Val Pro Pro Pro Tyr Thr Gly Ser Leu Val Phe Thr
    50                  55                  60

Ser Lys Tyr Glu Gly Ser Asp Ser Ala Arg Ala Thr Leu Asn Val Lys
65                  70                  75                  80

Ala Glu Lys Thr Phe Arg Ser Gln Ile Lys Asp Ile Thr Asp Met Glu
                85                  90                  95

Arg Gly Ala Thr Lys Leu Val Thr Gln Tyr Met Arg Ser Gly Arg Asp
```

```
                    100                 105                 110
Gly Asp Leu Ala Cys Ala Leu Asn Trp Met Ser Ala Trp Ala Arg Ala
            115                 120                 125

Gly Ala Leu Gln Ser Asp Asp Phe Asn His Thr Gly Lys Ser Met Arg
            130                 135                 140

Lys Trp Ala Leu Gly Ser Leu Ser Gly Ala Tyr Met Arg Leu Lys Phe
145                 150                 155                 160

Ser Ser Ser Arg Pro Leu Ala Ala His Ala Glu Gln Ser Arg Glu Ile
            165                 170                 175

Glu Asp Trp Phe Ala Arg Leu Gly Thr Gln Val Val Arg Asp Trp Ser
            180                 185                 190

Gly Leu Pro Leu Lys Lys Ile Asn Asn His Ser Tyr Trp Ala Ala Trp
            195                 200                 205

Ser Val Met Ser Thr Ala Val Val Thr Asn Arg Arg Asp Leu Phe Asp
            210                 215                 220

Trp Ala Val Ser Glu Phe Lys Val Ala Ala Asn Gln Val Asp Glu Gln
225                 230                 235                 240

Gly Phe Leu Pro Asn Glu Leu Lys Arg Arg Gln Arg Ala Leu Ala Tyr
            245                 250                 255

His Asn Tyr Ala Leu Pro Pro Leu Ala Met Ile Ala Pro Phe Ala Gln
            260                 265                 270

Val Asn Gly Val Asp Leu Arg Gln Glu Asn His Gly Ala Leu Gln Arg
            275                 280                 285

Leu Ala Glu Arg Val Met Lys Gly Val Asp Asp Glu Glu Thr Phe Glu
            290                 295                 300

Glu Lys Thr Gly Glu Asp Gln Asp Met Thr Asp Leu Lys Val Asp Asn
305                 310                 315                 320

Lys Tyr Ala Trp Leu Glu Pro Tyr Cys Ala Leu Tyr Arg Cys Glu Pro
            325                 330                 335

Asn Ala Cys Ser Arg Pro Lys Lys Asp Arg Glu Pro Phe Asn Ser Phe
            340                 345                 350

Arg Leu Gly Gly Glu Val Thr Arg Val Phe Ser Arg Glu Gly Gly Ser
            355                 360                 365
```

ALGINATE AND ALGINATE LYASE COMPOSITIONS AND METHODS OF USE

RELATED APPLICATIONS

This application is a continuation of International Application Number PCT/US2007/021872 having an International Filing Date of Oct. 11, 2007, which claims priority to (1) U.S. provisional application No. 60/851,837 filed Oct. 12, 2006 and (2) U.S. provisional application No. 60/936,230 filed Jun. 19, 2007, all of which applications are incorporated by reference herein in their entirety.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or paragraphing priority from any of these applications and patents, and each of the documents cited or referenced in each of the application cited documents, are hereby expressly incorporated herein by reference. More generally, documents or references are cited in this text, either in a Reference List, or in the text itself; and, each of these documents or references ("herein-cited references"), as well as each document or reference cited in each of the herein-cited references (including any manufacturer's specifications, instructions, etc.), is hereby expressly incorporated herein by reference.

BACKGROUND OF THE INVENTION

Liquid or semi-liquid biomaterials that can be delivered in the human body, either by open surgical, direct percutaneous puncture, or remote endovascular access, constitute an important component of the modern therapeutic armentarium. Some of these agents, such as the acrylic bone cements, have been in clinical use for a long period of time, while others are currently reaching the last stages of preclinical development. The recent advent of minimally invasive vascular and non-vascular therapeutic techniques has given a new impetus for the development of such agents. The treatment of cerebral aneurysms with liquid embolic agents represents a good illustration of the potential advantages offered by these types of materials. However, there remain challenges that need to be addressed before clinical application may be recommended.

The goal of endovascular treatment of aneurysms is to obtain a complete and permanent exclusion of the aneurysmal sac from the arterial circulation, while preserving the patency of the parent vessel. Ideally, aneurysm thrombosis followed by endothelialization across the aneurysm orifice should be obtained. Detachable microcoils represent the currently accepted minimally invasive alternative to conventional surgical clipping for the treatment of cerebral aneurysms; however, even when an aneurysm filled with microcoils appears radiographically densely packed, typically less than half of the cavity volume is occupied by the microcoil mass. The remainder of the aneurysmal cavity is, in fact, filled with thrombus, which may or may not become organized.

Liquid embolic agents are emerging as promising alternatives to more homogeneous aneurysm filling, and the decreased recurrence rates seen; however, animal studies and preliminary human experience using various agents have revealed significant limitations inherent to the use of liquid embolic agents, including migration of the agent, parent artery occlusion, catheter adhesion, and cytotoxicity.

A potential alternative is alginate-based liquid embolic agents. Alginate is highly biocompatible, and its delivery and hardening can be controlled. However, complications may arise from the use of alginate. For instance, in some cases alginate hydrogel has been found to protrude out of the neck of the aneurysm and migrate into the parent artery during injection, a situation that carries a high risk of major complication such as vessel occlusion and stroke. Similar complications may result from the use of alginate in other therapeutic indications, such as in inadvertent obliteration of a normal cerebral artery during the embolization of a vascular malformation. Thus, there remains a need in the art for the development of agent(s) that can selectively dissolve alginate. Such a new agents would fill an urgent need in many different applications, such as embolization procedures, and cosmetic and reconstructive procedures. These agents would increase the safety of current therapy, and further provide potential use in a variety of clinical and experimental applications.

SUMMARY OF THE INVENTION

As described below, the present invention features alginate and alginate lyase based compositions and methods of use.

In one aspect, the invention provides a method for dissolving an alginate based biomaterial in a subject comprising the step of administering to the subject a composition comprising an alginate lyase.

In one embodiment, the composition comprising an alginate lyase further comprises a divalent metal chelator.

In another aspect, the invention provides a method for treating a subject suffering from a vascular or non-vascular condition, wherein the subject has previously received treatment with an alginate based biomaterial, the method comprising the step of administering to the subject a composition comprising an alginate lyase, thus treating the subject.

In one embodiment of the method, the vascular or non-vascular condition is selected from the group consisting of arteriovenous malformation, endovascular repair failure, osteoporosis, neurovascular lesions, telangiectasias, varicoceles, varicose veins, inflammatory lesions, hemorrhage, occlusion, embolism, neoplastic growth, venous disease, and phlebitis. In a further embodiment, the endovascular repair failure is endoleakage.

In another aspect, the invention provides a method for treating a subject suffering from a vascular or non-vascular occlusion, where the subject has previously received treatment with an alginate based biomaterial, the method comprising the step of administering to the subject a composition comprising an alginate lyase, thereby treating the subject.

In a particular embodiment of the method, the vascular occlusion is an embolism. In another embodiment, the vascular occlusion is a pulmonary embolism or an arterial embolism.

In yet another aspect, the invention provides a method for treating a subject suffering from a vascular or non-vascular hemorrhage, wherein the subject has previously received treatment with an alginate based biomaterial, the method comprising the step of administering to the subject a composition comprising an alginate lyase and a divalent metal chelator, and thereby treating the subject.

In one embodiment of the method, the hemorrhage is an intracranial hemorrhage.

In another aspect, the invention provides a method for treating a subject suffering from a neoplastic growth, wherein the subject has previously received treatment with an alginate based biomaterial for the neoplastic growth, the method comprising the step of administering to the subject a composition comprising alginate lyase, and thereby treating the subject.

In a particular embodiment of the method, the alginate based biomaterial comprises one or more anti-cancer agents. In another embodiment, the anti-cancer agent is selected from the group consisting of chemotherapeutics, antibodies, and biological agents. In a further embodiment of the method, the anti-cancer agent is selected from the group consisting of: abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvin-caleukoblastine, docetaxol, doxetaxel, cyclophosphamide, carboplatin, carmustine, cisplatin, cryptophycin, cyclophosphamide, cytarabine, dacarbazine, dactinomycin, daunorubicin, dolastatin, doxorubicin, etoposide, 5-fluorouracil, finasteride, flutamide, hydroxyurea and hydroxyureataxanes, ifosfamide, liarozole, lonidamine, lomustine, mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In another embodiment, the alginate based biomaterial further comprises iron oxides. In a further, embodiment, the iron oxides are conjugated with one or more antibodies.

In yet another embodiment, the method further comprises the step of exposing the subject to an alternating magnetic field.

In another aspect, the invention features a method for treating or preventing osteoporosis in a subject comprising the step of administering to the subject a composition comprising an alginate based biomaterial comprising an agent to a targeted area of osteoporotic bone, thereby treating or preventing osteoporosis in a subject. In one embodiment, the agent is an osteogenic agent. In another embodiment, the osteogenic agent is selected from the group consisting of: Wnt proteins, TGF-beta, basic fibroblast growth factor (bFGF), bone morphogenic protein-2 (BMP-2), osteonection and 1,25-dihydroxy vitamin D3 (1,25-OH D3). osteopontin, bone morphogenic proteins, Msc-2, bisphosphonates, tumor necrosis factor-alpha, oxysterols, osteoprotegerin, insulin like growth factor, high density lipoprotein, 1,25-dihydroxyvitamin D, transforming growth factor beta, estradiol, decorin and fetuin. In a further embodiment, the osteogenic agent is expressed by a cell transfected to overexpress one of the osteogenic agents listed above.

In another embodiment, the targeted area of osteoporotic bone is identified by computerized tomography or magnetic responance imaging. In still another further embodiment, the alginate based biomaterial comprising an agent in administered into the vertebrae of the subject.

In one aspect, the invention provides a method for the selective dissolution of an occlusion in a subject, wherein the subject has received treatment with an alginate based biomaterial, the method comprising the steps of administering to the subject an alginate based biomaterial to a targeted area, and then administering to the subject a composition comprising alginate lyase to the targeted area of the first step, and thereby providing selective dissolution of an occlusion in a subject.

In an embodiment of the method, the selective dissolution of an occlusion occurs in a vessel not targeted for treatment. In another embodiment of the method, administering to the subject the composition comprising alginate lyase occurs after occlusion. In another particular embodiment, administering the composition occurs 1 second to 1 week after occlusion. Thus, administration of the composition can occur at any time between 1 second, 5 seconds, 30 second, 60 seconds 5 minutes, 10 minutes, 30 minutes, 1 hour, 5 hours, 12 hours, 24 hours, 36 hours, 48 hours, 4 days, 5 days, 6 days, 7 days or more after occlusion.

In another aspect, the invention provides a method for the selective delivery of a therapeutic agent to a targeted non-occluded vessel, wherein the subject has received treatment with an alginate based biomaterial, the method comprising the steps of administering to the subject an alginate based biomaterial to a targeted area, and then administering a therapeutic agent to the targeted non-occluded vessel, and then administering to the subject a composition comprising alginate lyase to the targeted area of the first step, thereby providing selective delivery of therapeutic agent to a non-occluded vessel.

In a particular embodiment of the method, the therapeutic agent is any water-soluble therapeutic agent. In another embodiment, administering to the subject the composition comprising alginate lyase occurs after occlusion. In one embodiment of the method, administering the composition occurs 1 second to 1 week after occlusion. Thus, administration of the composition can occur at any time between 1 second, 5 seconds, 30 second, 60 seconds 5 minutes, 10 minutes, 30 minutes, 1 hour, 5 hours, 12 hours, 24 hours, 36 hours, 48 hours, 4 days, 5 days, 6 days, 7 days or more after occlusion.

In a particular aspect, the invention provides a method for the selective control of bulking or remodeling in a subject, the method comprising the steps of first administering to the subject an alginate based biomaterial to a targeted area, and then administering to the subject a composition comprising alginate lyase to the targeted area of the first step, wherein administration of the composition comprising alginate lyase and the divalent metal chelator provides selective control of bulking or remodeling in a subject.

In one embodiment of the method, the subject is undergoing plastic or reconstructive procedures.

In certain embodiments of the method, the target area is the lung.

In another aspect, the invention provides a method for lung volume reduction therapy in a subject, the method comprising the steps of administering to the subject an alginate based biomaterial to a targeted area, and administering to the subject a composition comprising alginate lyase to the targeted area of the first step, wherein administration of the composition comprising alginate lyase provides lung volume reduction therapy in a subject.

In another particular aspect, the invention provides a method for the controlled release of an agent in a subject, the method comprising the steps of first administering to the subject an alginate based biomaterial comprising an agent, and then administering to the subject a composition comprising alginate lyase, wherein administration of the composition comprising alginate lyase results in controlled release of the agent.

In one embodiment, the agent is a therapeutic agent. In another embodiment, the therapeutic agent is any water soluble agent. In another particular embodiment, the subject is suffering from a vascular or non-vascular condition. In a further embodiment, the therapeutic agent is a nanomaterial. In still a further embodiment, the therapeutic agent is contained within a nanomaterial. In another further embodiment, the therapeutic agent is bound to a nanomaterial.

In another particular embodiment of the method, the nanomaterial is selected from the group consisting of: microboxes, microchips, microfluidic pumps, magnetic resonance microcoil, quantum dots, antibody targeted nanomaterials, nanocontainers, and nanoboxes. In another particular embodiment, the therapeutic agent is contained within therapeutic liposomes. In another particular embodiment, the therapeutic liposomes are coated with protein. In another particular embodiment, the protein is selected from the group consisting of: antibodies, receptors, and cell surface markers.

In still another embodiment, the therapeutic agent is selected from the group consisting of: chemotherapeutic agents, anti-inflammatory agents, antimicrobial agents, hormonal therapy agents, metalloproteinase inhibitors, sclerosing agents, angio-active agents, plasmids for gene therapy, adenoviral vectors for gene therapy, RNAi, antisense, lentivirus, microbubbles, toxins, antibiotics, vaccines, photodynamic agents, and analgesics.

In still another particular embodiment, the therapeutic agent is further combined with a second agent selected from the group consisting of: contrast agents, quantum dots, antibodies, liposomes, and nanoboxes.

In another embodiment, the agent is a cell secreting a therapeutic factor. In another particular embodiment of the method, the cell secreting a therapeutic factor is selected from the group consisting of: autogenic or allogenic fibroblasts, endothelial cells, transgenic cells, mesenchymal stem cells, embryonic stem cells, extraembryonic stem cells, embryonic germ cells, cardiac stem cells, umbilical stem cells, cardiac stem cells, pluripotent and multipotent stem cells, pancreatic islet cells, hepatocytes, skin cells, intestinal stem cells, myoblasts, endothelial cells, cardiac myoblasts, dendritic cell, autologous tumor cells, monocyte derived activated killers, natural killer T cells, patients own cancer cells with liposomal Il-2, cultured chondrocytes, hematopoietic stem cells, sertoli cells, xenogenic cell sources of all listed above, skin cells, adipocytes, skin-derived stem cells, neural stem cells, glial progenitor cells, oligodendrocyte precursors, oligo precursors, fat stem cells, other stem cells sources such as from amniotic fluid, baby teeth, bone marrow cells, cord blood, placental blood, fat tissue, fetal cells, unfertilized ova, pancreas, and breast.

In another embodiment, the therapeutic agent is further combined with a second agent selected from the group consisting of contrast agents, quantum dots, antibodies, liposomes, and nanoboxes.

In yet another embodiment, the alginate based biomaterial linked to the agent is selected from the group consisting of: tissue scaffold, microcapsules or wound dressings.

In another aspect, the invention provides a method for the controlled release of a label in a subject, the method comprising the steps of administering to the subject an alginate based biomaterial comprising a label, and administering to the subject a composition comprising alginate lyase, wherein administration of the composition comprising alginate lyase results in controlled release of the label.

In one embodiment, the controlled release of the label is used for diagnostic purposes. In another embodiment, the diagnostic purpose is the selected angiography of a labeled vessel. In a particular embodiment of the method, the label is selected from the group consisting of a: radiolabel, fluorescent label, and a tissue dye. In a further embodiment, the label is contained within a micelle. In another embodiment, the radiolabel is selected from the group consisting of: carbon 14, carbon 14 intermediates, tritium-labeled radioisotopes, iodine 125 labeled radioisotopes, and antibody targeted radioisotopes. In a particular embodiment, the fluorescent label is selected from the group consisting of: cadmium selenide, quantum dots, fluorophores and their amine-reactive derivatives, thiol-reactive probes, reagents for modifying groups other than thiols or amines, biotin derivatives, haptens, crosslinking reagents, and photoactivatable reagents. In another embodiment, the tissue dye is methylene blue. In one embodiment, the label is contained within a liposome.

In another aspect, the invention features a method for the controlled release of a label in a subject, the method comprising the steps of administering to the subject an alginate based biomaterial comprising a label; and administering to the subject a composition comprising alginate lyase, wherein administration of the composition comprising alginate lyase results in controlled release of the label.

In one embodiment, the controlled release of the label is used for diagnostic purposes. In another embodiment, the diagnostic purpose is the selected angiography of a labeled vessel. In another embodiment, the label is selected from a radiolabel, fluorescent label, tissue dye. In another embodiment, the label is contained within a micelle.

In still a further embodiment, the radiolabel is selected from the group consisting of carbon 14, carbon 14 intermediates, tritium-labeled radioisotopes, iodine 125 labeled radioisotopes, and antibody targeted radioisotopes.

In another embodiment, the fluorescent label is selected from the group consisting of: cadmium selenide, quantum dots, fluorophores and their amine-reactive derivatives, thiol-reactive probes, reagents for modifying groups other than thiols or amines, biotin derivatives, haptens, crosslinking reagents, and photoactivatable reagents.

In one embodiment, the tissue dye is methylene blue.

In another embodiment, the label is contained within a liposome.

In a particular aspect, the invention provides a method for the controlled release of a label to mark lesions for radiosurgery, the method comprising the steps of administering to the subject an alginate based biomaterial linked to a label, and administering to the subject a composition comprising alginate lyase, wherein administration of the composition comprising alginate lyase results in controlled release of the label and marking of the lesion for radiosurgery.

In one embodiment of the method, the label is selected from the group consisting of a: radiolabel, fluorescent label, and tissue dye. In another embodiment, the label is contained within a micelle. In a particular embodiment, the radiolabel is selected from the group consisting of: carbon 14, carbon 14 intermediates, tritium-labeled radioisotopes, iodine 125 labeled radioisotopes, and antibody targeted radioisotopes. In another particular embodiment, the fluorescent label is selected from the group consisting of: cadmium selenide, quantum dots, fluorophores and their amine-reactive derivatives, thiol-reactive probes, reagents for modifying groups other than thiols or amines, biotin derivatives, haptens, crosslinking reagents, and photoactivatable reagents. In one embodiment, the tissue dye is methylene blue. In another embodiment, the label is contained within a liposome.

In another particular aspect, the invention provides a method for the controlled release of a contrast agent in a subject, the method comprising the steps of first administering to the subject an alginate based biomaterial comprising a contrast agent, and then administering to the subject a composition comprising alginate lyase, wherein administration of the composition comprising alginate lyase results in controlled release of the contrast agent.

In one embodiment of the method, the contrast agent is selected from the group consisting of: magnetic resonance contrast agents, radioopaque contrast agents, ultrasound contrast agents, and nuclear medicine imaging contrast agents.

In another aspect, the invention provides a method for the selective dissolution of a biocompatible material in a subject, the method comprising the steps of first administering to the subject an alginate loaded biocompatible material to a targeted area, and then administering to the subject a composition comprising alginate lyase to the targeted area of the first step, wherein administration of the composition comprising alginate lyase provides selective dissolution of the biocompatible material in the subject.

In one embodiment, a portion of the biocompatible material does not dissolve when treated with alginate lyase and a metal chelator. In another embodiment, the targeted area is selected from the group consisting of: liver, pancreas, thyroid, heart, peripheral nerve scaffold, breast, bladder, cartilage, bone, tendon, ligament, blood vessel, and spinal cord. In a particular embodiment, the biocompatible material is selected from the group consisting of: polyvinyl alcohol, sodium polyacrylate, acrylate polymers, Hyaluronase Polymers, collagen membrane, Porous HA/TCP ceramic composite, Hydroxyapatite bone cement, PVP/PMMA, tricalcium phosphate, Hydroxyapatite coated collagen fibres, calcium sulphate, Hydroxyapatite (HAp), Phosphorylcholine (PC), silicone, ultrahigh molecular weight polyethylene, polyethylene, acrylic, nylon, Polyurethane, Polypropylene, poly(methyl methacrylate), Teflon, Dacron, acetal, polyester, silicone-collagen composite, polyaledehyde, poly(vinyl chloride), silicone-acrylate, poly(tetrafluoroethylene), hydroxyethyl methacrylate (HEMA), poly(methyl methacrylate) (PMMA), poly(glycolide lactide), poly(glycolic acid), tetrafluoroethylene, hexafluoropropylene, poly(glycolic acid), poly(lactic acid), desaminotyrosyltyrosine ethyl ester, polydioxanone, fibrin, gelatin, hyaluronan, tricalcium phosphate, polyglycolide (PGA), polycaprolactone, poly (lactide-co-glycolide), polyhydroxybutyrate, polyhydroxyvalerate, trimethylene carbonate, polyanhydrides, polyorthoesters, poly(vinyl alcohol), poly(N-vinyl 2-pyrrolidone), poly(ethylene glycol), poly(hydroxyethylmethacrylate), n-vinyl-2-pyrrolidone, methacrylic acid, methyl methacrylate, and maleic anhydride, polycaprolactone, poly(amino acids) ie poly(L-lysine), poly(1-ornithine), poly(glutamic acid), polycyanoacrylates, polyphosphazenes, poly(lactic acid), poly(glycolic acid), crown ethers, cyclodextrins, cyclophanes, ethylene glycol, Methylacrylate, Para-xylylene, Biodegradable Copolymers, Copolymer Surface Coatings, Starch Polymers, Polylactic Acid, Cellophane, Tyrosine Polycarbonates Lactide and Glycolide Polymers, Collagen, PTFE, silicone, Keratin-Based Materials, Fibrous Composites—Carbon Fiber and Particles, Polymer Composites, Artificial/Natural Material Composites, Glass-Ceramic/Metal Composites, Glass-Ceramic/Nonmetal Composites, Dental Composites, Ormocer, hydrogels, timed-release foams, and polymeric carriers.

In a further aspect, the invention provides a method for the selective dissolution of a wound dressing in a subject, the method comprising the steps of first administering an alginate based wound dressing to a wound; and waiting a time of 1 day, 2 days, 3 days, 5 days, 7 days, 9 days, 11 days, 13 days, 15 days, 17 or more days, and then administering a composition comprising alginate lyase to the wound of the first step, wherein administration of the composition comprising alginate lyase provides selective dissolution of the wound dressing in the subject.

In one embodiment, the method further comprises the step of repeating the first three steps until the wound is healed. Thus, the steps of administering an alginate based wound dressing to a wound, waiting a time of 1 day, 2 days, 3 days, 5 days, 7 days, 9 days, 11 days, 13 days, 15 days, 17 or more days, and then administering a composition comprising alginate lyase to the wound of the first step, are repeated until the wound is healed. In another embodiment of the method, the alginate based wound dressing further comprises one or more therapeutic agents.

In a particular embodiment, the therapeutic agent is selected from the group consisting of: analgesics, antibiotics, antifungals, antivirals, enzymes, vaccines, gene delivery vectors, antibodies, hormones and recombinant glycoproteins.

In another particular embodiment, the wound is a burn.

In a particular embodiment of any one of the above mentioned aspects, the composition comprising an alginate lyase further comprises a divalent metal chelator.

In another aspect, the invention features a method of synthesizing a dissolvable wound dressing, the method comprising preparing an alginate solution, adding calcium carbonate, placing the alginate solution with undissolved calcium carbonate into a vacuum, rotating, and adding water to rinse away excess calcium carbonate, and thereby synthesizing a dissolvable wound dressing.

In one embodiment, the vacuum is applied to create a dried calcium alginate sheet. In another embodiment, the alginate solution is 0.25% w/v. In still a further embodiment, the calcium carbonate is added at a concentration of 10% w/v.

In another aspect, the invention features a wound dressing prepared by a method comprising the steps of preparing an alginate solution, adding calcium carbonate, placing the alginate solution with undissolved calcium carbonate into a vacuum, rotating, and adding water to rinse away excess calcium carbonate, and thereby preparing the wound dressing.

In another aspect the invention features a wound dressing prepared by the method of the invention as described herein, wherein the vacuum is applied to create a dried calcium alginate sheet.

In one embodiment of the method, the alginate solution is 0.25% w/v. In another embodiment, the calcium carbonate is added at a concentration of 10% w/v.

In a particular embodiment of any of the methods of the invention, the alginate biomaterial comprises D-mannuronic acid and D-guluronic acid.

In another particular embodiment of any of the methods of the invention the alginate biomaterial comprises an alginic acid.

In a particular embodiment of any of the methods of the invention, the alginate biomaterial is alginate. In a further embodiment, the alginate biomaterial is polymerized prior to administration In a further particular embodiment of any of the methods of the invention, the alginate is obtained from the group consisting of: *Macrocystis, Laminaria, Ascophyllum*, Chlorophyceae, Phaeophyceae, Rhodophyceae, and Cyanophyceae.

In a particular embodiment of any of the methods of the invention, the alginate is obtained from *Aminaria hyperborean.*

In one particular embodiment of any of the methods of the invention, the alginate is obtained from *Laminara digita.*

In a particular embodiment of any of the methods of the invention, the alginate is obtained from *Ascophyllum nodosum.*

In yet another particular embodiment of any of the methods of the invention, the alginate is a bacterial alginate.

In one embodiment, the bacterial alginate is obtained from a heterotrophic bacteria. In another embodiment, the heterotrophic bacterium is selected from the group consisting of: Pseudomonadaceae and Azotobacteriaceae.

In a particular embodiment of any of the methods of the invention, a divalent cation is administered with the alginate biomaterial.

In one embodiment, the divalent cation is selected from the group consisting of: $Ca^{2+}$, $Mg^{2+}$, $Ba^{2+}$, $Sr^{2+}$. In another embodiment, the divalent cation is a synthetic compound with divalent orientation. In a further embodiment, the divalent cation is calcium. In another embodiment, the divalent cation is administered in a liposome or a microbubble. In a particular embodiment, the liposome is selected from the group consisting of heat sensitive liposomes, ultraviolet sensitive liposomes and ph sensitive liposomes. In yet another embodiment, the divalent cation is administered simultaneously with the alginate biomaterial.

In a further particular embodiment of any of the methods of the invention, the divalent cation is administered after administration of the alginate based biomaterial.

In a particular embodiment of any of the methods of the invention, the composition comprising alginate lyase and the divalent metal chelator is administered locally.

In still another particular embodiment of any of the methods of the invention, the composition comprising alginate lyase and the divalent metal chelator is administered systemically.

In a particular embodiment of any of the methods of the invention, the composition comprising alginate lyase and the divalent metal chelator are co-administered.

In another particular embodiment of any of the methods of the invention, the composition comprising alginate lyase and the divalent metal chelator are co-administered from the same device.

In one embodiment, the device is a syringe, a microcatheter, a bronchoscope and an endoscope a syringe. In another embodiment, the device is a syringe.

In another particular embodiment of any of the methods of the invention, the composition comprising alginate lyase is administered at a dose of 1 nanoliter, 10 nanoliters, 20 nanoliters, 50 nanoliters, 100 nanoliters, 250 nanoliters, 500 nanoliters, 1 µl, 10 µl, 25 µl, 50 µl, 100 µl, 250 µl, 500 µl, 1 mL, 2 mL, 4 mL, 5 mL, 10 mL, 20 mL, 30 mL, 40 mL, 45 mL, 50 mL, or more. Preferably, the composition comprising alginate lyase is administered at a dose of 1 nanoliter per kg body weight to 50 mL per kg body weight.

In one particular embodiment, the alginate lyase and divalent metal chelator are administered at a ratio of 99:1, 98:2, 97:3, 96:4, 95:5, 90:10, 85:15, 80:20, 75:25, 70:30, 60:40, 50:50, 40:60, 30:70, 25:75, 20:80, 15:85, 10:90, 5:95, 4:96, 3:97, 2:98, 1:99.

In a further particular embodiment of any of the methods of the invention, the divalent metal chelator is a proteinaceous metal chelator.

In a particular embodiment of any of the methods of the invention, the divalent metal chelator is a non-proteinaceous metal chelator.

In a further particular embodiment of any of the methods of the invention, the divalent metal chelator is a calcium chelator.

In a particular embodiment of any of the methods of the invention, the chelator is selected from the group consisting of: EDTA, DTPA, DMSA, citrate, tartrate, dimercaptol, penicillamine, deferoxamine, dithizone, cisplatin, and chlorophyll.

In a further particular embodiment of any of the methods of the invention, the alginate lyase is a bacterial alginate lyase.

In one particular embodiment, the bacterial alginate lyase is selected from the group consisting of: *Flavobacterium, Burkholderia, Corynebacterium, Klebsiella, Photobacterium, Pseudoalteromonas, Pseudomonas, Rhodopirellula, Saccharophagus, Sphingomonas, Streptomyces, Vibrio,* and *Aspergillus*. In another particular embodiment, the alginate lyase is *Flavobacterium* alginate lyase. In another particular embodiment, the alginate lyase, or biologically active fragment thereof, comprises SEQ ID NO: 1, or a fragment thereof.

In a particular embodiment of any of the methods of the invention, the alginate lyase is a transgenic alginate lyase.

In another particular embodiment, the alginate lyase, or biologically active fragment thereof, comprises SEQ ID NO: 1, or a fragment thereof.

In another aspect, the invention features a composition comprising an alginate lyase.

In one embodiment, the composition further comprises a divalent metal chelator.

In another embodiment, the divalent metal chelator is a proteinaceous metal chelator. In another embodiment the divalent metal chelator is a non-proteinaceous metal chelator. In another embodiment, the divalent metal chelator is a calcium chelator. In a particular embodiment, the divalent metal chelator is selected from the group consisting of: EDTA, DTPA, DMSA, citrate, tartrate, dimercaptol, penicillamine, deferoxamine, dithizone, cisplatin, and chlorophyll. In another particular embodiment, the alginate lyase is a bacterial alginate lyase. In another particular embodiment the bacterial alginate lyase is selected from the group consisting of: *Flavobacterium, Flavobacterium, Burkholderia, Corynebacterium, Klebsiella, Photobacterium, Pseudoalteromonas, Pseudomonas, Rhodopirellula, Saccharophagus, Sphingomonas, Streptomyces, Vibrio,* and *Aspergillus*. In a particular embodiment, the alginate lyase is *Flavobacterium* alginate lyase. In a further r embodiment, the alginate lyase, or biologically active fragment thereof, comprises the amino acid sequence of SEQ ID NO: 1, or a fragment thereof.

In another aspect, the invention features a composition comprising an alginate based biomaterial and a contrast agent.

In one embodiment, the contrast agent is selected from the group consisting of: magnetic resonance contrast agents, radioopaque contrast agents, ultrasound contrast agents, and nuclear medicine imaging contrast agents. In a particular embodiment, the magnetic resonance contrast agent is selected from the group consisting of: Manganese Oxide, perfluorocarbons, Feridex, Gadolinium, Combidex, Bang Magnetic Particles, Gd-DTPA, Gadolinium And Manganese Derivatives, Superparamagnetic Iron Oxide Particles, gadopentetate dimeglumine, Gd-DOTA, Gd-DTPA-BMA, Gd-HP-DO3A, Gd-DTPA-BMEA, Gd-DO3A-butrol, Gd-BOPTA, Mn-DPDP, Gd-EOB-DTPA, Gd-BOPTA, AMI-25, SH U 555A, gadoflourine-M, AMI-227, EP-2104R, P947, Gd-DTPA mesophorphryn, SH U 555 C, NC-100150, MS-325, gadoflourine-M, gadomelitolm manganese chloride, ferric amonium citrate, and barium sulfate suspensions.

In another particular aspect, the invention features a composition comprising an alginate based biomaterial and a biocompatible material. In one particular embodiment, a portion of the biocompatible material does not dissolve when treated with alginate lyase. In another embodiment, the biocompatible material is selected from the group consisting of: polyvinyl alcohol, sodium polyacrylate, acrylate polymers, Hyaluronase Polymers, collagen membrane, Porous HA/TCP ceramic composite, Hydroxyapatite bone cement, PVP/PMMA, tricalcium phosphate, Hydroxyapatite coated collagen fibres, calcium sulphate, Hydroxyapatite (HAp), Phosphorylcholine (PC), silicone, ultrahigh molecular weight polyethylene, polyethylene, acrylic, nylon, Polyurethane, Polypropylene, poly(methyl methacrylate), Teflon, Dacron, acetal, polyester, silicone-collagen composite, polyaledehyde, poly(vinyl chloride), silicone-acrylate, poly(tetrafluoroethylene), hydroxyethyl methacrylate (HEMA), poly(methyl methacrylate) (PMMA), poly(glycolide lactide), poly(glycolic acid), tetrafluoroethylene, hexafluoropropylene, poly(glycolic acid), poly(lactic acid), desaminotyrosyl-tyrosine ethyl ester, polydioxanone, fibrin, gelatin, hyaluronan, tricalcium phosphate, polyglycolide (PGA), polycaprolactone, poly (lactide-co-glycolide), polyhydroxybutyrate, polyhydroxyvalerate, trimethylene carbonate, polyanhydrides, polyorthoesters, poly(vinyl alcohol), poly(N-vinyl 2-pyrrolidone), poly(ethylene glycol), poly(hydroxyethylmethacrylate), n-vinyl-2-pyrrolidone, methacrylic acid, methyl methacrylate, and maleic anhydride, polycaprolactone, poly(amino acids) ie poly(L-lysine), poly(1-ornithine), poly(glutamic acid), polycyanoacrylates, polyphosphazenes, poly(lactic acid), poly(glycolic acid), crown ethers, cyclodextrins, cyclophanes, ethylene glycol, Methylacrylate, Para-xylylene, Biodegradable Copolymers, Copolymer Surface Coatings, Starch Polymers, Polylactic Acid, Cellophane, Tyrosine Polycarbonates Lactide and Glycolide Polymers, Collagen, PTFE, silicone, Keratin-Based Materials, Fibrous Composites—Carbon Fiber and Particles, Polymer Composites, Artificial/Natural Material Composites, Glass-Ceramic/Metal Composites, Glass-Ceramic/Nonmetal Composites, Dental Composites, Ormocer, hydrogels, timed-release foams, and polymeric carriers.

In one aspect, the invention features a composition comprising an alginate based wound dressing.

In a particular embodiment, the alginate based wound dressing further comprises one or more therapeutic agents. In another particular embodiment, the therapeutic agent is selected from the group consisting of: analgesics, antibiotics antifungals, antivirals, enzymes, vaccines, gene delivery vectors, antibodies, hormones and recombinant glycoproteins.

In another aspect, the invention features an alginate lyase composition, the method comprising the step of mixing a divalent metal chelator with an alginate lyase.

In a particular aspect, the invention teaches a method of making an alginate lyase composition, the method comprising the steps of adding a divalent metal chelator to a buffer; and
adjusting the pH, and adding alginate lyase, thereby making the alginate lyase composition.

In one embodiment of the method, the divalent metal chelator is a proteinaceous metal chelator. In another embodiment of the method, the divalent metal chelator is a non-proteinaceous metal chelator. In a further embodiment of the method, the divalent metal chelator is a calcium chelator. In another embodiment of the method, the calcium chelator is selected from the group consisting of: EDTA, DTPA, DMSA, citrate, tartrate, dimercaptol, penicillamine, deferoxamine, dithizone, cisplatin, and chlorophyll. In a particular embodiment of the method, the divalent metal chelator is added at a concentration of 1 ng/ml, 2, ng/ml, 4 ng/ml, 10 ng/ml, 25 ng/ml, 50 ng/ml, 100 ng/ml, 200 ng/ml, 250 ng/ml, 500 ng/ml, 700 ng/ml, 1 µg/ml, 5 µg/ml, 10 µg/ml, 20 µg/ml, 25 µg/ml, 50 µg/ml, 75 µg/ml, 100 µg/ml, 250 µg/ml, 500 µg/ml, 700 µg/ml, 1 mg/ml, 2 mg/ml. 5 mg/ml, 6 mg/ml, 7 mg/ml, 8 mg/ml, 9 mg/ml, 10 mg/ml or more.-10 mg/ml. In another particular embodiment of the method, the alginate lyase is added at a Preferably, the divalent metal chelator is added at a concentration of 1 ng/ml-10 mg/ml.

In a particular embodiment, the alginate lyase is added at a concentration of 2 mg/ml. In a further particular embodiment, the pH is adjusted to 6.5, 6.6, 6.7, 6.8, 6.9, 7.0, 7.1, 7.2, 7.3, 7.4, 7.5.

In other particular aspects, the invention features a kit for use in dissolving an alginate based biomaterial in a subject, the kit comprising an alginate lyase, a divalent metal chelator, and instructions for use.

In one aspect, the invention features a kit for use in treating a subject that has received treatment with an alginate based biomaterial, the kit comprising an alginate lyase, and instructions for use.

In another aspect, the invention features a kit for use in treating a subject suffering from a vascular or non-vascular condition wherein the subject has previously received treatment with an alginate based biomaterial in accordance with any of the above claims, the kit comprising an alginate lyase, a divalent metal chelator, and instructions for use.

In another aspect, the invention features a kit for treating a subject suffering from a vascular or non-vascular occlusion, wherein the subject has previously received treatment with an alginate based biomaterial in accordance with any of the above claims, the kit comprising an alginate lyase, and instructions for use.

In a particular aspect, the invention features a kit for treating a subject suffering from a vascular or non-vascular hemorrhage, wherein the subject has previously received treatment with an alginate based biomaterial in accordance with any of the above claims, the kit comprising an alginate lyase, and instructions for use.

In one aspect, the invention features a kit for treating a subject suffering from a neoplastic growth in accordance with any of the above claims, wherein the subject has previously received treatment with an alginate based biomaterial for the neoplastic growth, the kit comprising an alginate lyase, and instructions for use.

In one aspect, the invention features a kit for the selective dissolution of an occlusion in a subject, the kit comprising an alginate based biomaterial, alginate lyase, and instructions for use.

In another aspect, the invention features a kit for the selective dissolution of an occlusion in a subject in accordance with any of the above claims, wherein the subject has received treatment with an alginate based biomaterial, the kit comprising alginate lyase, and instructions for use.

In one aspect, the invention features a kit for the selective delivery of a therapeutic agent to a targeted non-occluded vessel in accordance with any of the above claims, the kit comprising, an alginate based biomaterial, alginate lyase, a divalent metal chelator, and instructions for use.

In a further aspect, the invention features a kit for the selective control of bulking or remodeling in a subject in accordance with any of the above claims, the kit comprising an alginate based biomaterial, alginate lyase, and instructions for use.

In another aspect, the invention features a kit for the controlled release of an agent in a subject in accordance with any of the above claims, the kit comprising an alginate based biomaterial comprising an agent, alginate lyase, and instructions for use.

In a further aspect, the invention features a kit for the controlled release of a label in a subject in accordance with any of the above claims, the kit comprising an alginate based biomaterial with a label linked to it, alginate lyase, and instructions for use.

In another aspect, the invention features a kit for the controlled release of a label to mark lesions for radiosurgery in a subject that has received treatment with an alginate based biomaterial linked to a label in accordance with any of the above claims, the kit comprising alginate lyase, and instructions for use.

In another particular aspect, the invention features a kit for the controlled release of a contrast agent in a subject in accordance with any of the above claims, the kit comprising an alginate based biomaterial linked to a contrast agent, alginate lyase, and instructions for use.

In another aspect, the invention features a kit for lung volume reduction therapy in a subject, the kit comprising an alginate based biomaterial, alginate lyase and instructions for use In yet another aspect, the invention features a kit for the selective dissolution of a biocompatible material in a subject in accordance with any of the above claims, the kit comprising an alginate loaded biocompatible material, alginate lyase, and instructions for use.

In another aspect, the invention features a kit for the selective dissolution of a wound dressing in a subject in accordance with any of the above claims, the kit comprising an alginate based wound dressing, alginate lyase and instructions for use.

In another aspect, the invention features a kit for treating or preventing osteoporosis in a subject, the kit comprising an alginate based biomaterial, alginate lyase and instructions for use.

In a further aspect, the invention features a kit comprising any one of the compositions according to any of the above claims, and instructions for use.

In a particular preferred embodiment of any one of the above-mentioned aspects, the kits further comprise a divalent metal chelator In a particular aspect, the invention provides a composition for dissolving an alginate based biomaterial in a subject, the composition consisting of 2 mg/ml alginate lyase in a 5 mg/ml EDTA buffer solution.

Other features and advantages of the invention will be apparent from the detailed description, and from the claims.

DEFINITIONS

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The term "administration" or "administering" is meant to include an act of providing a compound or pharmaceutical composition of the invention to a subject in need of treatment.

The term "alginate" is meant to refer to the sodium salt of alginic acid. IN preferred embodiments, alginic acid refers to a linear copolymer with homopolymeric blocks of (1-4)-linked β-D-mannuronate (M) and its C-5 epimer α-L-guluronate (G) residues, respectively, covalently linked together in different sequences or blocks.

The term "alginate based biomaterial" is meant to refer to a biomaterial wherein all or a portion of the active agent contains homopolymeric blocks of (1-4)-linked β-D-mannuronate (M) and/or its C-5 epimer α-L-guluronate (G) residues. EmboGel is an example of a commercially available alginate based biomaterial that is known in the art.

The term "alginate lyase" is meant to refer to enzymes that catalyze the degradation of alginate. Alginate lyases can be characterized as either mannuronate (EC4.2.2.3) or guluronate lyases (EC 4.2.2.11), and both catalyze the degradation of alginate. Mannuronate specific alginate lyase cleaves at the β-(1-4)-D-mannuronic bonds residues of alginate to yield oligosaccharides with 4-deoxy-a-L-erythro-hex-4 enopyranuronosyl groups at their non-reducing terminus. Alginate lyases have been isolated from a wide range of organisms, including algae, marine invertebrates, and marine and terrestrial microorganisms.

The term "aneurysm" refers to the dilation, bulging, or ballooning out of part of the wall of a vein or artery. The aorta can sometimes develop an aneurysm. Aortic aneurysms usually occur in the abdomen below the kidneys. A brain aneurysm, also called a cerebral or intracranial aneurysm, is a weak bulge in the blood vessel in the brain The term "biocompatible material" is meant to refer to any synthetic or natural material that can be used to replace part of a living system, or any synthetic or natural material that can function in intimate contact with living tissue.

The term "contrast agent" is meant to refer to agents that are useful in imaging techniques or methods, such as, but not limited to, magnetic resonance imaging, CT scan, ultrasound, nuclear magnetic imaging. Contrast agents can be, but are not limited to, magnetic resonance contrast agents, radioopaque contrast agents, ultrasound contrast agents, and Nuclear Medicine Imaging contrast agents.

The term "calcium agent" is meant to refer to an agent that promotes the hardening (gelation) of alginate. A calcium agent can be a solution of calcium, for example calcium chloride. A calcium agent can also refer to calcium holding containers. For example, liposomes, or microcapsules, or any other biological container that holds calcium or a calcium agent.

The term "co-administer" is intended to refer to all forms of administration that provide the alginate lyase and the divalent metal chelator, and can include sequential administration, in any order.

The term "controlled release" is meant to refer to the release of any one agent that occurs as a result of the administration of a second releasing agent. The agents can be administered in any order. In exemplary embodiments, an alginate based biomaterial comprises an agent, and an alginate lyase is used for the controlled release of the agent. For example, an alginate based biomaterial comprising an agent is administered to a subject, and a composition comprising alginate lyase and a metal chelator, for example a divalent metal chelator, is administered to the subject, thus resulting in selective release of the first agent. The selective release can be, for example, of a drug, a label, or an imaging compound.

The term "diagnosis" refers to a process of determining if an individual is afflicted with a disease or ailment, for example a vascular or non-vascular condition. A vascular condition can include arteriovenous malformation, neurovascular lesions, telangiectasias, varicoceles, varicose veins, inflammatory lesions, hemorrhage, occlusion, embolism, neoplastic growth, venous disease, and phlebitis.

The term "dissolution" or "dissolving" is meant to refer the process of breaking up or liquefiying a substance into a liquid. Dissolution can mean the process of the breakdown of an alginate based biomaterial in to smaller components by an enzymatic cleavage reaction.

The term "divalent cation" is intended to include any metal ion with two or more possible charges. The term can also refer to a synthetic compound with appropriately spaced positive charges such that the synthetic compound has the properties of a divalent cation. Examples of divalent cations include, but are not limited to, $Ca^{2+}$, $Mg^{2+}$, $Ba^{2+}$, and $Sr^{2+}$. In certain embodiments, the metal ion with two or more charges is contained within a liposome.

The term "divalent metal chelator" is meant to refer to a substance that binds particular ions, removing them from solution, in this case a substance that particularly removes divalent metal ions. Divalent metal chelators can be proteinaceous or non-proteinaceous chelators. Divalent metal chelators according to the invention can include, but are not limited to, EDTA, DTPA, DMSA, citrate, tartrate, dimercaptol, penicillamine, deferoxamine, dithizone, cisplatin, and chlorophyll.

The term "embolism" is meant to refer to a blockage or clot. An embolism can be the result of a blockage caused by an alginate based biomaterial. An embolism can be caused by a blood clot that travels to the lung.

The term "loaded" is meant to refer to a process of impregnating or saturating or filling another material or container. In specific embodiments, the material or container is biocompatible. For example, a biocompatible material of the invention can be loaded with alginate lyase composition.

The term "hemorrhage" is meant to refer to a discharge of blood from the blood vessels. A hemorrhage can occur in the vasculature, and is thus termed a vascular hemorrhage.

The term "nanomaterial" is meant to refer to a particle having one or more dimensions of the order of 100 nm or less. Examples of nanomaterials according to the invention include, but are not limited to, microboxes, microchips, microfluidic pumps, magnetic resonance microcoil, quantum dots, antibody targeted nanomaterials, nanocontainers, and nanoboxes.

The term "neoplastic growth" or "neoplasia" is meant to refer to any disease that is caused by or results in inappropriately high levels of cell division, inappropriately low levels of apoptosis, or both. For example, cancer is an example of a neoplasia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). Lymphoproliferative disorders are also considered to be proliferative diseases.

The term "non-vascular condition" is meant to refer to a disease or condition that does not involve the vasculature. Non-vascular conditions are conditions that do not affect the blood vessels. Examples include, but are not limited to, a broken bone or fracture, an infection, an immunodeficiency disorder, or a metabolic disease.

The term "occlusion" or "vascular occlusion" is meant to refer to a constriction or blockage as can occur in a blood vessel. An occlusion can be the result of a blockage created with an alginate based biomaterial.

The term "simultaneously" is intended to refer to administration that occurs at the same time. The term is intended to refer to all forms of administration that provide the compositions of the invention together at the same time.

The term "subject" is intended to include vertebrates, preferably a mammal. Mammals include, but are not limited to, humans.

The term "treatment" or "treating" can mean: treating or ameliorating disease and or symptoms.

The term "vascular condition" is meant to refer to a condition that affects the blood vessels. Vascular conditions can include vascular disease, which affects the body's network of blood vessels (arteries and veins) that distribute oxygen and nutrient-rich blood to the body, and bring back deoxygenated blood to the heart and lungs from the rest of the body. Vascular disease can include, but is not limited to, arterial vascular disease and venous vascular disease. A vascular condition can be a vascular lesion. A vascular condition can be, but is not limited to, an occlusion, an embolism, or a hemorrhage.

The term "wound dressing" is meant to refer to a covering for a wound. The covering can be an alginate based wound covering. The alginate based covering can be a solid dressing, more specifically a solid wound dressing comprised of an alginate based biomaterial. In specific examples, the wound dressings are capable of delivering an effective wound-healing agent.

BRIEF DESCRIPTION OF THE DRAWINGS

FIG. 1 (a-f) is six panels showing an in vitro model of a saccular aneurysm filled with an alginate based biomaterial under fluoroscopy. a) shows the stent delivery system is advanced across the neck of the aneurysm, b) shows deployment of the stent, c) shows the stent in place after removal of the delivery system, d) shows puncture of the coated stent by the tip of a catheter, e) shows embolization of the aneurysmal cavity with the alginate based biomaterial, f) is the final image showing complete aneurysm obliteration.

FIG. 2 (a-c) is three panels. Panel a) shows the alginate lyase composition is injected across the covered stent to dissolve the alginate based biomaterial into a liquid that can freely pass through the stent micropores. Panels b) and c) show progressive alginate based biomaterial dissolution with a clear aneurysmal cavity as final result in panel c).

FIG. 4 (*a-d*) is four panels that show in vivo proof of principle of the alginate lyase composition. Panel a) is a distal abdominal angiogram with opacification of right and left iliac arteries and pelvic vasculature. Panel b) shows embolization of both iliac arteries and a portion of the aorta with alginate based biomaterial. Panel c) is an angiogram confirming that the distal aorta and the iliac arteries are occluded. Panel d) is a control angiogram 60 seconds after delivering the alginate lyase composition, demonstrating nearly complete dissolution of alginate based biomaterial and flow through the aorta to the iliac arteries.

FIG. 5 (*a-c*) is three panels showing simulation of an endovascular therapy complication in a New Zealand White rabbit aneurysm model. Digital subtraction angiography of the lesion before treatment in panel a) shows a wide neck aneurysm originating from the right subclavian artery. After injection of alginate based biomaterial without protection of the neck with a stent or a balloon, the alginate located at the interface between the aneurysm and the parent artery has migrated distally, causing diffuse flow impairment and several branch occlusions in the subclavian artery distribution, as shown in panel b). The white arrowheads point to some of the white artifactual lines representing embolic alginate occluded branches. After infusion of 2 ml of alginate lyase composition solution into the aneurysmal cavity, the alginate based biomaterial has been dissolved, and the patency of the occluded branches has been re-established, shown in panel c).

FIG. 6 (*a-d*) is four panels showing simulation of inadvertent embolization in the cranial circulation of a New Zealand White rabbit aneurysm model (as in FIG. 5). Initial DSA from the left carotid shows bilateral cerebral opacification (there is no right carotid circulation in this animal). The arrowheads point to the choroids blush of the left eye. In panel a) and b) a large amount of alginate was injected in the carotid circulation, and the arrowheads indicate alginate emboli. Digital Subtraction Angiography confirms severe cerebral flow impairment after alginate injection. Note the absence of the left choroids blush. After administration of 3 ml of alginate lyase composition, the cerebral circulation has been re-established. In panel d), note the persistent occlusion of a branch for the right ear, as indicated with an arrow, but the reappearance of the left choroids blush, as shown with an arrowhead, confirming the patency of very small arterial structures. Panel C is occlusion of vessels after administration of alginate based biomaterial (as compared to Panel A).

FIG. 9 shows SEQ ID NO: 1 that corresponds to the nucleotide sequence of alginate lyase from *Pseudomonas aeruginosa*.

FIG. 19 (*a-c*) is three panels. Panel a) shows a concentric 5 french catheter advanced into a distal lung segment under x-ray fluoroscopy in a New Zealand White rabbit. Panel b) shows injection of 0.1 mL of EmboGel and 0.1 mL of calcium chloride. Panel c) shows injection of 0.4 mL of EmboGel and .mL of calcium chloride for a total delivery of 0.5 mL of EmboGel.

Figure 22:
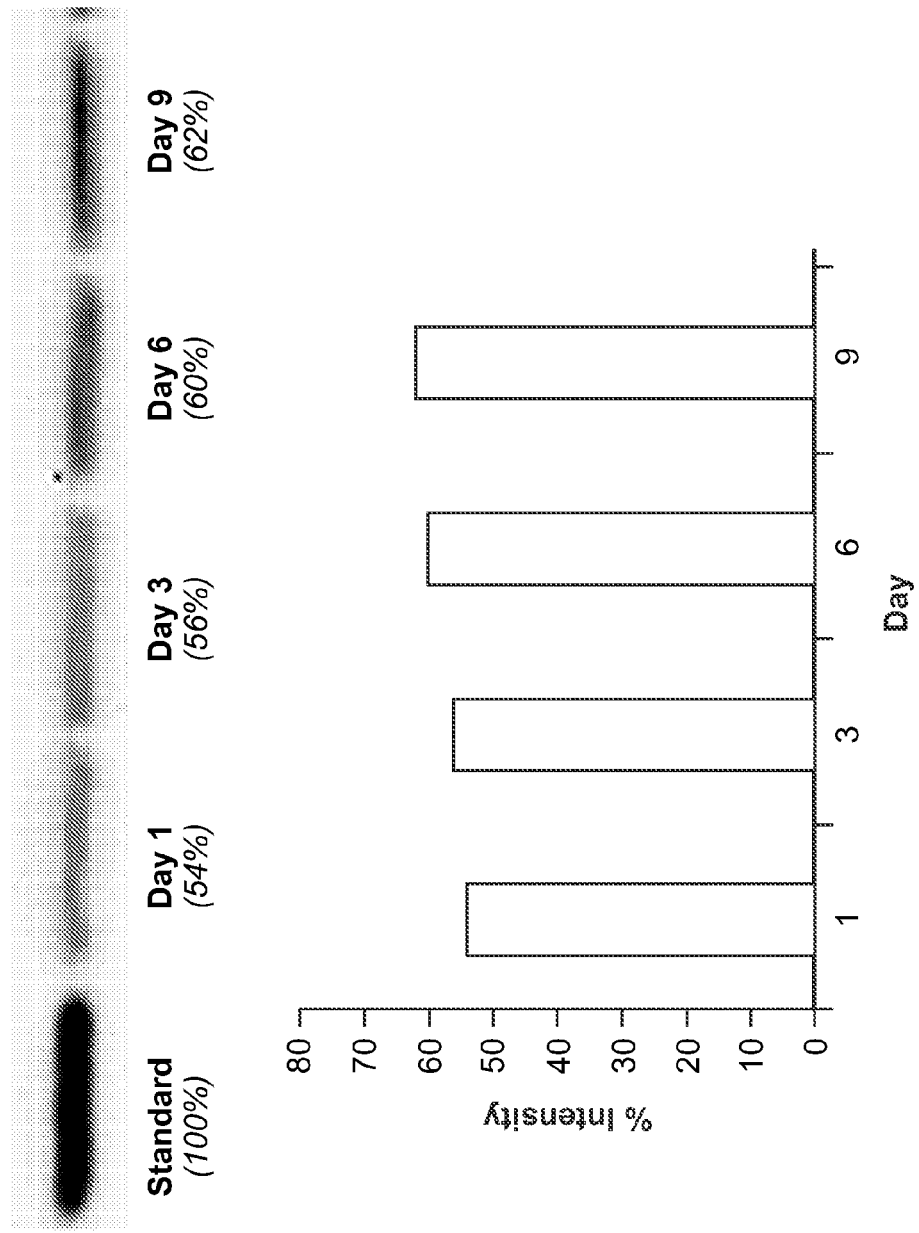

FIG. 22 (a and b) shows Western blot for the heavy chain of Botox-A in the supernatant of EmboCaps revealed that the heavy chain was not denatured (FIG. 22a). Assessment of band intensity revealed that Botox-A was slowly released in the absence of EmboClear (FIG. 22b). The results from the western blot show that the protein was neither degraded nor did it aggregate during the preparation.

DETAILED DESCRIPTION OF THE INVENTION

The invention features alginate and alginate lyase compositions and methods that are useful for the treatment of various conditions and diseases. The invention also provides kits and instructions for use.

The present invention provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a vascular or non-vascular condition. The method includes the step of administering to the mammal a therapeutic amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention in general comprise administration of a therapeutically effective amount of the compounds herein, such as a compound of the formulae herein, to a subject (e.g., animal, human) in need thereof, including a mammal, particularly a human. Such treatment will be suitably administered to subjects, particularly humans, suffering from, having, susceptible to, or at risk for a disease, disorder, or symptom thereof. The compounds herein may be also used in the treatment of any other disorders in which vascular or non-vascular lesions may be implicated.

Alginic Acid

Alginate is the sodium salt of alginic acid. Sodium alginate is considered Generally Recognized as Safe (GRAS) by qualified experts, and is in accordance with United States Food and Drug Regulations. Alginic acid is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks), alternating M and G-residues (MG-blocks) or randomly organized blocks. The relative amount of each block type varies both with the origin of the alginate and the concentration of G and M acids (the G/M ratio), and thus contributes to varied structural and biocompatibility characteristics. Alternating blocks form the most flexible chains, and are more soluble at lower pH than the other blocks. G-blocks form stiff chain elements, and two G-blocks of more than 6 residues each form stable cross-linked junctions with divalent cations (e.g. $Ca^{2+}$, $Mg^{2+}$, $Ba^{2+}$, $Sr^{2+}$ among others), leading to a three-dimensional gel network. Purified alginates with a high G acid content (PHG) have optimal material properties for use in endovascular occlusion. As such, alginate is a highly biocompatible material with desirable characteristics for filling and occluding vessel lesions.

Most of the alginate used commercially is obtained from three genera, *Macrocystis, Laminaria,* and *Ascophyllum*. Specific sources included *Aminaria hyperborean, Laminara digita* and *ascophyllum nodosum*. Nevertheless, alginate is present, and could potentially be isolated, from any Chlorophyceae (the green algae), Phaeophyceae (the brown algae), Rhodophyceae (the red algae) and Cyanophyceae (the blue-green algae). Alginate is also produced by two families of heterotrophic bacteria, the Pseudomonadaceae and the Azotobacteriaceae, and is often produced under strict regulatory control. The most common bacterial strains for the production of alginate are *Azobacter Vinelandii* and *Pseudomonas Aueriginosa*.

In addition, alginate can be combined with magnetic resonance imaging and/or ultrasound contrast agents, in order to provide visibility during procedures performed with these imaging modalities. Alginate compositions according to the invention can use magnetic resonance (MR) contrast agents such as iron-based agents, gadolinium-based agents, and fluorinated contrast agents. Specific contrast agents include bang magnetic particles, manganese oxide, gadopenteltated-imeglumine, gadoteratemeglumine (Gd-DOTA), gadodiamide injection (Gd-DTPA-BMA), gadoteridol injection (Gd-HP-D03A), gadoversetamide (Gd-DTPA-BMEA), gadobutrol (Gd-D03A-butrol), gadobenate dimeglumine (Gd-BOPTA), megafodipir trisodium (Mn-DPDP), gadoxetic acid (Gd-EOB-DTPA), feuromoxides (AMI-25), ferucarbotran (SH U 555A), gadofluorine-M, ferumoxtran (AMI-227), EP-2104R, P947, Gd-DTPA mesoporphyrin, PEG-feron (NC-100150), ferucarbotran (SH 555 C), gadofosveset (MS-325), ferumoxytol (Code 7228), gadomer-17, gadomelitol (p792), MnHa/PEG, ferric ammonium citrate, manganese chloride, manganese-loaded zeolite, ferristene (OMP), ferumoxsil (AMI-121), perfluoro-octylbromide, barium sulfate, bismuth sulfate, miscellaneous perfluorocarbons, hexafluorobenze, perfluoropolyether, Gd-DTPA, gadolinium and manganese derivatives, miscellaneous superparamagnetic iron oxide particles. In particular, bromofluorocarbons provide Hotspot imaging on 19F magnetic resonance imaging (MRI), and have sufficient radio-opacity to be conspicuous on CT, and thus are attractive agents to use.

The visibility of alginate can be set to persist on a long-term basis, or to decrease after administration at a pace that can be controlled, for example with the use of a clearing agent, for example alginate lyase or epimerase. This allows using a formulation of an alginate biomaterial that combines transient radio-opacity and long-term magnetic resonance (MR) signal. The embolic material would thus be optimally radio-opaque for safe delivery at the time of the therapeutic procedure, have its radio-opacity decrease shortly after injection in order to avoid beam-hardening artifacts on follow-up CT studies, while retaining MR signal for long-term non invasive follow up imaging studies.

Potential ultrasound agents that can be incorporated with alginate include AI-700, Albunex, BG1135, BiSphere™, BR14, BY 963, CARDIOSPHERE, DEFINIEY, ECHOGEN, ECHOVIST-200, IMAGENT, IMAVIST, LEVOVISTt, M1091, M1134, MP1950, MRX 115, MRX 408, MYOMAP, OPTISON, PESDA, Quantison, QW7437, SONAZOID, SONOGEN, SONORX, SONOVIST, SONOVUE, VISIPAQUE, ultra-small air bubbles, silica nanoparticles, perfluorocarbons, liposheres, or any combination of shell composed of albumin, lipid, or polymer confining a gas such as nitrogen, or a perfluorocarbon.

By using liquid contrast agents as opposed to metal powders, alginate biomaterials can be safely dissolved without causing systemic release of metal powders. Radioopaque contrast agents are useful in particular embodiments of the invention. Potential radioopaque contrast agents that are useful for dissolving or combining with alginate include ethiodized oil, tantalum powder, barium sulfate, bismuth sulfate, Acetrizoic Acid Derivatives, Diatrizoic Acid Derivatives, Iothalamic Acid Derivatives, Ioxithalamic Acid Derivatives, Metrizoic Acid Derivatives, Iodamide, Lypophylic Agents, Aliphatic Acid Salts, Iodipamide, Ioglycamic Acid, Ioxaglic Acid Derivatives, Metrizamide Iopamidol, Iohexyl, Iopromide, Iobitridol, Iomeprol, Iopentol, Ioversol, Ioxilan, Iodixanol, Iotrolan, and Perfluorocarbons (PFOB).

Alginate can be polymerized by any divalent cation. Further, it is possible that a synthetic compound with proper divalent orientation could also replace calcium.

Alginate can be cleaved by a number of enzymes. Alginate lyases can cleave alginate. Epimerases are another class of enzymes that cleave alginate but are not specifically alginate lyases. Specifically, mannuronan c-5 epimerases, which are found in many species, can cleave alginate. The chemical mechanism and specificity of the epimerase for alginate are described by Jerga et al. (Biochemistry 2006 (45), 9138-9144), and incorporated herein by reference in its entirety.

Using alginate gels for embolization or treatment of aneurysms, including co-injection of a calcium chloride-alginate mix for polymerization has been described in WO 2005/05820, as well as U.S. Patent Application 20050133046 (Becker et al), both of which are herein incorporated by reference in their entireties. U.S. Pat. No. 6,113,629 describes radio-opaque alginate gels for the treatment of aneurysms, and is herein incorporated by reference in its entirety. Use of alginate biomaterial may include an agent for post-procedure vascular puncture closure, for filling fistulas (for example, tracheoesophageal or gastrointestinal) or surgical created fistulas, for example to fill the void where gastric tube was placed.

Alginate Lyase

Alginate lyases, characterized as either mannuronate (EC 4.2.2.3) or guluronate lyases (EC 4.2.2.11) catalyze the degradation of alginate, a complex copolymer of α-L-guluronate and its C5 epimer β-D-mannuronate. Alginate lyase cleaves at the b-(1-4)-D-mannuronic bonds residues of alginate to yield oligosaccharides with 4-deoxy-a-L-erythro-hex-4 enopyranuronosyl groups at their non-reducing terminus. Alginate enzymatic hydrolysis with the alginate lyase enzyme creates polymannuronic acid (MW 5-10 kD). Alginate lyases have been isolated from a wide range of organisms, including algae, marine invertebrates, and marine and terrestrial microorganisms (Wong, T Y et al. Ann Rev of Microbiol 2000 54: 289-340, herein incorporated by reference).

Alginate lyase can be obtained from a number of sources; including bacterial sources. The production of alginate lyase from *Enterobacter cloacae* is described in U.S. Pat. No. 5,348,875, which is herein incorporated by reference in its entirety. Table 1 below lists exemplary sources of alginate lyase:

TABLE 1

| | |
|---|---|
| Bcep18194_B2401 | *Burkholderia* sp. 383 |
| guluronate lyase (alyPG) | *Corynebacterium* sp. ALY-1 |
| alginate lyase (AlyA) | *Klebsiella pneumoniae* subsp. aerogenes |
| alginate lyase AlxM | *Photobacterium* sp. ATCC 43367 |
| Patl_3645 | *Pseudoalteromonas atlantica* T6c |
| Patl_3639 | *Pseudoalteromonas atlantica* T6c |
| PSHAa0571 | *Pseudoalteromonas haloplanktis* TAC125 |
| alginate lyase (PA1167) | *Pseudomonas aeruginosa* PAO1 |
| PA1784 | *Pseudomonas aeruginosa* PAO1 |
| PFL_5780 | *Pseudomonas fluorescens* Pf-5 |
| PFL_3421 | *Pseudomonas fluorescens* Pf-5 |
| PFL_4740 | *Pseudomonas fluorescens* Pf-5 |
| Pfl_5256 | *Pseudomonas fluorescens* PfO-1 |
| PP3774 | *Pseudomonas putida* KT2440 |
| PSPPH_3296 | *Pseudomonas syringae* pv. phaseolicola 1448A; BAA-978 |
| PSPPH_0498 | *Pseudomonas syringae* pv. phaseolicola 1448A; BAA-978 |
| Psyr_0508 | *Pseudomonas syringae* pv. syringae B728a |
| Psyr_3376 | *Pseudomonas syringae* pv. syringae B728a |
| PSPTO5015 | *Pseudomonas syringae* pv. tomato str. DC3000 |
| PSPTO3605 | *Pseudomonas syringae* pv. tomato str. DC3000 |
| RB3601 | *Rhodopirellula baltica* SH 1 |
| Sde_1507 | *Saccharophagus degradans* 2-40 |
| Sde_3286 | *Saccharophagus degradans* 2-40 |
| Sde_2839 | *Saccharophagus degradans* 2-40 |
| Sde_2478 | *Saccharophagus degradans* 2-40 |
| Sde_2873 | *Saccharophagus degradans* 2-40 |
| Sde_2547 | *Saccharophagus degradans* 2-40 |
| alginate lyase (A1-II') | *Sphingomonas* sp. A1 |
| alginate lyase (aly; A1-I/PolyG + PolyM; A1-II/PolyG; A1-III/PolyM) | *Sphingomonas* sp. A1 |
| SAV802 | *Streptomyces avermitilis* MA-4680 |
| Q9RKE1 or SCE65.33c | *Streptomyces coelicolor* A3(2) |
| alginate lyase (Aly1) (fragment) | *Streptomyces* sp. MET0515 |
| alginate lyase AlyVGII | *Vibrio halioticoli* IAM14596T |
| alginate lyase AlyVGI | *Vibrio halioticoli* IAM14596T |
| alginate lyase (AlyVI) | *Vibrio* sp. QY101 |
| AO090020000698 | *Aspergillus oryzae* RIB 40 |

An exemplary alginate lyase according to the invention, alginate lyase from *Pseudomonas aeruginosa*, is shown in SEQ ID NO: 1.

```
                                              SEQ ID NO: 1
MKTSHLIRIA LPGALAAALL ASQVSQAADL VPPPGYYAAV

GERKGSAGSC PAVPPPYTGS LVFTSKYEGS DSARATLNVK

AEKTFRSQIK DITDMERGAT KLVTQYMRSG RDGDLACALN

WMSAWARAGA LQSDDFNHTG KSMRKWALGS LSGAYMRLKF

SSSRPLAAHA EQSREIEDWF ARLGTQVVRD WSGLPLKKIN

NHSYWAAWSV MSTAVVTNRR DLFDWAVSEF KVAANQVDEQ

GFLPNELKRR QRALAYHNYA LPPLAMIAPF AQVNGVDLRQ

ENHGALQRLA ERVMKGVDDE ETFEEKTGED QDMTDLKVDN

KYAWLEPYCA LYRCEPNACS RPKKDREPFN SFRLGGEVTR

VFSREGGS
```

An exemplary source of alginate lyase according to the invention is isolated from *Flavobacterium*. In certain embodiments, modification to alginate lyase may be made to enhance activity and/or reduce toxicity. Exemplary modifications include pegylation or chemical modification. Other modifications to alginate lyase are made to increase the speed of dissolution of alginate. Some modifications include, but are not limited to, the addition of buffering agents, including glycine; sodium citrate; citric acid, bicarbonate buffers (sodium carbonate, sodium bicarbonate), phosphate buffer, protein buffer, TRIS (tromethamine) buffer, veronal buffer, Krebs buffer, Butterfield phosphate buffer, lactic acid, 3-{[tris (hydroxymethyl)methyl]amino}propanesulfonic acid, N,N-bis(2-hydroxyethyl)glycine, tris(hydroxymethyl)methylamine, N-tris(hydroxymethyl)methylglycine, 4-2-hydroxyethyl-1-piperazineethanesulfonic acid, 2-{[tris (hydroxymethyl)methyl]amino}ethanesulfonic acid, 3-(N-morpholino) propanesulfonic acid, piperazine-N,N'-bis(2-ethanesulfonic acid), dimethyl arsenate, 2-(N-morpholino) ethanesulfonic acid, acetate, citric acid-phosphate buffer, MES, ADA, PIPES (piperazine-N,N'-bis(2-ethanesulfonic acid)), ACES (N-(2-Acetamido)-2-aminoethanesulfonic acid), Cholamine chloride, BES, TES, Acetamidoglycine, Tricine, Glycinamide, Bicine, [and substitution of other chelating agents, such as DTPA or DMSA in place of EDTA.

The use of alginate lyase compositions of the invention is not limited to dissolving alginate in strand form only. The compositions can also be use to dissolve or partially dissolve materials that consist entirely or in part of alginate. Such materials include but are not limited to tissue scaffolds, microcapsules, caps or spheres, and wound dressings. In particular embodiments, alginate lyase compositions may prove highly useful in the release of drug or radioisotope-containing liposomes from alginate microcapsules to a targeted tissue. A target organ or tissue could be embolized with alginate microcapsules containing therapeutic liposomes, which could then be released by systemic or selective administration of alginate lyase, or any enzyme that dissolves alginate.

Alginate lyase on its own has therapeutic potential. Studies looking at the safety and efficacy of bacterial alginate lyase are already underway in animal models, in regard to the potential use of alginate lyase in the treatment of cystic fibrosis patients infected with *Pseudomonas aeruginosa*, which proliferates in alginate biofilms.

Methods of the Invention

The present invention relates in certain embodiments to a method for dissolving an alginate based biomaterial in a subject.

The method comprises the step of administering to the subject a composition comprising an alginate lyase. In certain embodiments, the method comprises the step of administering to the subject a composition comprising an alginate lyase and a divalent metal chelator. Accordingly, the compositions may or may not comprise a divalent metal cheloator. In certain embodiments it is preferable to the methods of the invention to use the alginate lyase composition without a divalent metal chelator to slow down the dissolution of the alginate based biomaterial in a subject, or in embodiments where a divalent metal chelator, such as EDTA, might be toxic to an individual. For instance, application of the alginate lyase composition without a divalent metal chelator may be preferable in situations where the alginate based biomaterial is used as a wound dressing, e.g. as smartskin, as described herein.

Alginate based biomaterials can be selectively dissolved after application, using an alginate lyase based composition. The final product of the dissolution consists in a biocompatible molecule. This property adds safety to endovascular procedures, since the passage of embolic material in a non-targeted vessel, a complication with potentially devastating consequences, can be rapidly reversed by selective dissolution with alginate lyase. Reported instances of such untoward events include for example migration of embolic agent into a brain artery causing a stroke, or into a pulmonary artery causing a pulmonary embolism. In addition to this safety features, the dissolving property of alginate lyase can be used for selective release of bioactive agents, in remote locations and at a controlled pace.

Encompassed by the invention are methods for treating a subject suffering from a vascular or non-vascular condition, wherein the subject has previously received treatment with an alginate based biomaterial, the method comprising the step of administering to the subject a composition comprising an alginate lyase and a divalent metal chelator, and thereby treating the subject.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

The present invention provides methods for treating a subject suffering from a vascular or non-vascular occlusion, wherein the subject has previously received treatment with an alginate based biomaterial, the method comprising the step of administering to the subject a composition comprising an alginate lyase and a divalent metal chelator, and thereby treating the subject.

The present invention provides methods for treating a subject suffering from a vascular or non-vascular hemorrhage, wherein the subject has previously received treatment with an alginate based biomaterial, the method comprising the step of administering to the subject a composition comprising an alginate lyase, and thereby treating the subject. In certain embodiments, the composition may further comprise a divalent metal chelator.

A "vascular condition" is a condition that affects the blood vessels. Non-vascular conditions are conditions that do not affect the blood vessels.

Vascular conditions include vascular disease, which affects the body's network of blood vessels (arteries and veins) that distribute oxygen and nutrient-rich blood to the body, and bring back deoxygenated blood to the heart and lungs from the rest of the body. Arterial vascular disease is primarily caused by fatty deposits called plaque that lead to hardening of the arteries, or atherosclerosis. This can restrict blood flow in areas outside the heart, including the legs, arms, brains, torso and neck. (The term "cardiovascular" refers to the heart and its network of arteries and veins.) Arterial vascular disease includes stroke, aneurysms, carotid artery disease, varicose veins and more.

Venous vascular disease primarily affects the veins in the legs, caused by plaque build-up that blocks blood flow or stagnant blood flow or injury to blood vessels.

A vascular condition can be a vascular lesion. Arteriovenous malformations (AVMs) are defects of the circulatory system that are generally believed to arise during embryonic or fetal development or soon after birth. They are comprised of snarled tangles of arteries and veins. Arteries carry oxygen-rich blood away from the heart to the body's cells; veins return oxygen-depleted blood to the lungs and heart. The presence of an AVM disrupts this vital cyclical process. Although AVMs can develop in many different sites, those located in the brain or spinal cord can have especially widespread effects on the body. One of the greatest potential dangers posed by AVMs is hemorrhage. Information on AVMs can be found on the world wide web at ninds.nih.gov/disorders/avms/detail_avms.htm.

AVMs can form virtually anywhere in the brain or spinal cord—wherever arteries and veins exist. Some are formed from blood vessels located in the dura mater or in the pia mater, the outermost and innermost, respectively, of the three membranes surrounding the brain and spinal cord. (The third membrane, called the arachnoid, lacks blood vessels.) AVMs affecting the spinal cord are of two types, AVMs of the dura mater, which affect the function of the spinal cord by transmitting excess pressure to the venous system of the spinal cord, and AVMs of the spinal cord itself, which affect the function of the spinal cord by hemorrhage, by reducing blood flow to the spinal cord, or by causing excess venous pressure. Spinal AVMs frequently cause attacks of sudden, severe back pain, often concentrated at the roots of nerve fibers where they exit the vertebrae; the pain is similar to that caused by a slipped disk. Dural and pial AVMs can appear anywhere on the surface of the brain. Those located on the surface of the cerebral hemispheres—the uppermost portions of the brain—exert pressure on the cerebral cortex, the brain's "gray matter." Depending on their location, these AVMs may damage portions of the cerebral cortex involved with thinking, speaking, understanding language, hearing, taste, touch, or initiating and controlling voluntary movements. AVMs located on the frontal lobe close to the optic nerve or on the occipital lobe, the rear portion of the cerebrum where images are processed, may cause a variety of visual disturbances. AVMs also can form from blood vessels located deep inside the interior of the cerebrum. These AVMs may compromise the functions of three vital structures: the thalamus, which transmits nerve signals between the spinal cord and upper regions of the brain; the basal ganglia surrounding the thalamus, which coordinate complex movements; and the hippocampus, which plays a major role in memory. AVMs can affect other parts of the brain besides the cerebrum, including the hindbrain and the brainstem.

Besides AVMs, three other main types of vascular lesion can arise in the brain or spinal cord: cavernous malformations, capillary telangiectases, and venous malformations. These lesions may form virtually anywhere within the central nervous system, but unlike AVMs, they are not caused by high-velocity blood flow from arteries into veins. In contrast, cavernous malformations, telangiectases, and venous malformations are all low-flow lesions. Instead of a combination of arteries and veins, each one involves only one type of blood vessel. These lesions are less unstable than AVMs and do not pose the same relatively high risk of significant hemorrhage.

Thus the methods of the invention can be used to treat AVMs, and particularly AVMs located deep inside the brain. For example, in endovascular embolization the surgeon guides a catheter though the arterial network until the tip reaches the site of the AVM. The surgeon then introduces a substance that will plug the fistula, correcting the abnormal pattern of blood flow. This process is known as embolization because it causes an embolus (a blood clot) to travel through blood vessels, eventually becoming lodged in a vessel and obstructing blood flow. The materials used to create an artificial blood clot in the center of an AVM include fast-drying biologically inert glues, fibered titanium coils, and tiny balloons. In exemplary embodiments, the compositions and methods of the invention are suited for use in the method, either alon, or as an adjunct to surgery or to radiosurgery to reduce the blood flow through the AVM and make the surgery safer.

Also treated by the methods of the invention are vascular conditions such as varicose veins. Varicose veins are swollen and twisted veins that are visible just under the surface of the skin. They appear most commonly in the legs, but also can develop in other parts of the body. A number of other types of vein problems are related to varicose veins, for example telangiectasias are small clusters of blood vessels that look similar to spider veins. They are red in color and are commonly found on the upper body, including the face. They can develop during pregnancy and in people who have certain genetic disorders, viral infections, and other medical conditions (such as liver disease). The methods of the invention can be used, for example, to ablate the damaged varicose vein.

The methods of the invention can be used to treat hemorrhage in a subject. Hemorrhage is the medical term for bleeding, and means escape of blood to extravascular space. An intracerebral hemorrhage is bleeding in the brain caused by the rupture of a blood vessel within the head. Internal bleeding can occur in any part of the brain. Bleeding in the brain irritates the brain tissues, causing swelling (cerebral edema). The blood may collect into a mass (hematoma). Both cerebral edema and the presence of a hematoma within the brain put increasing pressure on the brain tissues and eventually destroy them. Deep intracerebral hemorrhage is a type of stroke caused by bleeding within the deep structures of the brain (thalamus, basal ganglia, pons, and cerebellum). Lobar intracerebral hemorrhage is bleeding in the largest part of the brain called the cerebrum. Lobar intracerebral hemorrhage (ICH) may be caused by traumatic brain injury or blood vessel problems, such as aneurysm, arteriovenous malformation, or angioma, a type of blood vessel tumor.

Also treated by the methods of the invention are vascular occlusions. A vascular occlusion is blockage of a blood vessel. Blockage of a blood vessel, in some aspects, can be by treatment with an alginate biomaterial. In exemplary embodiments, the vascular occlusion is an embolism. An embolism can be a pulmonary embolism or an arterial embolism. A pulmonary embolism is a sudden blockage in a lung artery. In general, a pulmonary embolism is usually due to a blood clot that traveled to the lung from the leg. A clot that forms in one part of the body and travels in the bloodstream to another part of the body is called an embolus. The type of clot that is likely to cause a pulmonary embolism originates in the veins deep in your muscles. This condition is called deep vein thrombosis (DVT). DVT usually occurs in your leg or pelvis veins, although less commonly it can also sometimes occur in your arm veins. Arterial embolism is a sudden interruption of blood flow to an organ or body part due to a clot (embolus). Arterial emboli often occur in the legs and feet. Some may occur in the brain, causing a stroke, or the heart, causing a heart attack. Less common sites include the kidneys, intestines, and the eyes.

In exemplary methods of the invention, emboli are due to the vascular migration of alginate biomaterials.

In exemplary embodiments, vascular or non-vascular conditions are selected from the group consisting of: arteriovenous malformation, neurovascular lesions, telangiectasias, varicose veins, inflammatory lesions, hemorrhage, occlusion, embolism, neoplastic growth, venous disease, and phlebitis.

In certain preferred embodiments, EmboGel can be used to treat vascular leaks, for example endoleaks. Vascular leakage, in particular Endoleak, is a major complication and its persistence following endovascular aortic aneurysm repair indicates a failure of the procedure. Its detection and treatment is therefore of primary importance, since endoleak can be associated with pressurization (increase in pressure) of the sac, resulting in expansion and rupture of the aneurysm. A thick liquid embolic agent that offers some degree of control could be of value in endoleak embolization, as it is highly biocompatible and allows for controlled hardening, remaining a liquid until it is in the presence of a divalent cation such as calcium or barium. Liquid alginate embolic agents, such as EmboGel, can be used to quickly and safely embolize endoleaks. Specifically, EmboGel can be used for the treatment of Type II endoleaks in patients with Abdominal Aortic Aneurism (AAA).

Also treated by the methods of the invention are bone related diseases or disorders. For example, in preferred embodiments, EmboGel can be impregnated with osteogenic factors or cells into vertebrae for the treatment of osteoporosis. Osteoporosis is disease that makes bones weak and more likely to break. Anyone can develop osteoporosis, but it is more common in older women. As many as half of women and a quarter of men older than 50 will break a bone due to osteoporosis. Risk factors include, but are not limited to, old age, low body weight or body mass index, family history of osteoporosis, low bone mass, and certain medications.

In a preferred embodiment for treatment of osteporosis, EmboGel is first be seeded with a patient's own mesenchymal stem cells (MSCs). A small sample of marrow can then be harvested from a patient and the MSC population is then be selected and expanded and then differentiated into osteoblasts. The differentiation of the MSCs into the osteogenic lineage is achieved by incubating cells with factors such as dexamethasone, ascorbic acid and beta-glycerophosphate.

The present invention relates in certain embodiments to a method for treating a subject suffering from a neoplastic growth, wherein the subject has previously received treatment with an alginate based biomaterial for the neoplastic growth, the method comprising the step of administering to the subject a composition comprising alginate lyase, and thereby treating the subject. In certain embodiments, the composition may further comprise a divalent metal chelator.

In exemplary embodiments of the methods, the alginate based biomaterial comprises one or more anti-cancer agents. The anti-cancer agent can be a therapeutic. Further, the anti-cancer agent can be selected from, but not limited to, any of the following: abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvin-caleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

A neoplastic growth can be any disease that is caused by or results in inappropriately high levels of cell division, inappropriately low levels of apoptosis, or both. For example, cancer is an example of a neoplasia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma).

In a further embodiment the methods of the invention are used to embolize the tumors. The embolization of tumors is often limited by pulmonary shunts. With dissolvable alginate biomaterial, embolization would be possible in patients with unacceptable shunts.

In an alternative approach, the invention can be used for thermal ablation of tumors. Accordingly, the present invention relates to the targeted intratumoral delivery of EmboGel containing iron oxides in conjunction with apparatus for creating an alternating magnetic field for thermal ablation. Thermal ablation (or radiofrequency thermal ablation) relates to heating tumors so hot that the tumor cells die. In the procedure, the tumors are located with ultrasound, computed tomography (CT), or magnetic resonance (MR) imaging devices. Then, essentially the patient is turned into an electrical circuit by placing grounding pads on the thighs. A small needle-electrode with an insulated shaft and an uninsulated distal tip is inserted through the skin and directly into the tumor. Ionic vibration at the needle tip leads to frictional heat. After 10 to 30 minutes of contact with the tumor, the radiofrequency energy kills a sphere of cancer cells, often approximately 2.5- to 5-cm in size. The dead cells are not removed, but become scar tissue and eventually shrink. RFA continues to play a time-tested, major role in the treatment of patients with painful osteoid osteomas in the bone and heart arrhythmias. In addition, RFA has been used to treat painful trigeminal neuralgia for 25 years. Today, the mainstream applications of RFA are increasing. In particular, this minimally invasive, percutaneous technique is showing promise as a treatment option for patients with primary or metastatic liver cancer. More information of thermal ablation is readily available to the public on the World Wide Web, for example at clinicalcenter.nih.gov/drd/tumortherapy.html.

Thermochemical ablation and thermal ablation alone can be employed as a treatment for an endless number of well circumscribed malignancies as described above, and variety of locations including, but not limited to, brain, liver, breast, ovaries, prostate, stomach, colon, pancreas, cervix, uterus, lungs, bladder, and skin. In addition, thermochemical ablation or thermal ablation may be employed to selectively kill non-malignant tissue as in the case of cardiac ablation. In particular for cardiac thermochemical ablation, EmboGel or EmboCaps containing cardiotoxic compounds either directly in the alginate layer or incorporated in liposomes may be preferable. Cardiotoxic compounds include but are not limited to mitomycin A, mitomycin C, doxorubicin, and anthracyclines. For this particular application, to treat Atrial fibrillation and atrial flutter, AV Nodal reentry tachycardia (AVNRT), Accessory Pathways, Ventricular Tachycardia treatment would involve the process of first delivering the EmboGel or EmboCaps through direct percutaneous injection or via microcatheter or microneedle to the appropriate cardiac location. Once the EmboGel or EmboCaps are in place, an AMF generator would be applied in the case of iron oxide containing Embogel or EmboCaps to cause locoregional heating. In the case of gold containing EmboGel or EmboCaps, high field focused ultrasound or laser excitement can be employed after delivery of EmboGel or EmboCaps to the targeted location to cause particle heating.

In addition to cancer ablation, and cardiac ablation, such techniques may be employed to deliver local heating or local heating/drug release in any malignant or non-malignant tissue in the body.

In addition to providing MR detectability, iron oxides can be employed for thermal ablation therapy. Specifically, when exposed to an alternating magnetic field (AMF), iron oxides in chemspheres heat. Non-drug loaded EmboGel or EmboCaps can be utilized for thermal ablation after particle delivery. Drug-loaded EmboGel/EmboCaps can be utilized to simultaneously release drug while heating nearby cells. This thermalchemical ablation strategy may enable greater tumor kill than a purely chemical or thermal approach alone.

The potential of hyperthermia and thermal ablation in cancer therapy has been well noted. Temperatures between 42° C. and 46° C. lead to inactivation of normal cellular processes, whereas above 46° C., extensive necrosis occurs. However, the inability to deposit effective doses of heat in tumor without applying similar heat to nearby normal tissue has prevented widespread clinical use. Difficulties in predicting thermal dose, or obtaining accurate in situ measurements, have been additional problems. New technology is needed to deliver heat selectively to tumor cells and provide predictive dosimetry. Iron oxide loaded chemspheres may prove optimal for such an application.

Particle heat output, or specific absorbtion rate (SAR), is a function of AMF field amplitude. In accordance with previous reports the lowest AMF amplitude (Oe) and highest duty ("on" time) combination—that is, 700 Oe (56 kA/m) and 90% duty—that was tested delivered safely the highest calculated total heat delivered (THD) and was associated with the greatest therapeutic effect on the tumors. However, high amplitudes at this frequency also deposit more nonspecific heat to normal tissues from increased eddy current production. To prevent overheating in normal tissues, the duty must be reduced at these higher amplitudes, providing greater "off" time between pulses for heat to dissipate. By contrast, lower-amplitude AMF can be sustained with little "off" time without compromising safety as the nonspecific heat that is generated in normal tissue does not challenge normal mechanisms that dissipate heat. Consequently, the THD to the tumor can be safety enhanced because the particles generate heat for a greater percentage of the total treatment time despite the decreased SAR. The result is a greater net heat deposited to the tumor and less heat deposited to surrounding tissues.

The present invention relates in exemplary embodiments to a method for the selective dissolution of an occlusion in a subject, wherein the subject has received treatment with an alginate based biomaterial, the method comprising the steps of administering to the subject an alginate based biomaterial to a targeted area, and administering to the subject a composition comprising alginate lyase to the first targeted area, and thereby providing selective dissolution of an occlusion in a subject. In certain embodiments, the composition may further comprise a divalent metal chelator.

The method of the invention is particularly useful wherein the selective dissolution of an occlusion occurs in a vessel not targeted for treatment. For instance, in some cases alginate biomaterial has been found to protrude out of the neck of the aneurysm and migrate into the parent artery during injection, a situation that carries a high risk of major complication such as vessel occlusion and stroke. Similar complications may result from the use of alginate in other therapeutic indications, such as in inadvertent obliteration of a normal cerebral artery during the embolization of a vascular malformation. Administration of alginate lyase and the divalent metal chelator according to the methods of the invention are useful in eliminating alginate biomaterial in unwanted locations. In exemplary embodiments, administration of the alginate lyase and the divalent metal chelator occurs after occlusion, for example immediately after the unwanted occlusion, 5 minutes, 10 minutes, 30 minutes, 1 hour, 2 hours, 5 hours, 10 hours, 15 hours, 24 hours, 48 hours, or more.

In particular embodiments, it is preferable to use bland particles, those that do not contain any toxic agent, so non-targeted particles can be dissolved without the non-targeted release of agent. Alternatively if a toxic agent is used it is safer if the agent becomes activated in some way by, for example, ultraviolet (UV) light, or ultrasound (US) rupture. In the event of non-targeted delivery, the alginate capsules can be lysed, and the non-activated agent can clear the system before activation of the targeted agent.

The present invention relates in other embodiments to a method of selectively delivering a therapeutic agent to a targeted vessel. Delivery of the therapeutic agent is achieved in a highly selective manner through the use of an alginate based biomaterial to occlude the vessels in the area where the agent is not desirably delivered, and leaving non-occluded vessels free for agent delivery in the area of treatment. Further, an alginate lyase composition, or any composition to dissolve the alginate biomaterial, can be used at the end of treatment, to dissolve the occluded vessel. Thus, the invention relates to the selective delivery of a therapeutic agent to a targeted non-occluded vessel, wherein the subject has received treatment with an alginate based biomaterial, the method comprising the steps of administering to the subject an alginate based biomaterial to a targeted area, and administering a therapeutic agent to the targeted non-occluded vessel, and administering to the subject a composition comprising alginate lyase to the targeted area of the first step of the method, and thereby providing selective delivery of therapeutic agent to a non-occluded vessel. In certain embodiments, the composition may further comprise a divalent metal chelator. The methods of the invention further comprise administering to the subject a composition comprising alginate lyase occurs after occlusion. In certain embodiments, the composition may further comprise a divalent metal chelator. Administering the composition that dissolves the occlusion, for example alginate lyase, occurs any time after occlusion, for example 5 minutes, 15 minutes, 30 minutes, 1 hour, 2 hours, 5 hours, 10 hours, 24 hours, or more.

Exemplary embodiments of the method include use of the alginate biomaterial for reversible blockage of nasal passage in case of epistaxis, or in the fallopian tubes as a reversible contraceptive or potentially useful for in vitro fertilization or other nonvascular conduit in body, for example the bronchi.

Water-soluble drugs can easily be dissolved in alginate and become trapped in the resulting matrix, once the sample is gelled, allowing for drug-enhanced embolization, a characteristic further enhanced by the fact that alginate gels have a porous structure that allows for controlled drug diffusion (future applications include combined delivery of chemotherapeutic or angioactive agents). The main advance offered by alginate based biomaterials, however, is that alginate based biomaterials can be selectively dissolved with the alginate lyase composition. If the embolic agent is delivered in a non-targeted structure, for example a blood vessel feeding normal tissue, it can be broken down into biocompatible liquid components again. Any agent can be delivered in this manner. Exemplary agents include, but are not limited to, chemotherapeutic agents, anti-inflammatory agents, antimicrobial agents, hormonal therapy agents, metalloproteinase inhibitors, sclerosing agents, angio-active agents, plasmids for gene therapy, adenoviral vectors for gene therapy, RNAi, antisense, lentivirus, microbubbles, toxins (ricin toxin, conotoxin, botulin toxin a-g, diptheria toxin, cholera toxin, tetanus toxin, shiga-like toxin antibiotics, vaccines, photodynamic agents, alpha emitters, beta emitters, antibodies, hormones, recombinant glycoproteins and analgesics.

The present invention relates in certain embodiments to a method for the selective control of bulking or remodeling in a subject, the method comprising the steps of administering to the subject an alginate based biomaterial to a targeted area, and administering to the subject a composition comprising alginate lyase to the targeted area of the first step, wherein administration of the composition comprising alginate lyase provides selective control of bulking or remodeling in a subject. In certain embodiments, the composition may further comprise a divalent metal chelator. For certain applications the use of a self-polymerizing alginate is preferable.

For example, a self-polymerizing agent is advantageously used in for cosmetic bulking procedures. A self-gelling alginate as is described in US publication 2006/0159823, incorporated by reference in its entirety herein. Accordingly, a self-gelling alginate can be modified to contain an optical agent to assess localization. For example, the FDA approved optical agent inodcyanine green has been shown to be used at a concentration of 0.005% to assess localization after injection with infared. Gels can be made by mixing a solution of sodium alginate (Protanal SF 120) and a calcium alginate dispersion (Protaweld TX 120). The amount of calcium alginate is in certain preferred embodiments 1.5% and the amount of sodium alginate is in certain preferred embodiments 1%. The solution and dispersion are mixed and 5 mL of the gel injected into a 50 mL conical tube. The sample was left to gel for 1 hour. After complete hardening 0.5 mL of alginate lyase, as described herein, was added to the sample causing complete dissolution.

The use of EmboClear is not limited to this one formulation but could be used with any formulation as presented in US patent 2006/0159823, incorporated by reference in its entirety herein. Further, in addition to indocyanine green, Feridex, Gold dextran50 (Nanocs), Barium sulfate solution, PFOB micelles and PFCE micelles all prepared as described above could be added up to a concentration of 20% vol/vol to the pregelled alginate and gellation will still occur. Further the contrast containing gels could be dissolved with EmboClear.

In one particular example, the method can be used to treat urinary incontinence.

In another embodiment, method is used in a subject that is undergoing plastic or reconstructive procedures. Alginate biomaterials can be used as a bulking agent for plastic and reconstructive procedures, where the combination with alginate lyase would offer the possibility of secondary remodeling and consistency adjustment.

For example, a nonporous sac can first be implanted and then filled with EmboGel. Unlike current surgical procedures, such a procedure could potentially be completed percutaneously as the sac could be placed collapsed percutaneously and then filled percutaneously post implantation with EmboGel. Such a design may be particularly attractive for breast and cheek augmentation. In the case of a microporous mesh sac, EmboGel could also be filled with therapeutic factors and act as a large depot for locoregional drug delivery.

The present invention relates in exemplary embodiments to a method for the controlled release of an agent in a subject, the method comprising the steps of administering to the subject an alginate based biomaterial comprising an agent, and administering to the subject a composition comprising alginate lyase, wherein administration of the composition comprising alginate lyase results in controlled release of the agent. In certain embodiments, the composition may further comprise a divalent metal chelator An exemplary use of the method is in treating a subject suffering from a vascular or non-vascular condition, as described above.

Any agent is suitable for use in this method. Exemplary agents include, but are not limited to, chemotherapeutic agents, anti-inflammatory agents, antimicrobial agents, hormonal therapy agents, metalloproteinase inhibitors, sclerosing agents, angio-active agents, plasmids for gene therapy, adenoviral vectors for gene therapy, RNAi, antisense, lentivirus, microbubbles, toxins, antibiotics, vaccines, photodynamic agents, and analgesics.

In particular embodiments, the therapeutic agent is a nanomaterial. In other particular embodiments, the therapeutic agent is contained within the nanomaterial. In other particular embodiments, the therapeutic agent is bound to the nanomaterial.

A nanomaterial can be, but is not limited to nanocotainers, biological nanomotors, peptide-based self-assembling materials, nanorobots, smart nanodevices as anticancer therapeutics, nanocomposite devices, nanoparticles comprised of carbohydrates, virus particles, lipids, DNA. dendrimers, microchips, drug-loaded microchips, micropumps, hyperbranched polymers, polymer brushes, nanofibers, polymeric nanotubes, nanocapsules, Biosensors, nanotubes, nanowires, chemical sensors, nanohorns, nanorods, MEMS Micro-Electro-Mechanical systems, fluorescent nanoparticles, magnetic nanoparticles, colloidal gold nanoparticles, colloidal gold biofunctionalized nanomodules, magnetic nanoparticles for magnetic guided 'tag and drag delivery', nanoparticles conjugated with biological ligands, metal nanoclusters, dendrimer nanocomposites, DNA-linked nanoparticles, nanocolloids (organosols and hydrosols), metal nanopowders (Ag, Au, Pt, Pd), metal nanoparticles and magnetic fluids, palladium nanoparticles, nanomaterials comprised of silicon, aluminum nitride, zinc oxide, platinum, titatium dioxide, silicon dioxide, silicon carbide, cobalt, carbon (graphite), aluminum oxide, cerium oxide, aluminum, gold, silver, copper, nickel. Nano-glasses, nano-ceramics, Cu alloys, Ni alloys, Zn alloys, Co alloys, Zr alloys, nobel metals, light metals, Ti, Ti—Al, Ti transition metals alloy (Fe or Ni or Cu), Mg—Ni, Fe—Cu—Nb—Si—B alloy, Fe-transition metal alloy (Co, Ni, Cr, Cu, Zr), Al-transition metal alloy (Fe, Ni, Ti, Zr), Mg, Al—Mg alloy.

In exemplary embodiments, the nanomaterial is selected from, but not limited to, microboxes, microchips, microfluidic pumps, magnetic resonance microcoil, quantum dots, antibody targeted nanomaterials, nanocontainers, and nanoboxes.

Nanomaterials can be colloidal metals. A colloidal metal includes any water-insoluble metal particle or metallic compound dispersed in liquid water. Typically, a colloid metal is a suspension of metal particles in aqueous solution. Any metal that can be made in colloidal form can be used, including gold, silver, copper, nickel, aluminum, zinc, calcium, platinum, palladium, and iron. In some cases, gold nanoparticles are used, e.g., prepared from $HAuCl_4$.

The use of gold nanoparticles is preferred in certain embodiments. Gold nanoparticles not only impart radiopacity to EmboCaps and EmboGel but also enable visualization on US. Further by use of high field focused ultrasound or laser excitement in laser photothermal therapy, the particles and surrounding hydrogel will heat. In cases in which EmboCaps or EmboGel contain heat sensitive liposomes, this will cause a burst release effect of drug from the EmboCaps and EmboGel. Further when a therapeutic factor is directly incorporated into the alginate component of EmboCaps or EmboGel, heat will increase the porosity of the hydrogel thereby increasing rate of release.

In the case of cardiac thermochemical ablation, EmboGel or EmboCaps containing cardiotoxic compounds either directly in the alginate layer or incorporated in liposomes may be preferable. Cardiotoxic compounds include, but are not limited to, mitomycin A, mitomycin C, doxorubicin, anthracyclines. For this particular application, to treat Atrial fibrillation and atrial flutter, AV Nodal reentry tachycardia (AVNRT), Accessory Pathways, Ventricular Tachycardia treatment would involve the process of first delivering the EmboGel or EmboCaps through direct percutaneous injection or via microcatheter or microneedle to the appropriate cardiac location. Once the EmboGel or EmboCaps are in place, an AMF generator would be applied in the case of iron oxide containing Embogel or EmboCaps to cause locoregional heating. In the case of gold containing EmboGel or EmboCaps, high field focused ultrasound or laser excitement can be employed after delivery of EmboGel or EmboCaps to the targeted location to cause particle heating. In addition to cancer ablation and cardiac ablation such techniques may be employed to deliver local heating or local heating/drug release in any malignant or non-malignant tissue in the body.

Nanoparticles can be any shape and can range in size from about 1 nm to about 10 nm in size, e.g., about 2 nm to about 8 nm, about 4 to about 6 nm, or about 5 nm in size. Methods for making colloidal metal nanoparticles, including gold colloidal nanoparticles from $HAuCl_4$, are known to those having ordinary skill in the art. For example, the methods described herein as well as those described elsewhere (e.g., US 2001/005581; 2003/0118657; and 2003/0053983) can be used to make nanoparticles.

A nanoparticle can have at least one agent linked to its surface. Any of the agents described herein can be linked covalently, non-covalently, or coordinately to the surface of the nanoparticle. For example, all the bonds from an agent to a nanoparticle can be covalent bonds to the surface of the nanoparticle. In some cases, some of the bonds are covalent to the surface of the nanoparticle, and some are noncovalent to the surface of the nanoparticle. In some cases, some of the bonds are covalent to the surface of the nanoparticle, and some are coordinate to the surface of the nanoparticle. In some cases, all of the bonds are noncovalent to the surface of the nanoparticle.

In certain cases, a nanoparticle can have two, three, four, five, six, or more agents linked to its surface. Typically, many molecules of an agent are linked to the surface of the nanoparticle at many locations. Accordingly, when a nanoparticle is described as having, for example, two agents linked to it, the nanoparticle has two distinct agents, each having its own unique molecular structure, linked to its surface. In some cases, one molecule of an agent can be linked to the nanoparticle via a single attachment site or via multiple attachment sites.

An agent can be linked directly or indirectly to a nanoparticle surface. For example, an agent can be linked directly to the surface of a nanoparticle or indirectly through an intervening linker. Any type of molecule can be used as a linker. For example, a linker can be an aliphatic chain including at least two carbon atoms (e.g., 3, 4, 5, 6, 7, 8, 9, 10 or more carbon atoms), and can be substituted with one or more functional groups including ketone, ether, ester, amide, alcohol, amine, urea, thiourea, sulfoxide, sulfone, sulfonamide, and disulfide functionalities. In cases where the nanoparticle includes gold, a linker can be any thiol-containing molecule. Reaction of a thiol group with the gold results in a covalent sulfide (—S—) bond. Linker design and synthesis are well known in the art. Any type of agent can be linked to a nanoparticle. For example, an agent can be a therapeutic agent that has a therapeutic effect in the body. Examples of therapeutic agents include, without limitation, anti-angiogenic agents, chemotherapeutic agents, anti-inflammatory agents, anti-bacterial agents, anti-fungal agents, growth factors, immunostimulatory agents, anti-cholinergic agents, insulin, and insulin analogs.

A therapeutic agent can be in any physical or chemical form, including an antibody, an antibody fragment, a receptor, a receptor fragment, a small-molecule, a peptide, a nucleic acid, and a peptide-nucleic acid. A therapeutic agent can function as a targeting agent in addition to functioning as a therapeutic agent. A targeting functionality can allow nanoparticles to accumulate at the target at higher concentrations than in other tissues. In general, a targeting molecule can be one member of a binding pair that exhibits affinity and specificity for a second member of a binding pair. For example, an antibody or antibody fragment therapeutic agent can target a nanoparticle to a particular region or molecule of the body (e.g., the region or molecule for which the antibody is specific) while also performing a therapeutic function.

A nanoparticle can have a diagnostic agent linked thereto. In some cases, a diagnostic agent and a therapeutic agent can both be linked to a nanoparticle. A diagnostic agent can allow the imaging of a nanoparticle in vivo. For example, a patient administered a nanoparticle having a diagnostic agent and a therapeutic agent linked thereto can be imaged once, e.g., to locate and/or stage a tumor, or at multiple time points, e.g., to monitor the efficacy of the therapeutic agent.

Any type of diagnostic agent can be linked to a nanoparticle, including, for example, an MR imaging agent, a radio-imaging agent, an X-ray imaging agent, and a near-IR imaging agent. Two or more diagnostic agents can also be linked to a nanoparticle, such as an MR imaging agent and an X-ray imaging agent, or a near-IR imaging agent and an MR imaging agent. An MR imaging agent can be a metal chelate, e.g., can include a chelating ligand and a paramagnetic metal ion coordinated thereto. Any type of chelating ligand can be used, including cyclic and acyclic chelating ligands such as DTPA, DOTA, DOTMA, DTPA-BMA, DOTAGA, and HP-DO3A. Examples of paramagnetic metal ions include, without limitation, Gd(III), Fe(III), Mn(II), Cr(III), Cu(II), Dy(III), Ho(III), Er(III), Eu(III), Tb(II), Tb(III), and Tb(IV).

In particular exemplary embodiments, the agent is contained within therapeutic liposomes. Liposomes are formed when phospholipids and their derivatives are dispersed in water. Upon dispersion in water the phospholipids form closed vesicles called "liposomes", which are characterized by lipid bilayers encapsulating an aqueous core. Various liposomes have been used as carriers for entrapped therapeutic agents, such as drugs, enzymes and genetic sequences for use in medical science, in pharmaceutical science and in biochemistry.

Examples of liposome compositions include U.S. Pat. Nos. 4,983,397; 6,476,068; 5,834,012; 5,756,069; 6,387,397; 5,534,241; 4,789,633; 4,925,661; 6,153,596; 6,057,299; 5,648,478; 6,723,338; 6,627,218; U.S. Pat. App. Publication Nos: 2003/0224037; 2004/0022842; 2001/0033860; 2003/0072794; 2003/0082228; 2003/0212031; 2003/0203865; 2004/0142025; 2004/0071768; International Patent Applications WO 00/74646; WO 96/13250; WO 98/33481; Papahadjopolulos D, Allen T M, Gbizon A, et al. "Sterically stabilized liposomes. Improvements in pharmacokinetics and antitumor therapeutic efficacy" Proc Natl Acad Sci U.S.A. (1991) 88: 11460-11464; Allen T M, Martin F J. "Advantages of liposomal delivery systems for anthracyclines" Semin Oncol (2004) 31: 5-15 (suppl 13). Weissig et al. Pharm. Res. (1998) 15: 1552-1556.

Examples of lipid compositions including targeting factors include U.S. Pat. Nos. 5,049,390; 5,780,052; 5,786,214; 6,316,024; 6,056,973; 6,245,427; 6,524,613; 6,749,863; 6,177,059; 6,530,944; U.S. Pat. App. Publication. Nos. 2004/0022842; 2003/0224037; 2003/143742; 2003/0228285; 2002/0198164; 2003/0220284; 2003/0165934; 2003/0027779; International Patent Application Nos. WO 95/33841; WO 95/19434; WO 2001037807; WO 96/33698; WO 2001/49266; WO 9940789; WO 9925320; WO 9104014; WO 92/07959; EP 1369132; JP 2001002592; Iinuma H, Maruyama K, et al., "Intracellular targeting therapy of cisplatin-encapsulated transferrin-polyethylene glycol liposome on peritoneal dissemination of gastric cancer" Int J Cancer (2002) 99 130-137; Ishida 0, Maruyama K, Tanahashi H, Iwatsuru M, Sasaki K, et al., "Liposomes bearing polyethylene glycol-coupled transferrin with intracellular targeting property to the solid tumors in vivo." Pharmaceutical Research (2001) 18: 1042-1048; Holmberg et al., Biochem. Biophys. Res. Comm. (1989) 165(3): 1272-1278; Nam et al., J. Biochem. Mol. Biol. (1998) 31(1): 95-100; Nag et al., J. Drug Target. (1999) 6(6): 427-438.

A variety of drugs or agents may be included in the lipid-containing compositions of the present invention, for example, a compound or a gene. In certain embodiments, the drug may be an anticancer agent, for example, an anticancer agent suitable for encapsulation in a liposome. The amount of drug to be included in the lipid-containing compositions, and formulations thereof, as described herein can be readily determined by the skilled artisan in view of the teaching herein provided and depending on the drug selected and the use intended for the composition or formulation, taking into account factors specific to both the drug and the individual to be treated, as described further herein. In certain embodiments, the drug may be a nucleic acid, for example, but not limited to, antisense oligonucleotides, ribozymes, etc.

The lipid-containing compositions described herein can be modified with targeting factors and directed to a particular target cell. The term "targeting factor" refers to a moiety that can bind to a receptor or a surface antigen present on the surface of a target cell. In certain embodiments, the targeting factors are directed to cell surface receptors on a particular target cell. The targeting factor is often a protein or a peptide that can be attached to a lipid component of the lipid-containing composition. Most effectively, targeting factors are selected such that the targeted receptor or antigen is present only on cells that are targeted for the delivery of the drug or labeled compound (e.g., pathogenic cells) and not present on healthy cells. Alternatively, a greater number of receptors or antigens are expressed on the target cells (e.g., pathogenic or diseased cells) compared to non-targeted (e.g., healthy) cells. Preferably, the receptor or antigen that binds the targeting factor is either not present or present in low numbers on healthy cells such that binding with the targeting factor does not occur with frequency. In other words, targeting factors need to selectively deliver the liposomes as described herein (including encapsulated drug) to the targeted cells (e.g., pathogenic, unhealthy, etc.). Selective delivery of the encapsulated drug to the targeted cells thus reduces the occurrence of adverse effects due to the effect of encapsulated drug or labeled compound on non-targeted (e.g., healthy) cells, thereby also reducing the adverse effects experienced by the individual to whom the composition, or formulation thereof, is administered. Exemplary targeting factors include, but are not limited to, transferrin, folic acid, folate, hyaluronic acid, sugar chains (e.g., galactose, mannose, etc.), fragments of monoclonal antibodies, asialoglycoprotein, etc., as well as other targeting factors known to the skilled artisan. In particular embodiments, the targeting factor is a protein or peptide directed to a cell surface receptor (e.g., transferrin, folate, folic acid, asialoglycoprotein, etc.). In other embodiments, the targeting factor is directed to an antigen (e.g., fragments of monoclonal antibodies (e.g., Fab, Fab', F(ab').sub.2, Fc, etc.)). It is not intended that targeting factors include intact or whole monoclonal antibodies. The term "whole antibody" or "intact antibody," and cognates thereof, as used herein generally refer to antibody IgG of immune globulin. A fragment of a monoclonal antibody generally refers to a decomposition product of the monoclonal antibody, for example, a fragment obtained by using protease digestion, such as pepsin, etc. In certain embodiments, the targeting factor is not directed to an antigen (e.g., is not a fragment of a monoclonal antibody, e.g., Fab, Fab', F (ab').sub.2, Fc, etc).

In exemplary embodiments, the therapeutic liposomes are coated with protein. The protein can be, but is not limited to, antibodies, receptors, and cell surface markers.

It is desirable, according to the invention, to further combine the agent with a second agent selected from, but not limited to, contrast agents, quantum dots, antibodies, liposomes, and nanoboxes. The agent, in exemplary embodiments, is a cell secreting a therapeutic factor. The cell secreting factor can be, but is not limited to, any of the following: autogenic or allogenic fibroblasts, endothelial cells, transgenic cells, mesenchymal stem cells, embryonic stem cells, extraembryonic stem cells, embryonic germ cells, cardiac stem cells, umbilical stem cells, cardiac stem cells, all pluripotent and multipotent stem cell sources, pancreatic islet cells, hepatocytes, skin cells, intestinal stem cells, myoblasts, endothelial cells, cardiac myoblasts, dendritic cell, autologous tumor cells (method of sensitization and potential vaccine delivery), Monocyte derived activated killers, Natural Killer T Cells, patients own cancer cells with liposomal Il-2, cultured chondrocytes, hematopoietic stem cells, sertoli cells, xenogenic cell sources of all listed above, skin cells, adipocytes, skin-derived stem cells, neural stem cells, glial progenitor cells, oligodendrocyte and oligo precursors, fat stem cells, other stem cells sources such as from amniotic fluid, baby teeth, bone marrow cells, cord and placental blood, fat tissue, fetal cells, unfertilized ova, pancreas, breast.

Autogenic or allogenic fibroblasts, endothelial cells or transgenic cells secreting therapeutic factors may be added to the alginate prior to delivery in order to create a bioactive tissue scaffold that may provide tissue regrowth from the inside out.

According to exemplary embodiments of the invention, the alginate based biomaterial is linked to an agent. The agent can be, but is not limited to tissue scaffold, microcapsules or wound dressings.

The present invention relates in certain embodiments to a method for the controlled release of a label in a subject, the method comprising the steps of administering to the subject an alginate based biomaterial comprising a label, and administering to the subject a composition comprising alginate lyase, wherein administration of the composition comprising alginate lyase results in controlled release of the label. In certain embodiments, the composition may further comprise a divalent metal chelator.

An exemplary use of the method of the invention is for diagnostic purposes. In one example, the method is used for selected angiography of a labeled vessel.

The label used in the method of the invention can be any label that is suitable for incorporation in to an alginate based biomaterial, and for use in, for example, diagnostic purposes. The label can be selected from the group that consists of, but is not limited to, radiolabel, fluorescent label, tissue dye. The label can be contained within a micelle. The radiolabel can be, but is not limited to any one of carbon 14, carbon 14 intermediates, tritium-labeled, iodine 125, and antibody targeted radioisotopes. The fluorescent label can be, but is not limited to, cadmium selenide, quantum dots, fluorophores and their amine-reactive derivatives, thiol-reactive probes, reagents for modifying groups other than thiols or amines, biotin derivatives, haptens, crosslinking reagents, and photoactivatable reagents. The tissue dye can be, but is not limited to, methylene blue.

In exemplary embodiments, the label is contained within a liposome. A variety of labeled compounds may be included in the lipid-containing compositions of the present invention. The labeled compound may be an agent useful in carrying out in vivo diagnostic procedures. As with the incorporation of agents as described herein, the amount of labeled compound to be included in the lipid-containing compositions, and formulations thereof, as described herein can be readily determined by the skilled artisan in view of the teaching herein provided and depending on the labeled compound selected and the use intended for the composition or formulation, taking into account factors specific to both the labeled compound and the individual to be diagnosed, as described further herein. Exemplary labeled compounds include, for example, materials comprising radioisotopes (e.g., $^{3}H$, $^{4}C$, $^{67}Ga$, $^{111}In$, $^{125}I$, $^{125}I$,), material comprising fluorescent moieties (e.g., fluorescein, fluorescein isothiocyanate, etc.), material comprising enzyme (e.g., peroxidase, alkaline phoshohatase, etc.), as well as additional labeled compounds known to those of skill in the art. As will be appreciated by the skilled artisan, the selection of the labeled compound and methods used in diagnosis will depend upon the organ (e.g., liver, pancreas, prostate, etc.), tissue (e.g., malignant or non-malignant or tissue type (e.g., brain, cardiovascular, etc.) to be investigated.

The present invention relates in other embodiments to a method for the controlled release of a label to mark lesions for radiosurgery, the method comprising the steps of: administering to the subject administering to the subject an alginate based biomaterial linked to a label, and administering to the subject a composition comprising alginate lyase, wherein administration of the composition comprising alginate lyase results in controlled release of the label and marking of the lesion for radiosurgery. In certain embodiments, the composition may further comprise a divalent metal chelator.

The label can be selected from the group that consists of, but is not limited to, radiolabel, fluorescent label, tissue dye. The label can be contained within a micelle. The radiolabel can be, but is not limited to any one of carbon 14, carbon 14 intermediates, tritium-labeled, iodine 125, and antibody targeted radioisotopes. The fluorescent label can be, but is not limited to, cadmium selenide, quantum dots, fluorophores and their amine-reactive derivatives, thiol-reactive probes, reagents for modifying groups other than thiols or amines, biotin derivatives, haptens, crosslinking reagents, and photoactivatable reagents. The tissue dye can be, but is not limited to, methylene blue. In exemplary embodiments, the label is contained within a liposome.

The present invention relates in certain embodiments to a method for the controlled release of a contrast agent in a subject, the method comprising the steps of administering to the subject an alginate based biomaterial comprising a contrast agent, and administering to the subject a composition comprising alginate lyase, wherein administration of the composition comprising alginate lyase results in controlled release of the contrast agent. In certain embodiments, the composition may further comprise a divalent metal chelator.

In preferred embodiments, the contrast agent can be, but is not limited to, any of a magnetic resonance contrast agents, radioopaque contrast agents, ultrasound contrast agents, and Nuclear Medicine Imaging contrast agents.

Contrast agents can be, but are not limited to, optical agents, PET probe, ultrasound contrast agent, Radioisotopes, magnetic resonance image contrast agent, radioopaque contrast agent for visualization on X-ray modalities, for example DSA, Fluoroscopy, CT, X-Ray.

The present invention provides in certain embodiments a method for selective dissolution of a biocompatible material, wherein the material consists only in part of alginate and therefore partially dissolves when treated with alginate lyase. The present invention relates in certain embodiments to a method for the selective dissolution of a biocompatible material in a subject, the method comprising the steps of administering to the subject an alginate loaded biocompatible material to a targeted area, and administering to the subject a composition comprising alginate lyase to the targeted area of the first step, wherein administration of the composition comprising alginate lyase provides selective dissolution of the biocompatible material in the subject. The method provides a biocompatible material, wherein a portion of the biocompatible material does not dissolve when treated with composition or agent that dissolves an alginate biomaterial, for example alginate lyase. In certain embodiments, the composition may further comprise a divalent metal chelator.

The targeted area according to the method of the invention is any area that is in need of a biocompatible material. The targeted area could be a target organ in need of drug treatment, a Composite for Artificial Muscle, Artificial Hearts and Pacemakers, Tissue-Engineered Human Heart Tissue, Artificial Pancreas, Artificial Liver, Artificial Blood Vessel, Artificial Nerves, drug/gene delivery stent, nerve graft, The targeted area is selected from the group consisting of: liver, pancreas, thyroid, heart, peripheral nerve scaffold, breast, bladder, cartilage, bone, tendon, ligament, blood vessel, and spinal cord.

Alginate can be incorporated in to any material that is transplantable in to the human body. Alginate, for example, may be a component of a polymer based stent or an artificial valve. Administration of alginate lyase could cause partial breakdown of the stent, and release of an agent, such as s drug or gene. The biocompatible material can be, but is not limited to: polyvinyl alcohol, sodium polyacrylate, acrylate polymers, Hyaluronase Polymers, collagen membrane, Porous HA/TCP ceramic composite, Hydroxyapatite bone cement, PVP/PMMA, tricalcium phosphate, Hydroxyapatite coated collagen fibres, calcium sulphate, Hydroxyapatite (HAp), Phosphorylcholine (PC), silicone, ultrahigh molecular weight polyethylene, polyethylene, acrylic, nylon, Polyurethane, Polypropylene, poly(methyl methacrylate), Teflon, Dacron, acetal, polyester, silicone-collagen composite, polyaledehyde, poly(vinyl chloride), silicone-acrylate, poly(tetrafluoroethylene), hydroxyethyl methacrylate (HEMA), poly(methyl methacrylate) (PMMA), poly(glycolide lactide), poly(glycolic acid), tetrafluoroethylene, hexafluoropropylene, poly(glycolic acid), poly(lactic acid), desaminotyrosyl-tyrosine ethyl ester, polydioxanone, fibrin, gelatin, hyaluronan, tricalcium phosphate, polyglycolide (PGA), polycaprolactone, poly (lactide-co-glycolide), polyhydroxybutyrate, polyhydroxyvalerate, trimethylene carbonate, polyanhydrides, polyorthoesters, poly(vinyl alcohol), poly(N-vinyl 2-pyrrolidone), poly(ethylene glycol), poly(hydroxyethylmethacrylate), n-vinyl-2-pyrrolidone, methacrylic acid, methyl methacrylate, and maleic anhydride, polycaprolactone, poly(amino acids) ie poly(L-lysine), poly(1-ornithine), poly(glutamic acid), polycyanoacrylates, polyphosphazenes, poly(lactic acid), poly(glycolic acid), crown ethers, cyclodextrins, cyclophanes, ethylene glycol, Methylacrylate, Para-xylylene, Biodegradable Copolymers, Copolymer Surface Coatings, Starch Polymers, Polylactic Acid, Cellophane, Tyrosine Polycarbonates Lactide and Glycolide Polymers, Collagen, PTFE, silicone, Keratin-Based Materials, Fibrous Composites—Carbon Fiber and Particles, Polymer Composites, Artificial/Natural Material Composites, Glass-Ceramic/Metal Composites, Glass-Ceramic/Nonmetal Composites, Dental Composites, Ormocer, hydrogels, timed-release foams, and polymeric carriers.

Hydrogels have also been used to form expanding, swelling stents, and as space-fillers for treatment of vascular aneurysms in a manner similar to other types of mechanical, embolus generating vasoocclusive devices. In one such procedure, an aneurysm is treated by inserting a stent formed of a hydrogel material into the vessel, and then hydrating and expanding the hydrogel material until the stent occludes the vascular wall, sealing it from the parent vessel. Biodegradable hydrogels have also been used as controlled-release carriers for biologically active materials such as hormones, enzymes, antibiotics, antineoplastic agents, and cell suspensions. U.S. Pat. No. 6,113,629 relates to the use of hydrogels for use in occluding aneurysms, and is incorporated herein by reference in its entirety.

In certain preferred embodiments, the compositions of the invention could effectively dissolve the hydrogel component of the commercially available alginate dressings, for example, but not limited to ALGISITE M, SEASORB, CONTREET-H, INVACARE Calcium Alginate Wound Dressing, NUDERM Alginate Wound Dressing, CURASORB Calcium Alginate Dressing, TEGAGEN HG Alginate Dressing, KALTOSTAT Alginate Dressing, ALGISITE M Calcium Alginate Dressing, RESTORE Calcium Alginate Dressing, and RESTORE Silver Calcium Alginate.

The present invention relates in certain embodiments to a method for the selective dissolution of a wound dressing in a subject. The method comprises the steps of administering an alginate based wound dressing to a wound; and waiting a period of time, for example waiting a time of 1 day, 2 days, 3 days, 4 days, 5 days, 6 days, 7 days, 10 days, 12 days, 14 days, 21 days, 15 days, 28 days, 30 days, 35 days, 40 days, or more days and then administering a composition comprising alginate lyase and a divalent metal chelator to the wound and repeating the steps of administering the alginate based wound dressing, waiting a period of time, and then administering a composition comprising alginate lyase to the wound, until the wound is healed, and wherein administration of the composition comprising alginate lyase provides selective dissolution of the wound dressing in the subject. In certain embodiments, the composition may further comprise a divalent metal chelator.

Calcium alginates have long been known for their ability to form fibers or nonwoven materials. These have been used primarily as swabs or dressings for medical, surgical or other purposes, such as described in European Patent Specification, EP 0721355 B1, entitled "Alginate Wound Dressings, which is incorporated herein by reference in its entirety. Supplied in the form of nonwoven wound dressings for the treatment of exudating wounds, the calcium alginate dressing is said to encourage the formation of controlled ion-active gel over the wound site which reacts with the sodium ions in the exudate. Examples of exudative wounds include pressure ulcers, venous stasis ulcers, diabetic ulcers, arterial ulcers, second degree burns and skin graft donor sites. The alginate based wound dressing can be a solid dressing, more specifically a solid wound dressing comprised of an alginate based biomaterial, capable of delivering an effective wound-healing agent. U.S. Pat. No. 7,112,320 describes solid wound dressings, including solid wound dressings based on calcium alginate, capable of delivering an effective wound healing amount of fibronectin to a wound site, and is incorporated herein by reference. In certain embodiment, the alginate based wound dressing further comprises one or more therapeutic agents. The therapeutic agent can be is selected from, but is not limited to, an antibiotic, such as cephalosporins, macrolides, penicillins, quinolones, sulfonamides, tetracycline, aminoglycosides, lincomycin, chloramphenicol, glycopeptides, monobactams, carbapenems, carbacephems, metronidazole, antitubercular, antileprotics, oxazolidinones, ketolides, an analgesic, an antifungal, an antiviral, enzymes, vaccines, gene delivery vectors, such as liposomes, cationic lipids, lentiviral vectors, antibodies, hormone and recombinant glycoproteins.

The method is particularly applicable to burn victims, providing wound dressings that would not have to be removed, but rather dissolved away. The method of the selective dissolution of a wound dressing mitigates the pain and skin damage that is occurs with bandage removal.

Tissue Scaffolds and Dressings

In certain embodiments, selectively dissolvable alginate dressings can be dissolved with EmboClear.

An alginate dressing, termed Smart Skin, is a dressing for split-thickness skin graft. Similar to ALLEVYN (Smith & Nephew), in a certain embodiment Smart Skin has a hydrophilic inner layer consisting of a collagen, calcium alginate mixture. Applied to the hydrophilic inner layer is an outer polyurethane waterproof film layer that prevents bacterial contamination and maintains a moist wound environment. Smart Skin provides a unique advantage over Allevyn as the inner hydrogel layer can be selectively dissolved with EmboClear. This overcomes the major drawback of Allevyn, namely its propensity to strongly adhere to the wound bed causing mechanical trauma to the newly formed delicate epithelium when the dressing is changed.

Smart Skin can be impregnated with nanocrystalline silver particles (10 nm from Nanocs) by directly dissolving the alginate at a concentration of 2% w/v in a 0.01% Ag aqueous solution prior to polymerization. In certain embodiments larger silver nanoparticles are preferable (20-50 nm Nanocs). Additionally, collagen, hyaluronic acid or an alternate biodegradeable biomaterial may be added to the silver alginate solution prior to polymerization with calcium or an alternate divalent cation. In addition to directly incorporating silver nanoparticles in the inner alginate layer, in an alternate formulation the outer layer can consist of a silver-coated high-density polyethelene mesh similar to Acticoat (Smith and Nephew).

Alternate compound that can be incorporated into the alginate matrix of Smart Skin to promote keratinocyte growth include M4 agonists, M3 antagonists, basic fibroblast growth factor (bFGF), keratinocyte growth factor (KGF), WNTs, Keratinocyte growth factor-2 (KGF-2). These agents may be directly incorporated into the alginate layer prior to polymerization or in certain embodiments may first be entrapped in liposomes that are then added to the liquid alginate layer prior to polymerization. This unique combination of liposome impregnated hydrogel scaffold ensures a slow release of hydrophilic compounds as demonstrated by the release of doxorubicin from liposomes in EmboCaps previously described in this patent.

In alternate embodiments, alginate can act as a component of a full-thickness skin scaffold. In certain embodiments in which alginate is combined with other biomaterials such as collagen, hyaluronic acid or PEGDA, EmboClear can be added to selectively dissolve the alginate component of the scaffold. This potentially would enable ease of removal of an infected tissue scaffold or alternatively would give the clinician selective control over the porosity of the scaffold thereby facilitating tissue ingrowth. In addition, the skin scaffold can be seeded with a number of cell sources. In another embodiment, the agent is a cell secreting a therapeutic factor. In another particular embodiment of the method, the cell secreting a therapeutic factor is selected from the group consisting of: autogenic or allogenic fibroblasts, endothelial cells, transgenic cells, mesenchymal stem cells, embryonic stem cells, extraembryonic stem cells, embryonic germ cells, umbilical stem cells, pluripotent and multipotent stem cells, endothelial cells, dendritic cell, hematopoietic stem cells, sertoli cells, xenogenic cell sources of all listed above, skin cells, adipocytes, skin-derived stem cells, neural stem cells, glial progenitor cells, oligodendrocyte precursors, oligo precursors, fat stem cells, other stem cells sources such as from amniotic fluid, baby teeth, bone marrow cells, cord blood, placental blood, fat tissue, fetal cells and breast.

EmboCaps

Alginate based biomaterials can form EmboCaps. EmboCaps are in a small spherical form, and are polymerized prior to injecting in the body. EmboCaps are particularly attractive for intravascular delivery strategies as microcapsules can be used as embolic agents to create a reversible stasis thereby allowing a high payload of therapeutic agent to be delivered to a relatively well-targeted area. EmboCaps can be potentially used as transport vectors for the delivery and/or controlled release of a large array of bioactive agents, such as chemotherapeutic, anti-inflammatory, or antimicrobial drugs, hormonal therapy agents, gene therapy vectors, or radioisotopes for radiotherapy.

The rate of diffusion of bioactive agent from alginate capsules can be altered by modifying the porosity of the matrix. Alginate can be readily coated with a rate-controlling, size-selective membrane of cationic polypeptides such as poly-1-lysine and poly-1-ornithine. The properties of the coating can be controlled by varying the parameters of the coating process such as the coating material, its molecular weight, the concentration of the coating solution, and the coating time, allowing the design of coatings with different molecular weight cut offs and with different release rates. In addition to diffusion controlled-strategies the release of bioactive agent from hydrogels can be erosion-controlled. By adding biodegradeable components to the hydrogel such as collagen or hyaluronic acid, the rate of drug release can be determined by the rate of erosion of the biodegradeable agent.

EmboCaps consist of an alginate matrix with controllable porosity that provides a means of diffusion-controlled release of a therapeutic agent. EmboCaps can also utilize erosion controlled release with the addition of EmboClear, an alginate dissolving solution that has been shown to have minimal toxicity in vivo. By adjusting the porosity of EmboCaps and varying the delivery time and dosage of EmboClear after embolization, the clinician is given unprecedented control over the release of bioactive agents from an embolic particle.

Diagnostics

Alginate based biomaterials can be combined with magnetic resonance imaging and/or ultrasound contrast agents, in order to provide visibility during procedures performed with these imaging modalities. The visibility of Alginate based biomaterials can be set to persist on a long-term basis, or to decrease after administration at a pace that can be controlled. For example, this allows using a formulation of Alginate based biomaterials that combines transient radio-opacity and long-term magnetic resonance (MR) signal. The embolic material would thus be optimally radio-opaque for safe delivery at the time of the therapeutic procedure, have its radio-opacity decrease shortly after injection in order to avoid beam-hardening artifacts on follow-up CT studies, while retaining MR signal for long-term non invasive follow up imaging studies. MR contrast agents such as the iron-based agents Feridex and Endorem, the gadolinium-based agents such as Omniscan and Magnevist, and the fluorinated magnetic resonance (MR) contrast agents such as perfluorocarbon and perfluoropolyether, can all be used in conjunction with alginate based biomaterials. The bromofluorocarbons are especially attractive since they provide Hotspot imaging on 19F MR imaging, and have sufficient radio-opacity to be conspicuous on CT. Long term labeling of alginate based biomaterials for imaging with standard clinical fluoroscopic equipment can be obtained by adding barium or bismuth sulfate. This type of labeling has potential use, for example, as radio-opaque markers for subsequent radiotherapy. Further, use of alginate based biomaterials may also have diagnostic application for selected angiography of a particular vessel.

Pharmaceutical Compositions

The invention also provides for pharmaceutical compositions. In addition to the active ingredients, these pharmaceutical compositions may contain suitable pharmaceutically acceptable carrier preparations which can be used pharmaceutically. After pharmaceutical compositions comprising a compound of the invention formulated in an acceptable carrier have been prepared, they can be placed in an appropriate container and labeled for treatment of an indicated condition with information including amount, frequency and method of administration.

The compositions of the invention include an alginate based biomaterial with a clearing agent that can selectively dissolve the alginate based biomaterial. Together, the composition has potential use for a variety of clinical and experimental applications.

The compositions of alginate based biomaterial and clearing agent, for example alginate lyase, can be used generally to treat a variety of diseases or conditions, can be used as a standalone embolic or bulking material, or it can be combined with various bioactive agents (such as chemotherapeutic agents, radio-isotopes, genes), or it can be built into a delivery agent with a controllable release.

The compositions of alginate based biomaterial and clearing agent, for example alginate lyase, are particularly useful according to the methods of the invention. Alginate biomaterials can be selectively dissolved after application, using the alginate lyase or any alginate clearing solution. The final product of the dissolution consists in a biocompatible molecule. Thus, the compositions can be used for selective release of bioactive agents, in remote locations and at a controlled pace, such as chemotherapeutic agents, radioisotopes, and genes.

The compositions of alginate based biomaterial and clearing agent, for example alginate lyase, can be used as a bulking agent for plastic and reconstructive procedures, where the combination with an alginate lyase composition would offer the possibility of secondary remodeling and consistency adjustment.

The compositions of alginate based biomaterial and clearing agent, for example alginate lyase, can be used as a transport vector for a large array of bioactive agents, such as chemotherapeutic, anti-inflammatory, or antimicrobial drugs, hormonal therapy agents, plasmid or adenovirus for gene therapy applications, or stem cells delivery. All these agents may be combined with the procedures listed above. The compositions of alginate based biomaterial and clearing agent, for example alginate lyase, can also be used for the delivery of radiolabeled particles for loco-regional radiotherapy.

Cleavable components of alginate can be incorporated into an endless number compounds, for example propylene glycol alginate, allowing for selective degradation. Further, to achieve proper viscocity, elasticity and porosity designer alginates can be explored.

The invention provides for compositions comprising an alginate lyase and a divalent metal chelator. According to the invention, the divalent metal chelator is a proteinaceous or a non-proteinaceous metal chelator. In exemplary embodiments of the method, the divalent metal chelator is a calcium chelator. The divalent metal chelator is can be, but is not limited to, any of EDTA, DTPA, DMSA, citrate, tartrate, dimercaptol, penicillamine, deferoxamine, dithizone, cisplatin, and chlorophyll. In certain embodiments, very low levels of EDTA, or no EDTA, may be preferable to miximize cytoxicity.

The compositions of the invention comprise alginate lyase. The alginate lyase can be a bacterial alginate lyase. Bacterial alginate lyases are described by Wong T Y et al. in Annual Review of Microbiol 2000. 54: 289-340, incorporated herein by reference in its entirety. In preferred embodiments, the bacterial alginate lyase is selected from the group consisting of: *Flavobacterium, Flavobacterium, Burkholderia, Corynebacterium, Klebsiella, Photobacterium, Pseudoalteromonas, Pseudomonas, Rhodopirellula, Saccharophagus, Sphingomonas, Streptomyces, Vibrio*, and *Aspergillus*. In exemplary embodiments, the composition comprises an alginate lyase that is *Flavobacterium* bacterial alginate lyase.

In certain embodiments, the alginate lyase is a transgenic alginate lyase.

According to the invention, the alginate lyase, or biologically active fragment thereof, comprises the amino acid sequence of SEQ ID NO: 1, or a fragment thereof.

Embodiments of the invention encompass an alginate based biomaterial and a contrast agent. Accordingly, the contrast agent can be selected from, but not limited to, magnetic resonance contrast agents, radioopaque contrast agents, ultrasound contrast agents, and nuclear medicine imaging contrast agents. The magnetic resonance contrast agent is selected from, but not limited to, any of: Manganese Oxide, perfluorocarbons, Feridex, Gadolinium, Combidex, Bang Magnetic Particles, Gd-DTPA, Gadolinium And Manganese Derivatives, Superparamagnetic Iron Oxide Particles, gadopentetate dimeglumine, Gd-DOTA, Gd-DTPA-BMA, Gd-HP-DO3A, Gd-DTPA-BMEA, Gd-DO3A-butrol, Gd-BOPTA, Mn-DPDP, Gd-EOB-DTPA, Gd-BOPTA, AMI-25, SH U 555A, gadoflourine-M, AMI-227, EP-2104R, P947, Gd-DTPA mesophorphryn, SH U 555 C, NC-100150, MS-325, gadoflourine-M, gadomelitolm manganese chloride, ferric amonium citrate, and barium sulfate suspensions.

Other compositions of the invention encompass an alginate based biomaterial and a biocompatible material. Preferably, a portion of the biocompatible material does not dissolve when treated with alginate lyase. The biocompatible material can be, but is not limited to, polyvinyl alcohol, sodium polyacrylate, acrylate polymers, Hyaluronase Polymers, collagen membrane, Porous HA/TCP ceramic composite, Hydroxyapatite bone cement, PVP/PMMA, tricalcium phosphate, Hydroxyapatite coated collagen fibres, calcium sulphate, Hydroxyapatite (HAp), Phosphorylcholine (PC), silicone, ultrahigh molecular weight polyethylene, polyethylene, acrylic, nylon, Polyurethane, Polypropylene, poly(methyl methacrylate), Teflon, Dacron, acetal, polyester, silicone-collagen composite, polyaledehyde, poly(vinyl chloride), silicone-acrylate, poly(tetrafluoroethylene), hydroxyethyl methacrylate (HEMA), poly(methyl methacrylate) (PMMA), poly (glycolide lactide), poly(glycolic acid), tetrafluoroethylene, hexafluoropropylene, poly(glycolic acid), poly(lactic acid), desaminotyrosyltyrosine ethyl ester, polydioxanone, fibrin, gelatin, hyaluronan, tricalcium phosphate, polyglycolide (PGA), polycaprolactone, poly (lactide-co-glycolide), polyhydroxybutyrate, polyhydroxyvalerate, trimethylene carbonate, polyanhydrides, polyorthoesters, poly(vinyl alcohol), poly(N-vinyl 2-pyrrolidone), poly(ethylene glycol), poly(hydroxyethylmethacrylate), n-vinyl-2-pyrrolidone, methacrylic acid, methyl methacrylate, and maleic anhydride, polycaprolactone, poly(amino acids) ie poly(L-lysine), poly (1-ornithine), poly(glutamic acid), polycyanoacrylates, polyphosphazenes, poly(lactic acid), poly(glycolic acid), crown ethers, cyclodextrins, cyclophanes, ethylene glycol, Methylacrylate, Para-xylylene, Biodegradable Copolymers, Copolymer Surface Coatings, Starch Polymers, Polylactic Acid, Cellophane, Tyrosine Polycarbonates Lactide and Glycolide Polymers, Collagen, PTFE, silicone, Keratin-Based Materials, Fibrous Composites—Carbon Fiber and Particles, Polymer Composites, Artificial/Natural Material Composites, Glass-Ceramic/Metal Composites, Glass-Ceramic/Non-metal Composites, Dental Composites, Ormocer, hydrogels, timed-release foams, and polymeric carriers.

Other preferred compositions of the invention encompass an alginate based wound dressing. The alginate based wound dressing can comprise one or more therapeutic agents. The therapeutic agent can be, but is not limited to, an antibiotic, an analgesic, an antifungal, and an antiviral.

The compositions of the invention can contain an alginate biomaterial. The alginate biomaterial can comprise D-mannuronic acid and D-guluronic acid. The alginate biomaterial can comprise an alginic acid. In exemplary embodiments, the alginate biomaterial is alginate.

Alginate for use in the compositions on the invention can be obtained from, but not limited to, any of the following: *Macrocystis, Laminaria, Ascophyllum*, Chlorophyceae, Phaeophyceae, Rhodophyceae, and Cyanophyceae. In exemplary embodiments, the alginate is obtained from *Aminaria hyperborean*. In other exemplary embodiments the alginate is obtained from *Laminara digita*. In other exemplary embodiments, the alginate is obtained from *Ascophyllum nodosum*. In other exemplary embodiments, the alginate is a bacterial alginate. In other exemplary embodiments, is obtained from a heterotrophic bacteria. In other exemplary embodiments, the heterotrophic bacteria are selected from the group consisting of: Pseudomonadaceae and Azotobacteriaceae.

The compositions of the invention include divalent cations. In exemplary embodiments, the divalent cation is selected from, but not limited to, $Ca^{2+}$, $Mg^{2+}$, $Ba^{2+}$ and $Sr^{2+}$. In a specific embodiment, the cation is $Ca^{2+}$. The divalent cation can be, in other embodiments, a synthetic compound with divalent orientation. In exemplary embodiments, the divalent cation is calcium. In preferred embodiments, the divalent cations are administered in liposomes or microbubbles. Liposomes can be, but are not limited to heat sensitive liposomes, ultraviolet sensitive liposomes and ph sensitive liposomes. The divalent cation can be administered simultaneously with the alginate biomaterial, or after administration of the alginate biomaterial.

In certain embodiments, the composition comprises one or more anti-cancer agents. Anti-cancer agents can include one or more chemotherapeutics typically used in the treatment of a neoplasm, such as abiraterone acetate, altretamine, anhydrovinblastine, auristatin, bexarotene, bicalutamide, BMS184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), mechlorethamine (nitrogen mustard), melphalan, mivobulin isethionate, rhizoxin, sertenef, streptozocin, mitomycin, methotrexate, 5-fluorouracil, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine. Other examples of chemotherapeutic agents can be found in Cancer Principles and Practice of Oncology by V. T. Devita and S. Hellman (editors), 6th edition (Feb. 15, 2001), Lippincott Williams & Wilkins Publishers.

It will be appreciated by those of skill in the art that the alginate lyase compositions can potentially be used for dissolving alginate in vivo in a number of applications already introduced or currently reaching a clinical phase. The ability provided by alginate lyase to selectively dissolve alginate-based material in a controlled manner offers new ways to transport diagnostic and therapeutic agents in remote locations using alginate-based vectors and release them where and when needed. In addition, the alginate lyase compositions can potentially be implemented in various alginate applications currently explored or in clinical use. Such applications include for example (i) nerve regeneration scaffold (peripheral and spinal cord), (ii) soft tissue augmentation, for instance in use as space filler for plastic surgery and to treat stress urinary incontinence, (iii) chondrocyte scaffold, (iv) encapsulation of cellular therapeutics, (v) drug delivery capsules, (vi) embolic agents as microspheres, or (vii) wound dressing for split-thickness burns.

Dosage and Mode of Administration

By way of example, a patient suffering from or susceptible to various vascular and non-vascular lesions as described herein can be treated as follows. EmboGel, EmboClear or a EmboGel/EmboClear therapeutic combination can be administered to the patient, [preferably in a biologically compatible solution or a pharmaceutically acceptable delivery vehicle, by injection through percutaneous needle or intravascular needle orcatheter. Injection can occur with a needle or catheter system in a coaxial arrangement when alginate and a divalent cation are injected as separate solutions. Alternatively, if the alginate preparation contains particles that selectively release a divalent cation upon UV light, ultrasound, temperature stimulation, then said preparation could be delivered through a standard single lumen needle or catheter system. Alginate biomaterials may also be polymerized outside of the body and implanted after they have been crosslinked with a divalent cation. In cases in which said biomaterial only partially contains alginate, ridigidity may not result from gelation in divalent cation. For these reasons alginate containing biomaterials may have the consistency appropriate for injection through a single catheter or surgical implantatation in the absence of administering a metal cation, such as a divalent cation. The dosages administered will vary from patient to patient.

An additional method of delivery of alginate-based biomaterials makes use of a needle-catheter system such as the Outback catheter (Cordis Endovascular), which is currently marketed as a re-entry catheter for peripheral chronic total occlusions. The Outback is equipped with an L-shaped radio-opaque marker that provides controllable and reproducible orientation of the needle tip toward the target site. This proprietary locate, turn and deploy technique is ideal for the novel application of delivery of liquid embolic agents such as alginate-based biomaterials into a target cavity. Specifically after deployment of a stent covered with a membrane, the needle-catheter system may be used to puncture through the membrane in order to deliver an alginate-based biomaterial such as EmboGel. As previously mentioned, the delivery of a liquid embolic agent behind a covered or partially covered stent would ensure that the embolic agent is contained within the targeted cavity. Such a system would decrease the likelihood that a "tail" of liquid embolic agent protrudes into the parent artery after needle withdrawal, and would also decrease the risk of long-term recanalization and/or leak. Such a delivery strategy could be used to treat sidewall saccular aneurysms, or fusiform aneurysms such as abdominal aortic aneurysms (AAAs). Potential membranes include but are not limited to porous PTFE, Dacron, nylon or other biocompatible porous or semiporous membranes. The porosity of the membrane can be chosen to optimize the exit of the blood volume contained within the target cavity as it is progressively filled with the embolic agent, while keeping the embolic agent itself securely contained within the target cavity (selective permeability). Alternatively, a nonporous membrane could be punctured twice, one hole serving for needle access and embolic agent delivery, the second hole allowing draining out the blood volume initially contained within the targeted cavity.

In any of the treatments described, a therapeutically effective dosage regimen should be used. By "therapeutically effective", one refers to a treatment regimen sufficient to restore the subject to the basal state, as defined herein, at the cellular or tissue site of manifestation or to prevent brain edema in an individual at risk thereof or restore the subject's brain to the basal state. Alternatively, a "therapeutically effective regimen" may be sufficient to arrest or otherwise ameliorate symptoms of brain edema. Generally, in the treatment of brain edema, an effective dosage regimen requires providing the medication over a period of time to achieve noticeable therapeutic effects.

Generally, a therapeutic composition of the invention will be administered in a single does of alginate or alginate-lyase composition. Alginate composition may be provided in the range of 1 nanoliter per kg body weight to 50 mL per kg body weight. Alginate lyase may be provided in the range of 1 nanoliter per kg body weight to 50 mL per kg body weight. The alginate lyase and divalent metal chelator are administered at a ratio of between 99:1-1:99, for example a ratio of 99:1, 98:2, 97:3, 96:4, 95:5, 90:10, 85:15, 80:20, 75:25, 70:30, 60:40, 50:50, 40:60, 30:70, 25:75, 20:80, 15:85, 10:90, 5:95, 4:96, 3:97, 2:98, 1:99.

The dosages of alginate composition and alginate lyase composition will be administered at different time points, depending on the method of treatment, as considered appropriate by the treating physician.

Alginate based biomaterials can be delivered in a number of ways according to the instant methods. Alginate can be injected concurrently with a solution of calcium, or any divalent cation, and the hardening (gelation) of the alginate based biomaterial can be achieved through the addition of calcium-containing liposomes. Such liposomes can be forced to release their calcium-containing contents through heat or light activation. Using such technique would result in the polymerization of alginate biomaterial through heat-sensitive or photosensitive liposomes, respectively. According to the invention, any other natural or synthetically derived compounds with two adjacent positive charges may be used in place of calcium for gelation of the alginate based biomaterial.

In particular embodiments of the invention, a single syringe can be used to deliver the alginate based biomaterial and divalent cation compositions. A single syringe with two compartments of varying size attached to the same plunger handle is used to deliver an exact ratio of alginate and divalent cations. This method of delivery enables consistent delivery of the proper ratio of the alginate and calcium chloride compound. U.S. Patent Application No. 20050133046 describes delivery of alginate based biomaterials, and is incorporated by reference herein in its entirety.

In another exemplary method of delivery, any of the compositions of the invention described herein can be delivered through an endoscope. For example, delivery can be carried out through an endoscopic injection. In one such example, U.S. Pat. No. 5,261,889, incorporated by reference herein in its entirety, describes a catheter for use with an endoscope that includes a projectable and retractable needle for the introduction of injectable drug agents and a visual-path irrigation lumen disposed adjacent to the needle for providing irrigation fluid to a target site within body tissue.

In a further exemplary method of delivery, any of the compositions of the invention described herein can be delivered using a bronchoscope. Use of a bronchoscope according to the methods of the invention is suited, in exemplary embodiments, for use in pulmonary applications. A bronchoscope can be used to deliver any of the compositions of the invention inside the bronchial tree and airway. Further, the delivery mechanism has use in the method of tumoral marking for subsequent radiotherapy, using, for example, any of the methods of the invention described herein. In particular, delivery of the compositions of the invention with a bronchoscope has use in the methods of controlled release of a label in a subject, or controlled release of an agent in a subject. Further, the method of delivery has application in lung volume reduction procedures using any of the compositions of the invention as described herein.

In preferred methods of the invention the composition comprising alginate lyase and the divalent metal chelator are co-administered from the same device. The device for administration can be a syringe. Alternately, a microcatheter is suitable for administration.

Localized Administration

Localized administration of a therapeutic composition according to the invention is preferably by injection directly in to blood vessels or by means of a microcatheter. drip device, drug pump or drug-saturated solid matrix from which the composition can diffuse implanted at the target site.

In certain embodiments, therapeutic composition according to the invention may be used to deliver radiolabeled particles. Such use is particularly suited for the delivery of radiolabeled particles for locoregional radiotherapy.

Systemic Administration

Systemic administration of a therapeutic composition according to the invention may be performed by methods of whole-body drug delivery are well known in the art. These include, but are not limited to, intravenous drip or injection, subcutaneous, intramuscular, intraperitoneal, intracranial and spinal injection, or by the use of an implantable, time-release drug delivery device.

Systemic administration is advantageous when a pharmaceutical composition must be delivered to a target tissue that is widely-dispersed, inaccessible to direct contact or, while accessible to topical or other localized application, is resident in an environment (such as the digestive tract) wherein the native activity of the nucleic acid or other agent might be compromised, e.g. by digestive enzymes or extremes of pH.

A therapeutic composition of use in the invention can be given in a single- or multiple dose. A multiple dose schedule is one in which a primary course of administration can include 1-10 separate doses, followed by other doses given at subsequent time intervals required to maintain and or reinforce the level of the therapeutic agent. Such intervals are dependent on the continued need of the recipient for the therapeutic agent, and/or the half-life of a therapeutic agent. The efficacy of administration may be assayed by monitoring the reduction in the levels of a symptom indicative or associated with brain edema which it is designed to inhibit. The assays can be performed as described herein or according to methods known to one skilled in the art.

A therapeutically effective regimen may be sufficient to arrest or otherwise ameliorate symptoms of a disease. An effective dosage regimen requires providing the regulatory drug over a period of time to achieve noticeable therapeutic effects wherein symptoms are reduced to a clinically acceptable standard or ameliorated. The symptoms are specific for the therapeutic use.

Kits or Pharmaceutical Systems

The present compositions may be assembled into kits or pharmaceutical systems for use in dissolving an alginate based biomaterial. The kits can comprise an alginate lyase, a divalent metal chelator, and instructions for use. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for dissolving an alginate based biomaterial.

The present compositions may be assembled into kits or pharmaceutical systems for use in treating a subject that has received treatment with an alginate based biomaterial. The kits can comprise an alginate lyase, a divalent metal chelator, and instructions for use. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for treating a subject that has received treatment with an alginate based biomaterial.

The present compositions may be assembled into kits or pharmaceutical systems for use in treating a subject suffering from a vascular or non-vascular condition, a vascular or non-vascular occlusion, a vascular or non-vascular hemorrhage, or a neoplastic growth, wherein the subject has previously received treatment with an alginate based biomaterial. The kits can comprise an alginate lyase, a divalent metal chelator, and instructions for use. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for treating a subject suffering from a vascular or non-vascular condition, a vascular or non-vascular occlusion, a vascular or non-vascular hemorrhage, or a neoplastic growth, wherein the subject has previously received treatment with an alginate based biomaterial.

The present compositions may be assembled into kits or pharmaceutical systems for selective dissolution of an occlusion in a subject. The kits can comprise an alginate based biomaterial, alginate lyase, a divalent metal chelator, and instructions for use. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for selective dissolution of an occlusion in a subject.

The present compositions may be assembled into kits or pharmaceutical systems for selective delivery of a therapeutic agent to a targeted non-occluded vessel in a subject, or selective control of bulking or remodeling, or the controlled release of a label in a subject, or the controlled release of a label to mark lesions for radiosurgery in a subject, or the controlled release of a contrast agent in a subject. The kits can comprise an alginate based biomaterial, alginate lyase, a divalent metal chelator, and instructions for use. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for selective delivery of a therapeutic agent to a targeted non-occluded vessel in a subject, or selective control of bulking or remodeling, or the controlled release of a label in a subject, or the controlled release of a label to mark lesions for radiosurgery in a subject, or the controlled release of a contrast agent in a subject.

The present compositions may be assembled into kits or pharmaceutical systems for the selective dissolution of a biocompatible material in a subject. The kits can comprise an alginate loaded biocompatible material, alginate lyase, a divalent metal chelator, and instructions for use. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for selective dissolution of a biocompatible material in a subject.

The present compositions may be assembled into kits or pharmaceutical systems for selective dissolution of a wound dressing in a subject. The kits can comprise an alginate based biomaterial, alginate lyase, a divalent metal chelator, and instructions for use. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using the compounds of the invention for selective dissolution of a wound dressing in a subject.

Having now generally described the invention, the same will be more readily understood through reference to the following Examples, which are provided by way of illustration, and are not intended to be limiting of the present invention, unless specified.

EXAMPLES

Methods of the Invention

The results reported herein were obtained using the following Materials and Methods and Experimental Settings:

Purified Alginate Preparation.

Method

As a first step, Protanal-HF alginate is dissolved to 0.1% in 0.5 mM EDTA, 10 mM HEPES, pH 7.0. Next, the solution is filtered to 0.45 microns to remove particulates. In a separate flask, 4 gm fine mesh activated charcoal per gram alginate is bleached by resuspension to 4% (w/v) in 0.1 M sodium perchlorate. Following 30 minutes mixing the bleached charcoal is washed by centrifugation (5 min @ 500×g) twice with water, 4× with ethanol, 4× with water. The supernatants are then discarded.

The bleached activated charcoal slurry is added to the filtered alginate and stirred for 30 min to adsorb organic contaminants. The supernatant is filtered to 0.22 micron; then filtered at 0.1 micron. 10.2 ml 10% $MgCl_2.5H_2O$ per liter is added to the filtrate and it is mixed thoroughly. 3.8 ml 34% $CaCl_2.2H_2O$ is gradually added while stirring and then mixed for 30 min to precipitate the higher molecular weight, guluronate-rich chains. Next, the mixture is spun for 20 min at 2,000×g, and the supernatant is discarded.

The pellet volume is estimated and 2 volumes 0.1 M EDTA, 10 mM HEPES, pH7.0 is added. Q.s. $H_2O$ to 500 ml per gram alginate starting material. The pH is adjusted to 7.0 if necessary. Concentrate 10 fold by ultrafiltration to 10 kD to remove small fragments. Dilute retentate to starting volume with water and reconcentrate. The prior step is repeated. Dilute retentate back to starting volume again with water. Add 1/20 volume 2.5 M NaCl. While vigorously stirring, slowly add an equal volume of ethanol. Spin 10 min at 500×g. Discard supernatant. Redissolve in 120 mM NaCl, 0.5 mM EDTA (200 ml per gram alginate starting material). While vigorously stirring, slowly add 4 volumes of ethanol. Spin 10 min at 500×g. Discard supernatant. Thoroughly resuspend pellet in 1 liter ethanol per gram alginate starting material (will not dissolve). Spin 10 min at 500×g. Discard supernatant. Thoroughly resuspend pellet again in 1 liter ethanol per gram alginate starting material. Collect precipitate on fine mesh stainless steel sieve. Press out excess liquid. Tease with forceps to fluff precipitate. Dry at 60 C in vacuo. Store the dry purified alginate in a cool, dry place until ready for use. Dissolve to desired concentration in buffer (10 mM HEPES buffered normal saline with 0.5 mM sodium citrate) and sterilize by filtration.

Preparation of the Alginate Based Biomaterial/Alginate Lyase Composition

Alginate Based Biomaterial

To prepare Alginate based biomaterial, protanal HF alginate from FMC Biopolymers (Haugesund, Norway) was added at a concentration of 2% w/v to a standard nonionic contrast agent (Iohexyl, Omnipaque 300, Amersham Health, Princeton, N.J.). This mixture of Iohexyl and alginate was then purified with filtration through a 0.2 μm-pore-size filter. Polymerization of Alginate based biomaterial was achieved by co-injection with a 100 mM calcium chloride solution.

Alginate based biomaterial is made radiopaque by dissolving alginate directly in a colloidal gold solution containing 50 nm gold particles covered in dextran (Nanocs). In a preferred embodiment alginate is added to the golloidal gold solution at a concentration of 2% w/v. This colloidal gold/alginate solution can then be polymerized respectively into microcapsules or in a strand form depending on the particular application.

Alginate Lyase Composition

To prepare the alginate lyase composition, anhydrous ethylene-diamine-tetra-acetic acid (EDTA) (Sigma, St. Louis, Mo.) was added at a concentration of 5 mg/mL to normal saline. The pH of this preparation was then adjusted with sodium hydroxide and, if necessary, hydrochloric acid to an approximated pH of 7.0 (range 6.5-7.5). Alginate lyase isolated from *Flavobacterium* sp. (Sigma, St. Louis, Mo.) was then added at a concentration of 2 mg/ml to the EDTA solution.

Liposome Preparation

Liposomes were prepared using the extended hydration method. Phosphatidylcholine (Avanti Polar Lipids, Alabaster, Ala.) and cholesterol (Sigma, St. Louis, Mo.) in a 1:1 mole ratio in chloroform were dried in a rotary evaporator. When encapsulating doxorubicin, it was dissolved in methanol and combined with the lipids prior to rotary evaporation. The lipid film was solvated and annealed for 2 hours at 55 C with a solution of either calcein (Sigma, St. Louis, Mo.) or PBS. In order to form vesicles of a specific size, the lipid suspension was taken through twenty-one cycles of extrusion (LiposoFast, Avestin, Ottawa, Ontario, Canada) through two stacked polycarbonate filters (100 nm or 400 nm pore size). Unencapsulated drug was removed using size exclusion chromatography with sephadex G-50 resin (Sigma, St. Louis, Mo.). Dynamic light scattering (DLS) measurements of liposome suspensions was studied with a Malvern Instruments Nanosizer ZS90 (Southborough, Mass.), equipped with a 633 nm He—Ne laser light source. Scattering was detected at 90. All buffer solutions used were filtered with 0.22 μm filters just prior to vesicle preparation.

Microencapsulation

The synthesis of EmboCaps involves the use of an electrostatic (van de Graaff) droplet generator. Calcein or doxorubicin containing liposome were first suspended in 2% w/v ultrapurified sodium ProtanalÒ HF alginate (FMC Biopolymers). This solution was passed through a needle at a flow rate of about 200 ml/min using a nanoinjector pump. Droplets were collected in a Petri dish containing 100 mM CaCl2 and then washed three times in saline. To create MR visible EmboCaps, the SPIO Feridex was added at a concentration of 20% vol/vol to the ungelled alginate, liposome polymer mixture. To create x-ray visible EmboCaps, barium sulfate or dextran covered gold particles (Nanocs, 50 nm) were added at a concentration of respectively 20% w/volume or 20% volume/volume to the ungelled alginate, liposome polymer matrix. To create MR and X-ray visible EmboCaps, barium sulfate and Feridex were added to EmboCaps at respectively a concentration of 10% vol/vol and 10% w/volume. To created fluorinated EmboCaps, emulsions of perfluoroctylbromide or perfluoropolyether in lecithins were added at a concentration of 20% vol/vol to the ungelled alginate, liposome polymer matrix. To synthesize fluorine emulsions, a lecithin-water mixture (5% lecithin in water w/v) was sonicated at 40% power until the lecithin-water mixture was transparent. 400 μL PFOB or PFPE is then added to 800 μl lecithin-water mixture (40% PFPE/PFOB v/v). This solution is then sonicated 5 cycles of 5 minutes over ice until an emulsion is formed.

Calcein In Vitro Release Studies

Hydrated loaded beads (100 mg) are weighed into a 1.5 mL microcentrifuge tube (eppendorf) and 1 mL buffer (10 mM histidine pH 7.4) added. The sample is placed in an incubator shaker at 37 degrees C. and 100-200 rpm. At selected time intervals, the sample is removed from the incubator, centrifuged (eppendorf, 1000 rpm, 2 min) and the supernatant is removed and replaced with 1 mL of fresh buffer. The concentration of calcein in the supernatant was measured with a fluorometer.

Experimental Settings

In Vitro Experiments

The in vitro experiments were conducted with a simple glass model of saccular aneurysm located at a T-shaped arterial bifurcation, and connected to a hydraulic pump.

Experiment #1—A covered stent was placed across the aneurysm neck to exclude the aneurysm from the circulation. The aneurysmal cavity was then filled with Alginate based biomaterial. After completion of the procedure, the alginate lyase composition was injected in order to dissolve the alginate based biomaterial. This experiment demonstrates the dissolvability of the alginate based biomaterial in vitro.

Experiment #2—Using the same model, embolization of the aneurysmal cavity was repeated and the degree of radio-opacity of the alginate based biomaterial documented by plain x-ray and computed tomography (CT) immediately after the procedure and after 24 hours of continuous flow through the parent artery. This experiment demonstrates the decrease in radio-opacity of the alginate based biomaterial in vitro.

In Vivo Experiments

All in vivo experiments were conducted on two New Zealand White rabbits (males, approx. 4 kg). These non-surviving experiments were performed in accordance with the regulations of our Institution Animal Care and Use Committee.

Experiment #1—In the first rabbit, vascular access was obtained by inserting a 5F sheath in the right common carotid artery (CCA). The alginate based biomaterial was injected in the distal abdominal aorta and pelvic arteries, followed by injection of Alginate lyase composition. This experiment demonstrates the dissolvability of the alginate based biomaterial in vivo.

Experiment #2—In the second rabbit, a wide neck aneurysm was created following a standardized protocol (26). Briefly, a 5F arterial sheath was inserted in the right common carotid artery (CCA) through surgical access. The proximal portion of the CCA was isolated from the circulation by inflating a balloon across its origin, and exposed to a solution of elastase. The balloon and sheath were then removed, the CCA ligated, and the surgical wound sutured. The non-surviving experiment was conducted one month after aneurysm creation. The wide neck aneurysm was filled with the alginate based biomaterial in the absence of aneurysmal neck protection (e.g., no stent or balloon), in order to simulate a clinical complication secondary to embolic material migration. The aneurysm was embolized using a coaxial delivery system: A 2.8F microcatheter (Hypertransit, Cordis Neurovascular, Miami) was introduced into a straight-tip 5F diagnostic catheter (Cook, Bloomington, Ind.), previously placed into the aneurysmal cavity over a standard 0.035 guidewire. This experiment examines the dissolvability of the alginate based biomaterial in vivo in a setting simulating a typical clinical situation. It is demonstrates the use of the alginate based biomaterial during a complication of endovascular therapy using a liquid embolic agent, in this case, the treatment of a wide-neck saccular aneurysm with alginate.

Experiment #3—After completion of experiment #2, the left common carotid artery (CCA) was accessed and partially embolized with Alginate based biomaterial. Three milliliters of the alginate lyase composition were subsequently injected in order to dissolve the alginate based biomaterial. This experiment demonstrates the in vivo dissolvability of alginate based biomaterial in a craniocervical distribution.

Example 1

Alginate Based Biomaterial/Alginate Lyase Composition Application and Use In Vitro Alginate based biomaterial is a non-adhesive agent, reducing the risk of microcatheter tip retention as seen with currently available liquid embolic agents (NBCA, EVAL). A series of in vitro experiments were performed to document that the alginate based biomaterial can be selectively injected in a targeted lesion, and then dissolved with the EmboClear solution. In in vitro experiment #1, the covered stent was successfully deployed within the lumen of the parent vessel, across the aneurysm neck (FIG. 1 a-c). A coaxial needle system was advanced across the stent into the aneurysmal cavity. The alginate based biomaterial was successfully injected into the aneurysm (FIG. 1 d-f), achieving complete filling of the aneurysmal sac (FIG. 1f). The alginate lyase composition was then injected into the aneurysmal cavity in order to dissolve the polymerized alginate based biomaterial. Within a minute of delivering Alginate lyase composition, the alginate based biomaterial successfully dissolved into liquid components that could freely pass through the covered stent membrane, as shown in FIG. 2a-c. The dissolved embolic material was washed off the aneurysmal cavity through the membrane surrounding the covered stent, suggesting that dissolved Alginate based biomaterial was then in a liquid or near liquid state. This experiment shows that the alginate based biomaterial can be dissolved after injection, either as a method to release other agents coupled with alginate based biomaterial, or as a treatment option in case of inadvertent embolization of normal branches during a therapeutic procedure.

Figure 3B:
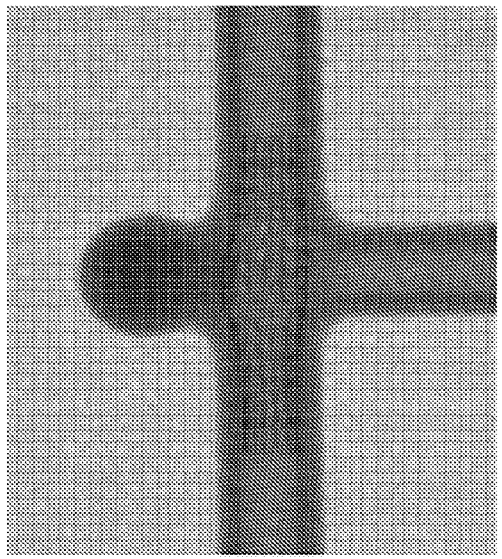
FIG. 3 (a-d) is four panels showing loss of alginate based biomaterial radio-opacity in a glass aneurysm model. Panel a) shows a plain x-ray image immediately after alginate based biomaterial embolization showing marked radio-opacity of the material. Panel b) shows a control x-ray image obtained after 24 hours of perfusion with normal saline, demonstrating reduction in radio-opacity. The CT images obtained immediately after the procedure, shown in panel c) and 24 hours later, shown in panel d), confirm the significant reduction in density, as measured by the CT equipment. The oval shape shown in Figures c) and d) indicates the region interrogated for density measurement).
Figure 3D:
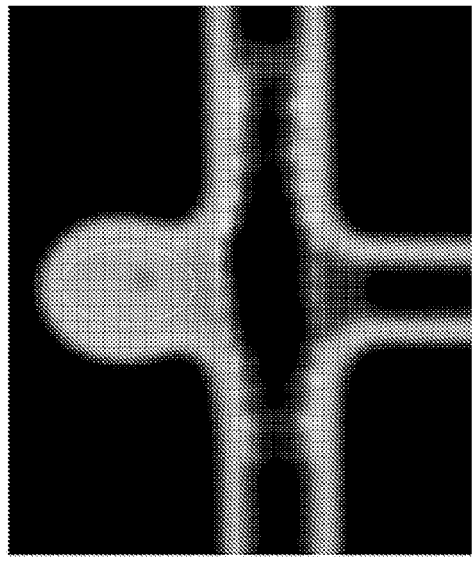
Figure 3A:
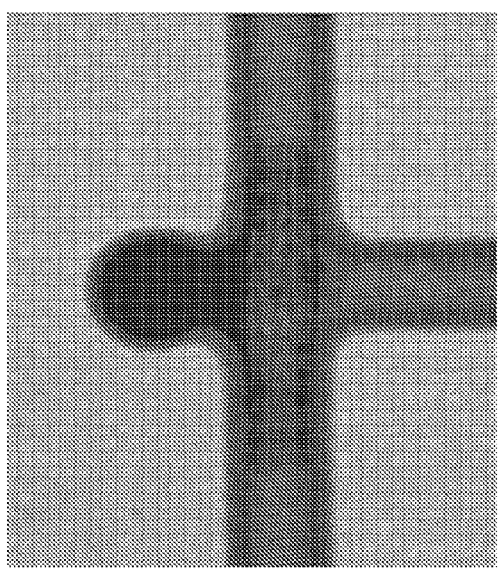
Figure 3C:
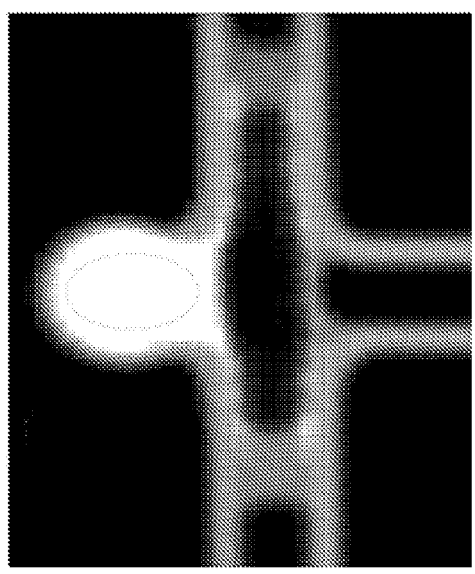
Figure 7:
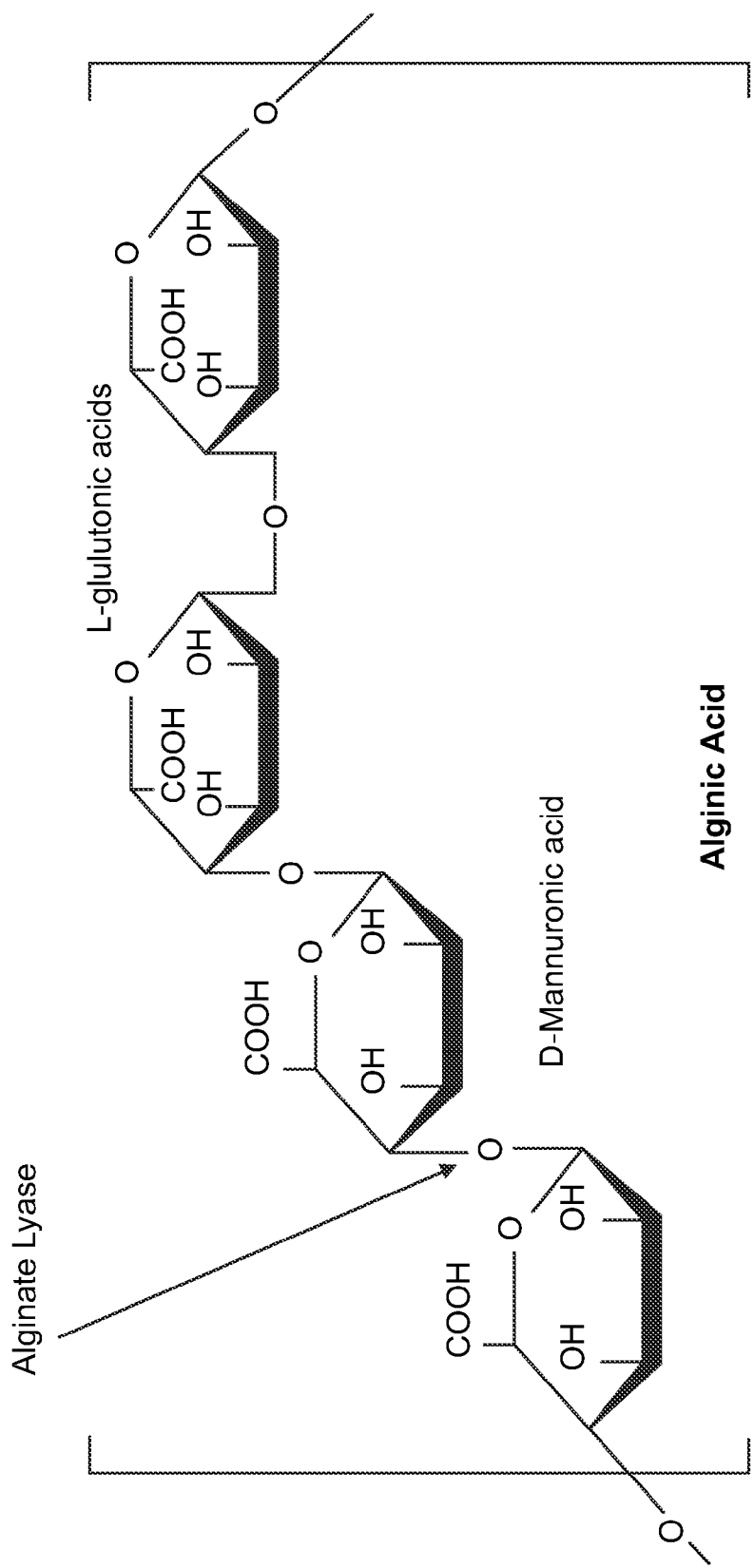
FIG. 7 is a schematic showing the enzymatic cleavage site of mannuronate (EC4.2.2.3) alignate lyase on alginate.

The second in vitro experiment demonstrates the decrease in radio-opacity shown by the alginate based biomaterial over a 24-hour period of time. Here, the model used in experiment #1 (aneurysm with stent) was re-accessed and filled with alginate based biomaterial. The opacity of the alginate based biomaterial was documented with plain x-ray and CT immediately after embolization (FIG. 3a,c), and after 24 hours of continuous circulation of normal saline through the parent artery lumen (FIG. 3b,d). Plain x-ray films show a very radio-opaque embolic material immediately after embolization, which becomes barely detectable 24 hours later. CT confirms that the distribution of the alginate based biomaterial within the aneurysm cavity is unchanged (FIG. 3d), and documents a decrease in measured density, from 7108.7 HU to 1161.1 HU.

Taken together, this data shows that the alginate based biomaterial can be adequately opaque for accurate control during an image-guided procedure, and lose part of its radio-opacity after the procedure is completed, while retaining its MR and ultrasonographic characteristics. The advantage of this characteristic is to avoid beam-hardening artifacts that typically impair follow-up evaluations with CT.

Example 2

Alginate Based Biomaterial/Alginate Lyase Composition Application and Use In Vivo Here, in vivo experiments were carried out. In in vivo experiment #1, the distal abdominal aorta was easily catheterized, and a baseline pelvic angiogram performed, as shown in FIG. 4a. Alginate based biomaterial was then injected into the distal abdominal aorta and the ilio-femoral axes bilaterally (FIG. 4b) resulting in complete occlusion of the pelvic vasculature (FIG. 4c). The Alginate lyase composition solution was then infused, and within a minute of infusion, the alginate based biomaterial was dissolved, resulting in regained patency of the abdominal aorta and most of the iliac arterial distribution (FIG. 4d). This in vivo experiment confirms that the alginate based biomaterial can be dissolved in vivo, even when a large quantity of the embolic material results in occlusion of major arterial branches. The second in vivo experiment further investigated the ability of Alginate based biomaterial to be dissolved in vivo by simulating a complication of therapeutic embolization of a saccular aneurysm with a liquid embolic agent.

In in vivo experiment #2, an in vivo model of saccular aneurysm was successfully created. FIG. 5a shows the initial angiographic appearance of the wide neck aneurysm, made of a dilatation of the proximal right common carotid artery. After embolization with Alginate based biomaterial, part of the alginate injected remained stable in the deep portion of the aneurysmal sac, while the more superficial component was rapidly flushed away into the right subclavian artery. FIG. 5b shows the partially obliterated aneurysm and documents significant distal flow impairment in the subclavian artery territory, including numerous distal branch occlusions. FIG. 5c shows a control angiogram obtained after infusion of 2 ml of alginate lyase composition within the aneurysm cavity; and it demonstrates clearing of the embolic material in both the aneurysm and the distal subclavian circulation, as well as regained patency of the previously impaired vascular territories. This experiment shows that after unprotected injection of alginate based biomaterial into the aneurysmal cavity, part of the embolic agent has been washed off and migrated distally into normal arterial branches, resulting in the occlusion of several main arteries. Injection of the Alginate lyase composition solution successfully dissolved the embolic material within the aneurysmal cavity as well as in the occluded distal branches, with excellent angiographic control showing regained patency.

The third in vivo experiment documents dissolvability of Alginate based biomaterial within the craniocervical circulation. In in vivo experiment #3, the 5F diagnostic catheter was placed into the left common carotid artery (CCA), and baseline DSA obtained. Since there is no right CCA in this rabbit (as it was used for the creation of the aneurysm model), bilateral cerebral distribution of the contrast agent is noted (FIG. 6a). Subsequently, a large quantity of alginate was injected into the carotid circulation using a coaxial system as described for the previous experiment (FIG. 5b). Control angiography documented severe flow impairment in the cranial circulation bilaterally (FIG. 5c). In particular, the left ophthalmic circulation was not patent anymore, as obviated by the disappearance of a previously well-documented choroids blush. A final angiogram obtained after administration of approximately 3 ml of Alginate lyase composition solution shows regained patency of the cerebral circulation (FIG. 5d). Of particular interest is the reappearance of the left choroid blush, indicating that blood flow has been re-established in very small circulatory systems (FIG. 5d). Of note in this experiment is the occlusion and subsequent flow restitution within the choroids plexus of the left eye, which indicate that the dissolved Alginate based biomaterial was washed off through minute vascular pathways. This characteristic is important both in case of planned dissolution of Alginate based biomaterial in target organs for local delivery of coupled agents, and for rescue dissolution of Alginate based biomaterial after untoward embolization of normal vessels.

Example 3

Use of Alginate Lyase Composition for Release of Agent from Mirocapsules

Figure 8B:
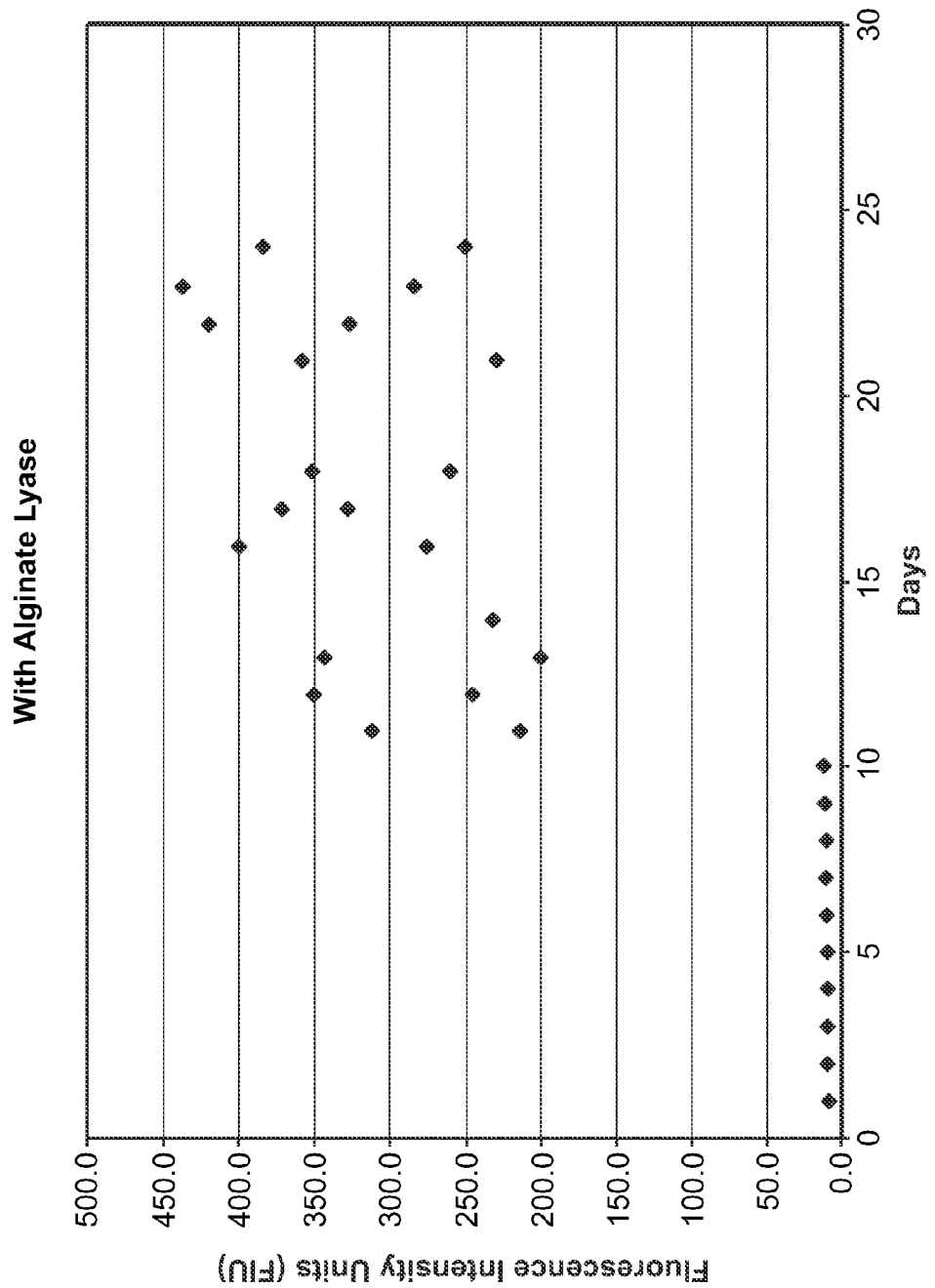
FIG. 8 (*a* and *b*) show fluorescent readings taken from the supernatant of alginate microcapsules containing liposomes loaded with calcein. Panel a shows fluorescence in supernatant remained at negligible levels until addition of the alginate lyase composition at day 11 causing rapid release of calcein containing liposomes. Panel b below is a comparable release profile of calcein from liposomes in alginate without addition of the alginate lyase composition-note the gradual release profile.
Figure 10A:
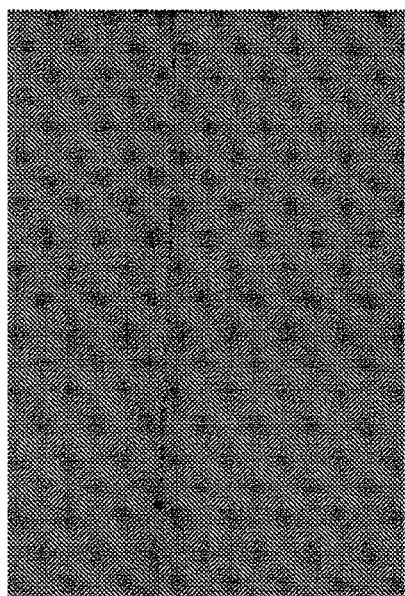
FIG. 10 (*a-d*) is four panels. Panel a shows guidewire and stent placed across the neck of glass saccular aneurysm model. Panel b shows deployment of the stent across the aneurysm neck. Panel c shows advancement of the Outback catheter through the stent with exit point positioned towards aneurysmal orifice (note radio-opaque L-marker pointing upward). Panel d shows puncture through the covered stent with the Outback catheter enabling delivery of the liquid embolic agent into the targeted aneurysmal sac.
Figure 10B:
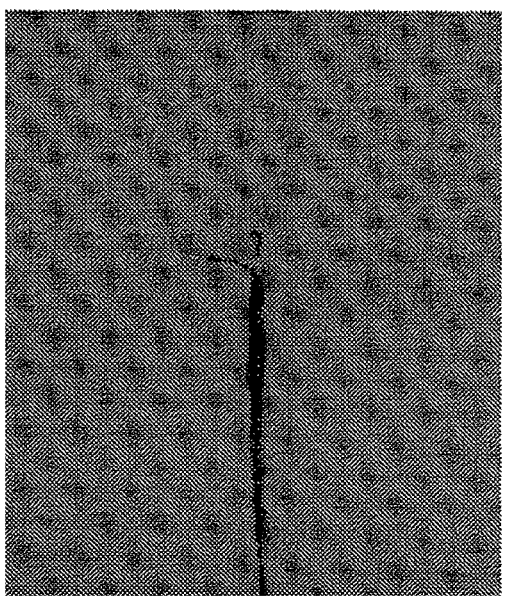
Figure 10C:
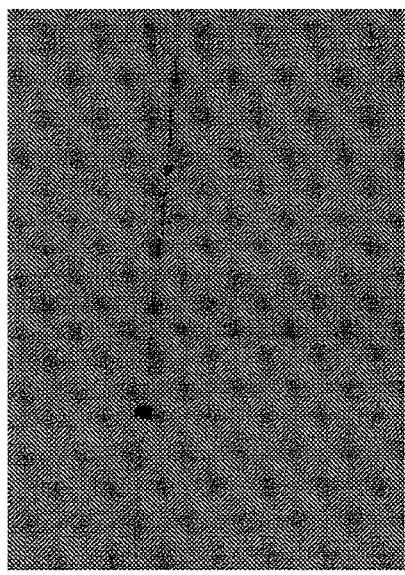
Figure 10D:
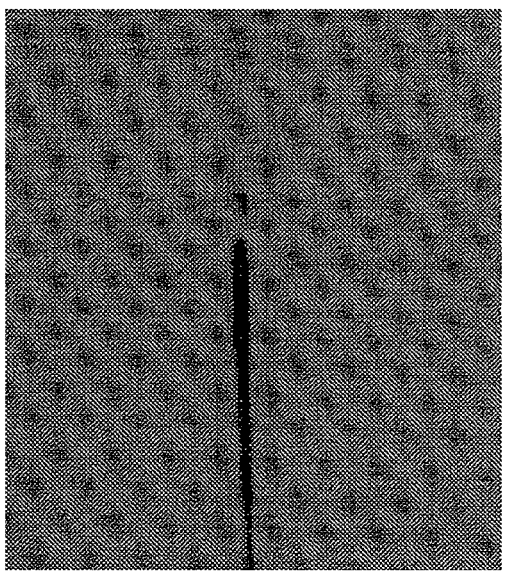

Here, the ability of alginate lyase to release labeling agent from microcapsules was examined. Alginate microcapsules were loaded with calcein. FIG. 8 shows fluorescent readings taken from the supernatant of alginate microcapsules containing liposomes loaded with calcein. Fluorescence in the supernatant remained at negligible levels until addition of alginate lyase and a divalent metal chelator at day 11, causing rapid release of calcein containing liposomes (FIG. 8B). Below is a comparable release profile of calcein from liposomes in alginate without addition of the alginate lyase composition (FIG. 8A). Of note is the gradual release profile.

Example 4

Selectively Dissolvable Alginate EmboCaps for Novel Drug Delivery Strategies

Described here is the preparation and characterization of a novel drug delivery strategy, the Manganese EmboCap. EmboCaps can be rapidly dissolved in vivo by the alginate-dissolving agent EmboClear, which consists of an alginate lyase, and in certain preferred embodiments ethylenediaminetetraacetic acid (EDTA).

EmboCaps are particularly attractive for intravascular delivery strategies as microcapsules can be used as embolic agents to create a reversible stasis thereby allowing a high pay-load of therapeutic agent to be delivered to a relatively well targeted area. EmboCaps can be potentially used as transport vectors for the delivery and/or controlled release of a large array of bioactive agents, such as chemotherapeutic, anti-inflammatory, or antimicrobial drugs, hormonal therapy agents, gene therapy vectors, or radioisotopes for radiotherapy.

As proof of principle the release profile of calcein containing liposomes from EmboCaps in the presence and absence of EmboClear was examined. The release profile of liposomes containing Doxorubicin in EmboCaps with and without the addition of EmboClear was also examined. Assays conducted in vitro indicate that EmboCaps provide a sustained release of calcein, and Doxorubicin over a period of respectively 25 days and 15 days in the absence of EmboClear. With the addition of EmboClear, the capsular contents are rapidly released and EmboCaps are safely dissolved into non-toxic liquid by-products that can freely pass through the microvasculature and are rapidly cleared from the body. Microscopic analysis of EmboCaps further confirmed that with the addition of EmboClear, capsules rapidly dissolve, for example in about 30 seconds, into liquid components.

Embolotherapy is a clinical procedure that is used by interventional radiologists to mechanically block the flow of blood. In the past decade, embolotherapy has been adopted for loco-regional treatment of a number of conditions including uterine fibroids, liver tumors and intracranial/extracranial neoplasms. Since these procedures are less invasive with comparable results to conventional surgery, the growth of these procedures has been exponential. Emblotherapy can also be used to provide site-targeted delivery of bioactive agents. To this end, many groups have explored the use of drug-eluting embolic agents to dually cause vascular stasis while releasing bioactive agents in a loco-regional manner.

As many bioactive agents in the current clinical armaterium are inherently unstable, the development of drug-eluting embolic agents poses a formidable obstacle for researchers. Conditions employed during encapsulation can influence the biological activity causing denaturation of sensitive biomolecules. For example, proteins and peptides are inherently unstable, even in the absence of strong acids and proteases. They tend to unravel, or denature, under certain conditions, causing them to lose biological activity. Therefore, any effective protein/peptide delivery system will also have to stabilize the therapeutic molecules in storage as well as after administration. In addition, the encapsulation template must be biocompatible to prevent ilicitation of an immune response in vivo.

For many groups, the use of a gentle aqueous hydrogel microencapsulation process has resulted in retention of the native state of the bioactive agent in a biocompatible matrix. The most frequently studied method of aqueous microencapsulation involves ionotropic gelation of alginate using multivalent ions, particularly calcium. The relatively mild gelation process has enabled not only proteins, but also cells and DNA to be incorporated into alginate matrices with retention of full biological activity (Alexakis et al., 1995). Furthermore, by selecting an appropriate type of alginate and coating agent, the pore size, the degradation rate, and ultimately the release kinetics can be controlled. Gels of different morphologies can be prepared including large block matrices, large beads (1 mm-5 mm) and microbeads (100 µm-0.1 mm in diameter). All these properties, in addition to the non-immunogenicity of alginate, have led to an increased use of this polymer as a protein delivery system (Maysinger et al., 1992).

The experiments described herein present a third potential drug delivery strategy that allows for selective exploitation of diffusion-controlled and/or erosion controlled release of a bioactive agent. EmboCaps consist of an alginate matrix with controllable porosity that provides a means of diffusion-controlled release of a therapeutic agent. EmboCaps can also utilize erosion controlled release with the addition of EmboClear, an alginate dissolving solution that has been shown to have minimal toxicity in vivo. By adjusting the porosity of EmboCaps and varying the delivery time and dosage of EmboClear after embolization, the clinician is given control over the release of bioactive agents from an embolic particle.

EmboClear dissolutive action is obtained by combining the effects of ethylenediaminetetraacetic acid (EDTA) and alginate lyase. In certain embodiments, very low amounts of EDTA are used so as to minimize toxicity. By very low amounts is meant the smallest amount that is sufficient for the dissolution of polymerized alginate. Alginate polymerizes in the presence of calcium. EDTA is necessary for the dissolution of polymerized alginate as it chelates the calcium, and un-polymerizes EmboGel in its hardened form. EDTA alone, however, does not rapidly dissolve alginate. This is why EmboGel combines EDTA with alginate lyase. Alginate is composed of blocks of mannuronic acid homopolymeric regions and guluronic acid homopolymeric regions, and alternating copolymer regions of mannuronic acid and guluronic acid (GMGMGM . . . ). Alginate lyase cleaves at the beta-(1-4)-D-mannuronic bonds residues to yield oligosaccharides with 4-deoxy-a-L-erythro-hex-4 enopyranuronosyl groups at their non-reducing terminus. Alginate enzymatic hydrolysis with the alginate lyase enzyme creates polymannuronic acid. In short, the dissolution process breaks down alginate into smaller molecules that can be readily absorbed out of the blood stream and eliminated.

In addition to providing selective control over release of bioactive agents, EmboCaps provide a means of visually assessing location and rate of therapeutic factor release with Magnetic Resonance Imaging (MRI), computerized tomography (CT) or Ultrasound (US). Single or a combination of contrast agents may be added to the liquid alginate, liposome combination prior to polymerization to enable detection. Further, the unique liposome in alginate design enables the potential for incorporating a wider range of drug than in alginate alone as hydrophilic drugs can be incorporated within the liposome or in the alginate matrix and hydrophobic drugs can be incorporated into the lipid layer of the liposome.

Doxorubicin In Vitro Cell Toxicity Assay

To assess the release profile of doxorubicin from embocaps, 2 mL of EmboCaps was placed in 10 mL of normal saline in 15 mL falcon tube. Each day a 10 mL sample of supernatant was removed and stored at 5° C. After sample supernatant was collected, the entire volume of saline was aspirated and an additional 10 mL of normal saline was added to the cross-linked 3BrPa/EmboGel preparation. HepG2 cells were cultured in EMEM substituted with 2 mM L-Glutamine, 1 mM Sodium pyruvate, 0.1 mM non-essential amino acids, 1.5 g/L sodium bicarbonate and 10% FBS in a humidified CO2 incubator at 37° C. and a 5% CO2 atmosphere. Cells were cultured in tissue culture plates and culture media was replaced every 3 days. For each cell toxicity assay ten million HEPG2 cells were harvested and suspended in 5 mL of media. To this 5 mL, 1 mL of the EmboCap supernatant was added. For control experiments, the supernatant from non doxorubicin containing EmboCaps was added at the same concentration. Viability of the cells after above treatment was assessed with a standard trypan blue exclusion assay.

The formation of EmboCaps was assessed. Encapsulation of calcein containing liposomes or doxorubicin containing liposomes in the alginate core of Embocaps resulted in spheres of approximately 200 mm. The alginate matrix was stable in physiological solution for at least several months after synthesis. In FIG. 11, Panel a is a graph that shows the release profile of calcien from EmboCaps in the absence of EmboClear as measured by fluorescent intensity units in the solution in which EmboCaps were incubated. Panel b is a graph that shows the release profile of calcein from EmboCaps with the addition of EmboClear on day 10 showing rapis release of calcein. Panel c is an image of calcein containing EmboCaps. The data presented in FIG. 11 confirms that with the addition of EmboClear, capsules rapidly dissolve (>>30 sec.) into liquid components.

Release Profile of EmboCaps

Figure 11A:
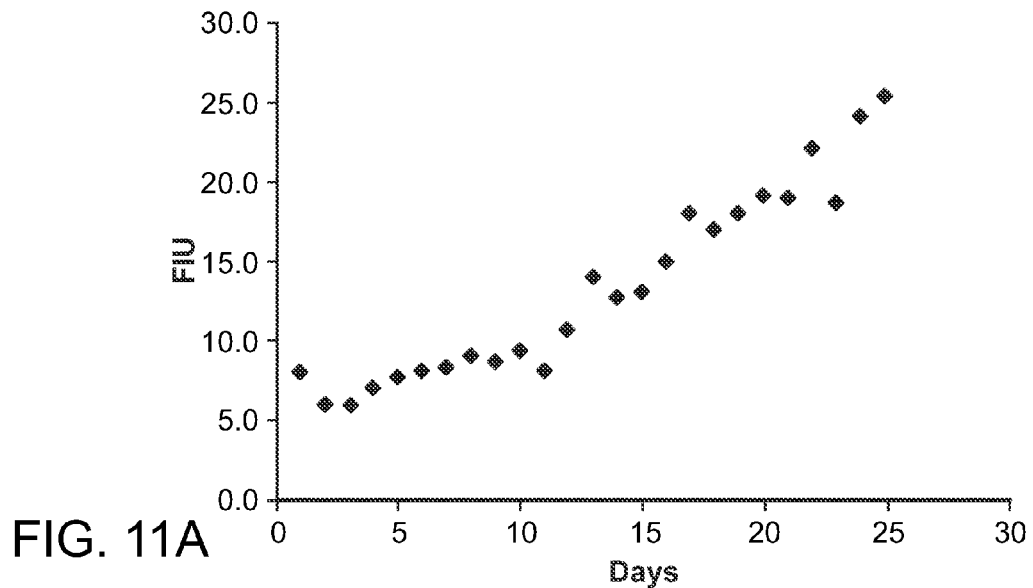
FIG. 11 (*a-c*) is three panels. Panel a is a graph that shows the release profile of calcien from EmboCaps in the absence of EmboClear as measured by fluorescent intensity units in the solution in which EmboCaps were incubated. Panel b is a graph that shows the release profile of calcein from EmboCaps with the addition of EmboClear on day 10 showing rapid release of calcein. Panel c is an image of calcein containing EmboCaps.
Figure 11B:
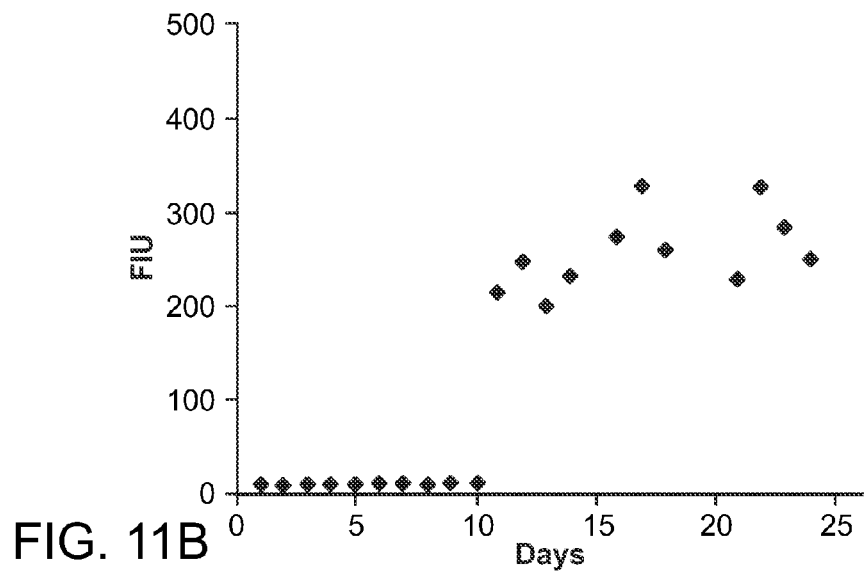
Figure 11C:
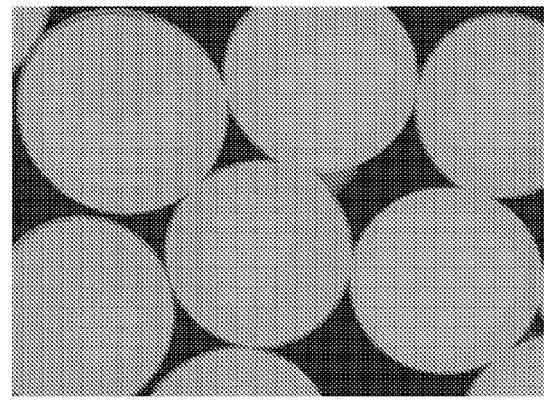

Assays conducted in vitro indicate that EmboCaps provide a sustained release of calcein over a period of 25 days in the absence of EmboClear (FIG. 11a). With addition of EmboClear, calcein is rapidly released (FIG. 11b) and EmboCaps are safely dissolved into non-toxic liquid by-products that can freely pass through the microvasculature and are rapidly cleared from the body.

Cell Toxicity Assay—Doxorubicin Release from EmboCaps

Figure 12:
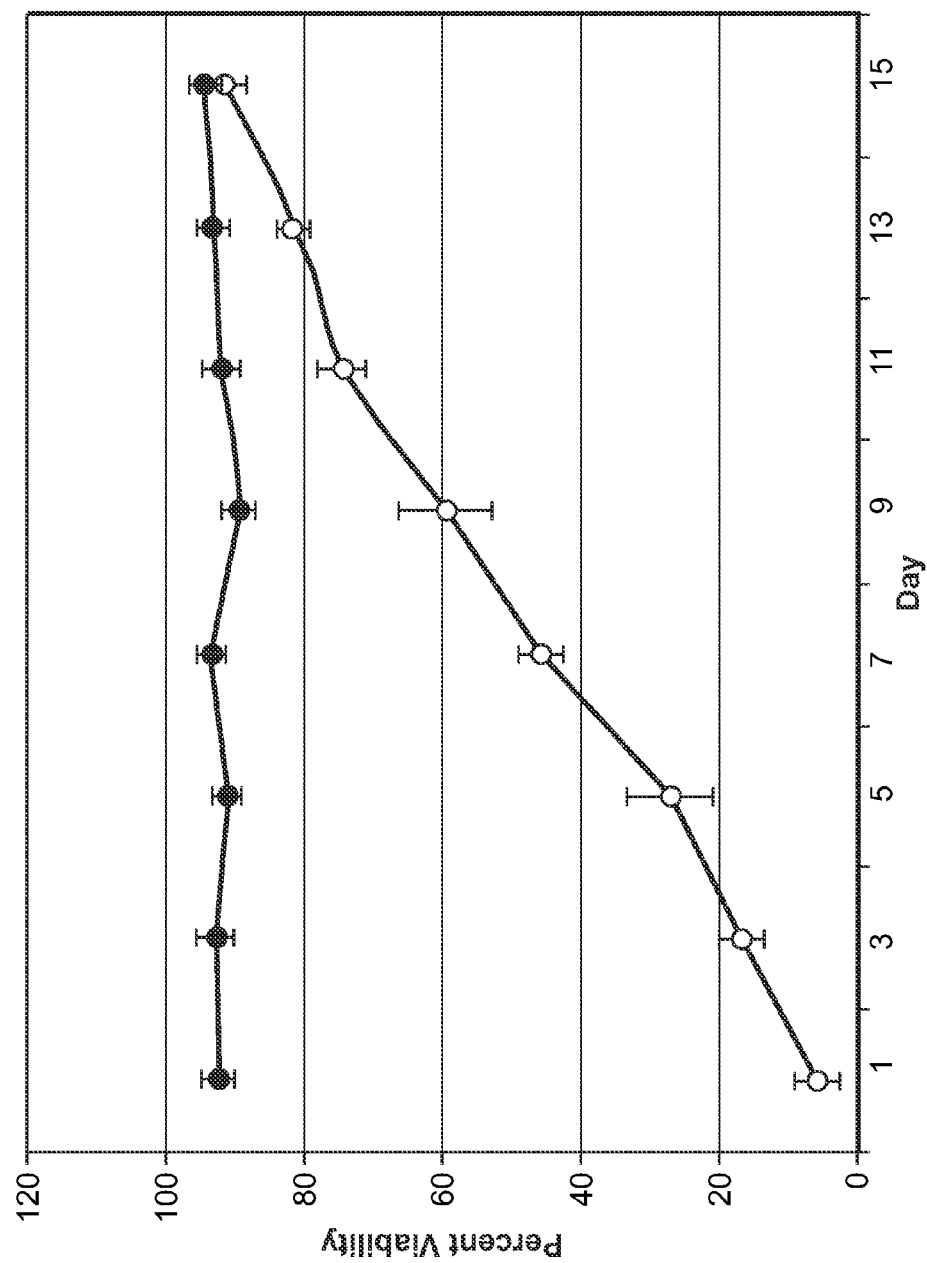
FIG. 12 is a graph that shows the percent viability of cells incubated with solution eluted from EmboCaps without doxorubicin (closed circles) and with doxorubicin (open circles). Static assay indicates that doxorubicin is released at a gradually decreasing concentration over a 15 day period. All points are an average of the ten different cell preparations treated with elution solution from ten separate EmboCap preparations.

In a static assay, EmboCaps released doxorubicin over a 15 day period as indicated by cytotoxicity assays with the HepG2 cell line (FIG. 12). With the addition of EmboClear, a rapid release of doxorubicin was achieved with complete dissolution of EmboCaps. The addition of contrast agents Feridex, Barium Sulfate, Barium Sulfate+Feridex, Barium Sulfate, Gold Nanoparticles, Perfluorooctylbromide or Perfluorocrownether did not interfere with the release of doxorubicin from EmboCaps as indicated by cytotoxicity assays. This is shown in Table 2, which shows the percent viability of cells incubated with solution eluted from EmboCaps without doxorubicin and without contrast (control), with doxorubicin and no contrast and with doxorubicin and the contrast agents/agents Feridex, Barium Sulfate, Barium Sulfate+Feridex, Gold, PFOB or PFPE.

TABLE 2

| Day | Control | No Contrast | Feridex | Barium | Barium + Feridex | Gold | PFOB | PFPE |
| --- | --- | --- | --- | --- | --- | --- | --- | --- |
| 1 | 91 ± 4 | 9 ± 3 | 8 ± 3 | 12 ± 3 | 13 ± 3 | 16 ± 3 | 16 ± 4 | 16 ± 3 |
| 3 | 92 ± 3 | 24 ± 6 | 22 ± 6 | 19 ± 5 | 26 ± 4 | 28 ± 4 | 25 ± 2 | 28 ± 3 |
| 5 | 93 ± 2 | 35 ± 5 | 31 ± 6 | 34 ± 4 | 41 ± 4 | 48 ± 5 | 35 ± 3 | 45 ± 5 |
| 7 | 91 ± 4 | 50 ± 3 | 52 ± 4 | 46 ± 7 | 54 ± 3 | 56 ± 4 | 56 ± 4 | 55 ± 3 |
| 9 | 92 ± 2 | 62 ± 4 | 72 ± 9 | 73 ± 4 | 73 ± 6 | 64 ± 4 | 75 ± 7 | 76 ± 6 |
| 11 | 93 ± 3 | 75 ± 4 | 78 ± 7 | 81 ± 6 | 78 ± 8 | 81 ± 3 | 86 ± 4 | 89 ± 2 |
| 13 | 94 ± 2 | 82 ± 4 | 89 ± 4 | 90 ± 2 | 89 ± 2 | 87 ± 5 | 89 ± 2 | 91 ± 2 |
| 15 | 94 ± 2 | 95 ± 2 | 93 ± 3 | 94 ± 3 | 93 ± 3 | 93 ± 2 | 96 ± 2 | 95 ± 3 |

Calcium-induced alginate gel beads have been developed in recent years as a unique vehicle for drug delivery system. These beads have been used in formulations as single or multiple units, with or without the addition of other hydrogels or polymers, intrapenetrating networks, nanospheres, polycations and many more dosage forms for achieving temporal and spatial drug release. The use of low molecular weight bioactive agents can benefit first from inclusions in liposomes before being incorporated into an alginate matrix if sustained release of the thereapeutic factor is to be achieved. For larger molecular weight bioactive agents such as Botox-A, direct inclusion in alginate is possible.

The advantage of encapsulating both contrast agent and therapeutic agents within the same delivery vehicle is that they are colocalized. This is important for correlating signal enhancement from the MR images with the spatial and temporal distribution of EmboCaps in patients. Release of bioactive agents can thus be indirectly followed by monitoring loss of contrast enhancement at the site of embolization.

In conclusion, EmboCaps are highly attractive for use in MR-guided targeted delivery of a broad range of therapeutic agents such as doxorubicin. EmboCaps procedure is specifically designed for complex and fragile bioactive molecules such as proteins, while the use of liposomes in conjunction with EmboCaps is designed for traditional small molecules and peptides. This delivery method is particularly attractive for intravascular delivery strategies as microcapsules can be used as embolic agents to create a reversible stasis thereby allowing a high payload of therapeutic agent to be delivered to a relatively well targeted area. Thus, there seems to be a potential for indirect drug monitoring through imaging.

Example 5

Treatment of Abdominal Aortic Aneurysm Endokleaks

In certain embodiments, alginate is used to treat vascular leakage. In the experiments described herein, alginate is a liquid embolic agent for treatment of Type II endoleaks with a Gore Excluder bifurcated stent in a silicone cast of a patient with Abdominal Aortic Aneurysm (AAA).

The management of type 2 endoleaks continues to be a source of controversy. Some physicians repair all type 2 endoleaks when they are detected on follow-up imaging, whereas others choose to follow patients with serial imaging and treat collateral endoleaks only when there is enlargement of the AAA. Embolization of a type 2 endoleak may be done with a transarterial or translumbar approach. Recent work suggests that embolization of the endoleak sac via a translumbar approach may be more durable than transarterial embolization of only the feeding vessel. Although most interventionalists use coils when embolizing type 2 endoleaks, there are a few reports of liquid embolic agents being used to treat endoleaks. Platinum and stainless-steel coils are safe and reliable embolic agents for endoleak embolization, but it can be time-consuming to embolize the entire endoleak sac with coils. In some situations, it can be impossible to embolize the endoleak sac and arteries that communicate with the endoleak with use of coils. A thick liquid embolic agent that offers some degree of control could be of value in endoleak embolization. For this reason, liquid embolic agents have been explored to achieve more complete filling. Liquid agents such as cyanoacrylates, polyvinyl alcohol particles, gel spheres, and precipitant gels have proven problematic in many regards. Some endovascular polymer "glues" have been shown to adhere to the vessel wall. Other polymer glues are difficult to control during injection. For example, glues quickly harden and may not flow optimally though the delivery microcatheter or may adhere the microcatheter to the vessel wall. In addition, many polymers (i.e., cyanoacrylates) and precipitant polymer solutions (i.e., dimethyl sulfoxide [DMSO]) are cytotoxic in their liquid form, which can lead to an undesirable immune response and tissue inflammation.

A liquid embolic agent, alginate, solves many of these problems as it is highly biocompatible and allows for controlled hardening as alginate remains a liquid until it is in the presence of a divalent cation such as calcium or barium. Liquid alginate embolic agents, such as EmboGel, can be used to quickly and safely embolize endoleaks. Specifically, as described herein, EmboGel can be used for the treatment of Type II endoleaks in patients with AAA.

Figure 13:
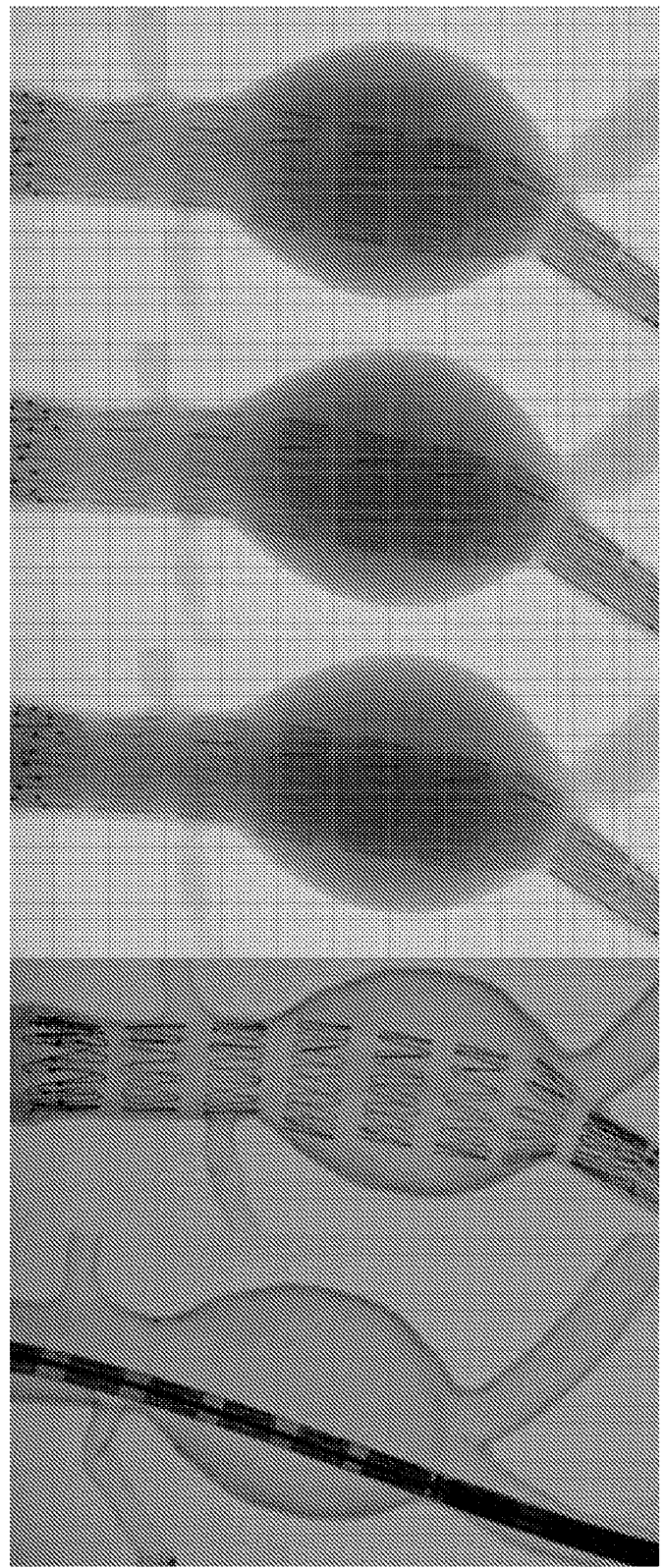
FIG. 13 is a photograph of an endoleak model system. A silicone AAA model (Elastrat) was connected to a pump for circulation of normal saline. A Zentith Aortic Stent Graft was then placed across the aneurysm and into the right iliac of the model. To simulate an endoleak model, ligatures were placed around the renal artery and the excluded left iliac of the model until only a slow fill of aneurysmal cavity was noted on a standard angio run.
Figure 14:
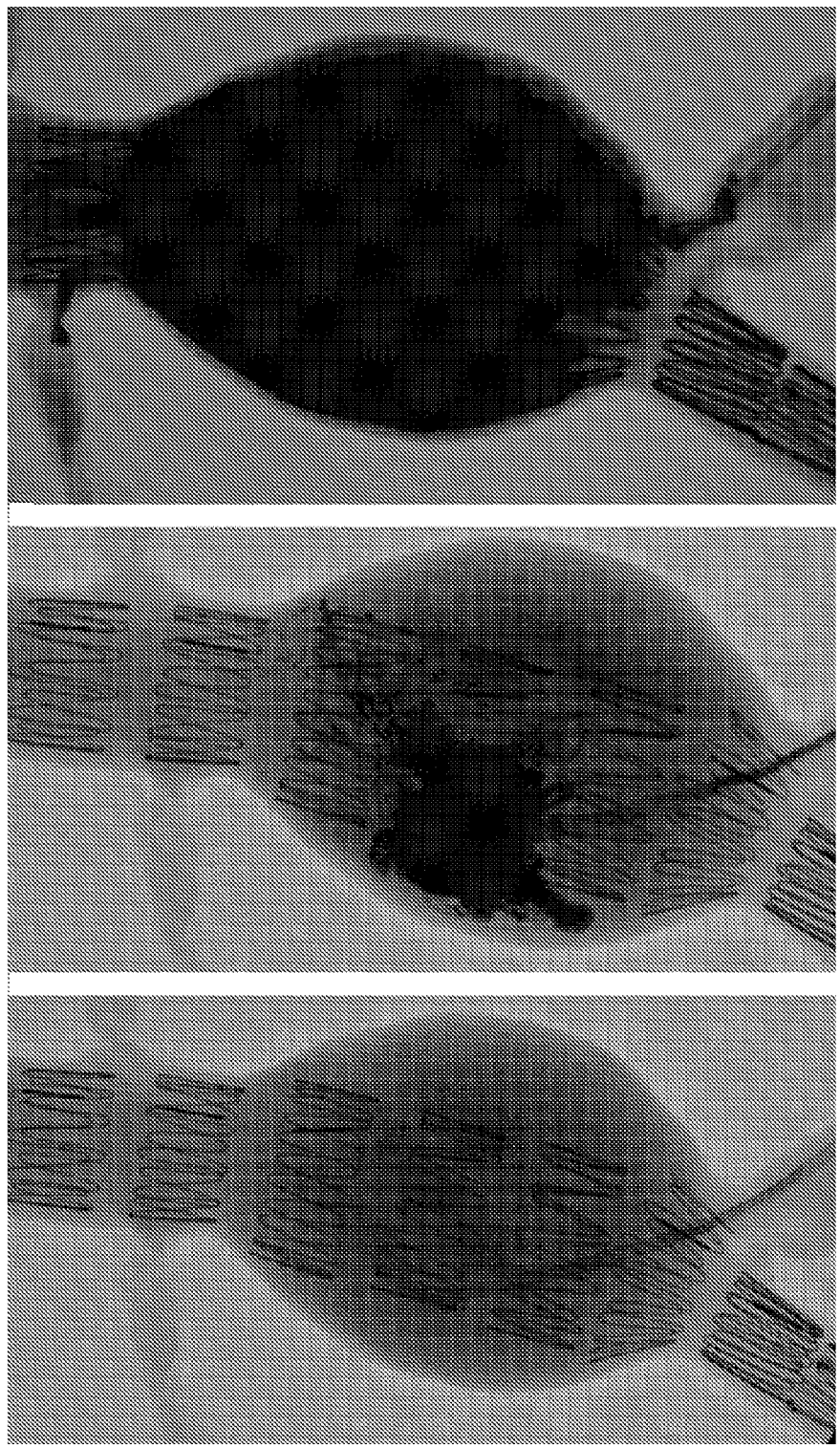
FIG. 14 is three panels of photographs showing a concentric catheter that was advanced through the excluded iliac. The middle panel shows EmboGel and Calcium chloride infused through respectively the inner and outer lumen of the concentric catheter. EmboGel was injected until maximal packing was achieved, shows in right hand panel.
Figure 15:
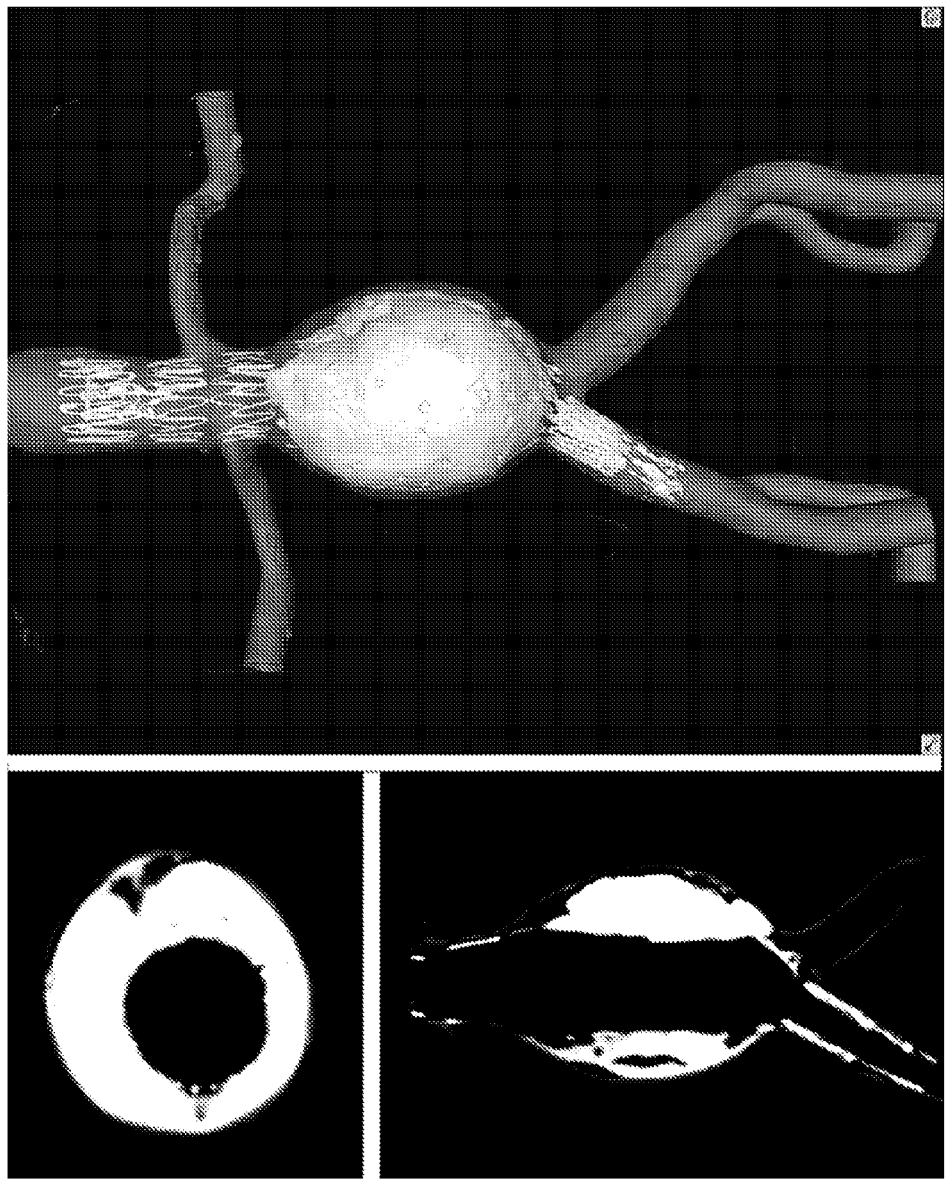
FIG. 15 is three panels of photographs showing CT evaluation of the model system, where EmboGel created a radiopaque mass that filled the aneurysmal cavity while the stent-graft kept the lumen of the vessel patent.

In one example, a silicone AAA model (Elastrat) was connected to a pump for circulation of normal saline. A Zentith Aortic Stent Graft was then placed across the aneurysm and into the right iliac of the model (FIG. 13). To simulate an endoleak model, ligatures were placed around the renal artery and the excluded left iliac of the model until only a slow fill of aneurysmal cavity was noted on a standard angio run (FIG. 13). A concentric catheter was then advanced through the excluded iliac and EmboGel and Calcium chloride were infused through respectively the inner and outer lumen of the concentric catheter. EmboGel was injected until maximal packing was achieved (FIG. 14). As evidence by CT evaluation of the model, EmboGel created a radiopaque mass that filled the aneurysmal cavity while the stent-graft kept the lumen of the vessel patent (FIG. 15). This approach would also be possible using a birfurcated stent-graft that has been placed across a AAA.

Example 6

Use of EmboGel for the Treatment of Osteoporosis

EmboGel has use in the treatment of osteoporosis. The experiments described herein demonstrate the injection of EmboGel with osteogenic factors or cells into vertebrae for treatment of osteoporosis. Percutaneous vertebroplasty (PVP) has been shown to provide benefit to patients with painful vertebral compression fractures in terms of both pain control and disability resolution. Patients typically demonstrate rapid and durable pain relief and often regain lost function. Despite the demonstrated benefit, there is debate about whether vertebroplasty also increases fracture morbidity by either inducing or facilitating subsequent vertebral fractures New studies such as those reported by Trout et al. (New Fractures after Vertebroplasy: Adjacent Fractures Occur Significantly Sooner. AJNR 27:217-23 (2006)) have demonstrated an association between vertebroplasty and new vertebral fractures. Specifically, following vertebroplasty, patients are at increased risk of new-onset adjacent-level fractures and, when these fractures occur, they occur sooner than non-adjacent level fractures.

The use of EmboGel may facilitate a new method of treating osteoporosis prior to vertebral compression. The advent of new imaging techniques with clinical grade CT (computerized tomography or CAT scan) and MRI units has enabled the identification of osteoporotic vertebrae prior to compression fractures. Such vertebrae could be prophylacticaly injected with EmboGel containing osteogenic factors such as Wnt and Bone Morphogenetic Protein 2 (BMP-2) to cause new bone growth and thus prevent compression factors.

In another embodiment, cells that produce these factors could be added to EmboGel. Such a technique was shown by Zachos et al. in an animal model of articular fracture (Zachos et al. Mesenchymal stem cell-mediated gene delivery of bone morphogenic protein-2 in articular fracture model. Molecular Therapy May 2007). The Embogel/Emboclear solution provides a clear advantage over the alginate used by Zachos et al as it can be dissolved if complications occur and can be seen with standard clinical grade fluoroscopy units. This feature is especially important as over injection of bone cements and other polymers has been shown to cause cord compression.

Figure 16:
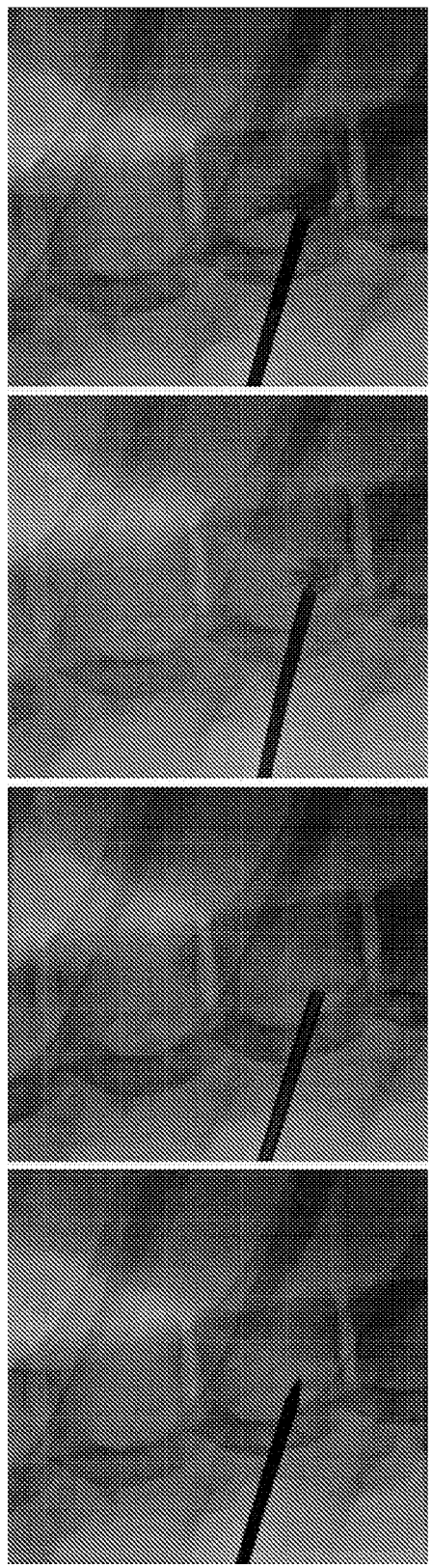
FIG. 16 is four panels of photographs showing Embogel injected under fluoroscopic guidance into the verterbrae of a New Zealand white rabbit.

In the experiments described herein, Embogel was injected under fluoroscopic guidance into the verterbrae of a New Zealand white rabbit (FIG. 16). Embogel was injected through a modified vertebroplasty needle with a dual lumen for injection of EmboGel through the inner lumen and injection of calcium chloride through the outer lumen. As shown in FIG. 16, EmboGel injected at one site was able to spread within the vertebrae and was easily detectable with a clinical-grade fluoroscopic unit.

Experiments were performed in rabbits. In certain experiments, in a New Zealand white rabbit 5 mL of bone marrow is drawn into a 20-mL syringe with an 18-gauge needle. After the bone marrow is collected it is be mixed with an equal volume of PBS to homogenize thoroughly until all blood clots are dissociated. The cell suspension is then centrifuged for 10 min at 900 g. The supernatant is then aspirated and the pellet resuspended in PBS to a final density of 4×10$^7$ nucleated cells/mL. The cell suspension is then layered over a 1.073 g/mL Percol solution and the preparation centrifuged at 900 g for 30 min. The middle phase of the resulting three phases is collected and centrifuged again for 10 min at 1000 rpm. The supernatant is removed and the pellet resuspended in 1 mL of PBS. The preparation is then centrifuged again and the supernatant removed. The cells are incubated at 5% C02 and 37° C., and the medium is changed every 3 days. To induce osteogenic differentiation, culture medium was supplemented with ascorbic acid (100 mM), b-glycerophosphate (10 mM) and dexamethasone (10-7 M). Once differentiation occurs, cells were added to EmboGel at a concentration of 1×10$^6$ cells per mL of EmboGel.

Example 7

Intratumoral Delivery of EmboGel for Thermal Ablation

Described herein is targeted intratumoral delivery of EmboGel containing iron oxides in conjunction with apparatus for creating an alternating magnetic field for thermal ablation.

Iron oxide conjugated with antibodies have recently been explored for thermal ablation of tumors. (Denardo S, et al. Thermal dosimetry predictive of efficacy of 111In-ChL6 Nanoparticle AMF-Induced Thermoablative Therapy for Human Breast Cancer in Mice. J. Nucl Med 2007; 48:437-444). Specifically an antibody specific for a particular tumor is conjugated to an iron oxide and injected systemically into a patient and over time due to antibody specificity iron oxides accumulate at the site of the tumor masses. By placing the subject in an apparatus that creates an alternating magnetic field the iron particles heat thus ablating the cancer tissue. This approach for treating metastatic tumors has significant limitations for treating well-localized tumor masses. In one particular embodiment, a preferred method may involve the injection of EmboGel containing iron oxides intratumoraly, and thereby localizing iron oxide within the tumor bed. If a similar alternating magnetic field is applied, a homogenous heat will be applied to the tumor bed. This technique could prove superior to the probe based technique already employed for ablation of well localized masses as the heat applied will be homogenous across the tumor bed.

Figure 17:
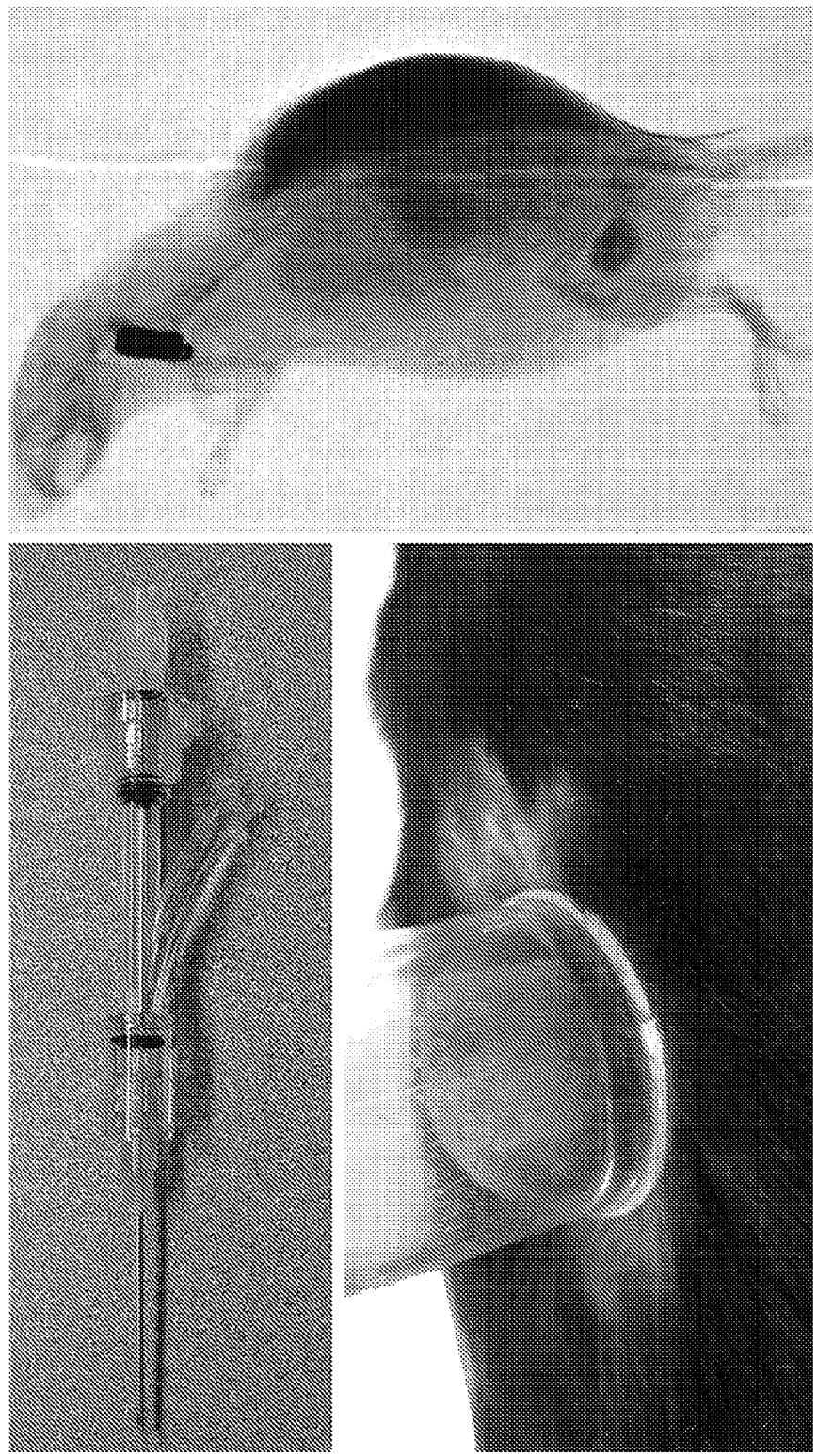
FIG. 17 is three panels of photographs showing EmboGel was injected in a well localized mass on the back of a mouse with a concentric needle system, shown in the top panel. EmboGel was injected through the central lumen and calcium chloride injected through the outer lumen of the concentric needle system.

In one example, EmboGel was injected in a well localized mass on the back of a mouse with a concentric needle system. EmboGel was injected through the central lumen and calcium chloride was injected through the outer lumen (FIG. 17). By incorporating iron oxides (Feridex, Berlex) as well as iohexyl into EmboGel, delivery of the iron oxide agent was assessed with standard clinical grade fluoroscopy. EmboGel effectively localized contrast to the injected area.

Further uses of EmboGel include the followup of intratumoral injection of iron oxide containing EmboGel with MRI pre and post application of an alternating magnetic field to assess distribution of the iron oxides. Further, Embogel containing iron oxides could be pregelled with a solution of calcium chloride or barium chloride in the form of microcapsules for intravascular delivery to the site of the tumor followed by the application of an alternating magnetic field.

Example 8

Method of Synthesis of Dissolvable Wound Dressing

Figure 18:
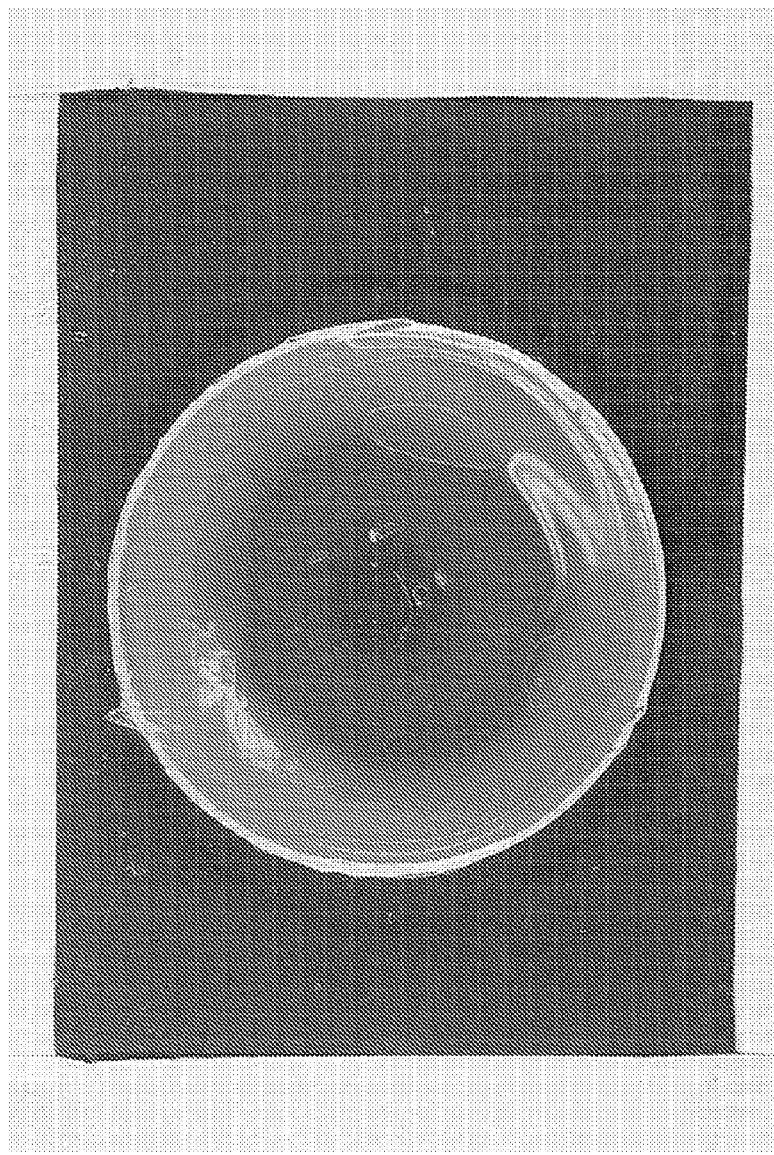
FIG. 18 shows a dissolvable alginate wound dressing.

Described is a novel method of synthesis of a dissolvable wound dressing. To prepare the dissolvable wound dressing a 0.25% w/v alginate solution is prepared. Calcium carbonate is added at a concentration of 10% w/v. Place the alginate solution with undissolved calcium carbonate into a rotovaporator with vacuum on lowest setting. Rotate solution until the desired thickness of alginate film forms on the wall of the rotating flask. When the desired film is achieved add water to rinse away excess calcium carbonate. The polymerized alginate gel can then be removed from the flask in a hydrated state (FIG. 18) or alternatively the rotovaporator can be left with vacuum on medium power to create a dried calcium alginate sheet.

In a second method, to create a calcium alginate impregnated wound dressing an absorbent pad is soaked in an aqueous solution of sodium alginate (1-10% sodium alginate). The saturated pad is then placed in an aqueous bath containing 1-10% calcium chloride to convert the sodium alginate to calcium alginate. The pad is then removed from the calcium chloride bath and the pad with polymerized calcium alginate is then washed with deionized water. After washing, the dressing can be dryed in a vacuo or by passing between heated rollers and thereafter softening mechanically to provide the finished alginate-impregnated absorbent dressing, as described in U.S. Pat. No. 5,470,576, incorporated in its entirety herein.

In a third method, the PEC membranes were prepared as previously described (Wang et al. 2001). Briefly, 25 ml each of chitosan (0.25% w/v in 1:1 v/v of 2% acetic acid and acetone) and alginate (0.25% w/v in distilled water) solutions were gradually mixed with manual stirring at ambient temperature for 1 h. The coacervates were pelleted by centrifugation for 10 min at 3000 rpm, washed three times with water, and resuspended in 20 ml of distilled water. Known volumes, 0.5 to 0.7 ml, of 2% w/v CaCl2 solution was added, and the mixture was stirred for 1 h. The mixture was then cast in a 85-mm Petri dish and dried for 30 h under ambient conditions to yield the homogeneous PEC membranes. Membranes were stored in desiccators at ambient conditions. Smart Skin is a dressing for split-thickness skin-graft. Similar to Allevyn (Smith & Nephew), in a certain embodiment Smart Skin has an hydrophilic inner layer consisting of a collagen, calcium alginate mixture. Applied to the hydrophilic inner layer is an outer polyurethane waterproof film layer that prevents bacterial contamination and maintains a moist wound environment. Smart Skin provides a unique advantage over Allevyn as the inner hydrogel layer can be selectively dissolved with EmboClear. This overcomes the major drawback of Allevyn, namely its propensity to strongly adhere to the wound bed causing mechanical trauma to the newly formed delicate epithelium when the dressing is changed.

Smart Skin can be impregnated with nanocrystalline silver particles (10 nm from Nanocs) by directly dissolving the alginate at a concentration of 2% w/v in a 0.01% Ag aqueous solution prior to polymerization. In certain embodiments larger silver nanoparticles are preferable (20-50 nm Nanocs). Additionally, collagen, hyaluronic acid or an alternate biodegradeable biomaterial may be added to the silver alginate solution prior to polymerization with calcium or an alternate divalent cation. In addition to directly incorporating silver nanoparticles in the inner alginate layer, in an alternate formulation the outer layer can consist of a silver-coated high density polyethelene mesh similar to Acticoat (Smith and Nephew).

Alternate compound that can be incorporated into the alginate matrix of Smart Skin to promote keratinocyte growth include M4 agonists, M3 antagonists, basic fibroblast growth factor (bFGF), keratinocyte growth factor (KGF), WNTs, Keratinocyte growth factor-2 (KGF-2). These agents may be directly incorporated into the alginate layer prior to polymerization or in certain embodiments may first be entrapped in liposomes that are then added to the liquid alginate layer prior to polymerization. This unique combination of liposome impregnated hydrogel scaffold ensures a slow release of hydrophilic compounds as demonstrated by the release of doxorubicin from liposomes in EmboCaps previously described in this patent.

In alternate embodiments, alginate can be act as a component of a full-thickness skin scaffold. In certain embodiments in which alginate is combined with other biomaterials such as collagen, hyaluronic acid or PEGDA, EmboClear can be added to selectively dissolve the alginate component of the scaffold. This potentially would enable ease of removal of an infected tissue scaffold or alternatively would give the clinician selective control over the porosity of the scaffold thereby facilitating tissue ingrowth. In addition, the skin scaffold can be seeded with a number of cell sources including In another embodiment, the agent is a cell secreting a therapeutic factor. In another particular embodiment of the method, the cell secreting a therapeutic factor is selected from the group consisting of: autogenic or allogenic fibroblasts, endothelial cells, transgenic cells, mesenchymal stem cells, embryonic stem cells, extraembryonic stem cells, embryonic germ cells, umbilical stem cells, pluripotent and multipotent stem cells, endothelial cells, dendritic cell, hematopoietic stem cells, sertoli cells, xenogenic cell sources of all listed above, skin cells, adipocytes, skin-derived stem cells, neural stem cells, glial progenitor cells, oligodendrocyte precursors, oligo precursors, fat stem cells, other stem cells sources such as from amniotic fluid, baby teeth, bone marrow cells, cord blood, placental blood, fat tissue, fetal cells and breast.

Example 9

Pulmonary Applications of EmboGel

Figures 20A, 20B, 20C:
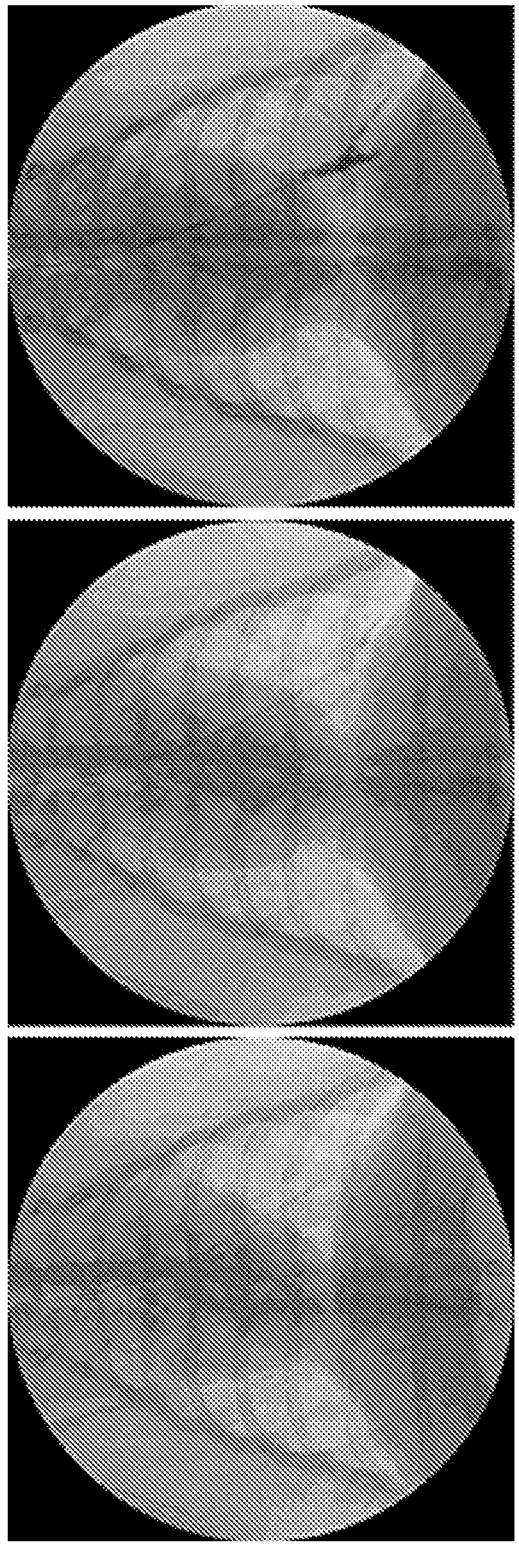
FIG. 20 (*a-c*) is three panels. Panel a) shows an over injection of EmboGel (total injection of 0.8 mL of EmboGel). Panel b) shows fluoroscopic image indicating dissolution of EmboGel after delivery of 1 mL of EmboClear. Panel c) Shows fluoroscopic image after suction through 5 french catheter indicating loss of all EmboGel except for a small piece in a terminal segment (white arrow).

EmboGel can also be used for pulmonary applications. Lung volume reduction therapy refers to the elimination of emphysematous hyperinflated lung through surgical means or lung volume reduction through minimally invasive techniques. In this example, EmboGel was utilized to exclude a lung segment in a New Zealand White rabbit. A 5 frecnh dual lumen catheter was advanced in the endotracheal tube under fluoroscopy guidance and was advance to a distal lung segment (FIG. 19a). Upon proper catheter placement 0.1 mL of EmboGel and 0.1 mL of calcium chloride was delivered (FIG. 19b). An addition 0.4 mL of EmboGel and 0.4 mL of calcium chloride for a total volume of 0.5 mL of EmboGel delivered (FIG. 19c). The animal was placed back on a respirator and the movement of EmboGel was assessed. Over a 30 minute period EmboGel remained well localized in the lung segment in which it was delivered. The dual lumen 5 French catheter was once again advanced through the endotracheal tube to the previous position and an additional 0.2 mL of EmboGel was delivered (FIG. 20a). To assess the ability for EmboClear to dissolve excess EmboGel, 1 mL of EmboClear prepared as previously described was delivered through the calcium channel lumen of the concentric catheter system (FIG. 20b). After 1 minute, suction was applied to the lumen through which the EmboClear was injected and the now liquid contents of the lung were removed. X-ray fluoroscopy demonstrated rapid clearance of the majority of EmboGel with the exception of a small piece of EmboGel in a distal segment of the lung (FIG. 20c white arrow). In addition to occlusion of lung segments EmboGel could be used with CT-fluoroscopy guided injection to provide a reliable marker for the localization of pulmonary nodules, especially in those patients with severe anthracosis in the pulmonary parenchyma. EmboGel could also be used in conjunction with coils or alone as a method for closing persistent bronchopleural fistulas. In the case of conjunctive use with coils, the coils would serve as scaffolding for EmboGel. Another potential pulmonary use of EmboGel is to stop air leaks after lung resection.

Example 10

Loco-Regional Delivery of Botulinum Toxin

Encapsulation of Botolinum Toxin (Bo-Caps) and Sodium Morrhuate

EmboCaps or EmboGel could potentially be used for the release of numerous bioactive agents. As proof of principle the release of Botulinum Toxin A (Btx A, Allergan Pharmaceuticals)) from EmboCaps. Over the last 30 years, Btx A has been affectively used for a variety of clinical conditions in neurology (torticollis, laryngeal dystonia, tremors), opthalmology (strabismus, lateral rectus muscle paralysis, nystagmus) and gastroenterology (achalasia, sphincter of oddi dysfunction, anal fissures. Botox in EmboGel or EmboCaps could serve as a depot for a sustained release of botulinum toxin over an extended period of time. In addition, the ability to visualize encapsulated botulinum toxin would allow for targeted delivery and maximize loco-regional release. The nature of botoulinum toxin requires that a gentle, aqueous microencapsulation process be employed. The most frequently studied method of aqueous microencapsulation involves ionotropic gelation of alginate using multivalent ions, particularly calcium. To form BoCaps, 1.5 mL of 2% w/v ultrapurified sodium Protanal" HF alginate from FMC Biopolymers (Haugesund, Norway) is added to 500 units of botulinum toxin (Dysport, Speywood Pharmaceuticals). This dosage is currently the effective dosage used in clinical trials for loco-regional delivery to the gastric wall. The mixture is then vortexed until a homogenous suspension is created. The alginate botox suspension is then loaded into a 1 cc tuberculin syringe fitted with a 25 gauge blunt tip needle. A Petri dish, containing isotonic (1.70%) calcium chloride dihydrate, is placed under the needle. A stainless wire is immersed in the calcium solution and connected to a ground. The current is adjusted by changing the van de Graaff belt speed. The botox/alginate solution is passed through the needle with a flow rate of about 200 ul/min using a nanoinjector pump. After extrusion of alginate/botox, resulting microcapsules are collected in a solution of 100 mM $CaCl_2$ that complexes with the alginate to form stable capsules. Capsules are then washed three times with normal saline to remove any free botox. These gelled droplets are suspended in 0.05% poly-L-lysine (Sigma, molecular mass=22-24 kDa) for 2 min. After incubation, capsules are washed once again in normal saline to remove any free pol-L-lysine. Using this technique, encapsulation of various dosages of Botulinum Toxin A is feasible into variable number of capsules.

Permeability of EmboCaps to Fluorescent Lectins

One of the more interesting aspects of microencapsulation using alginate is the ability to coat the microcapsule with polycations such as poly-1-lysine and poly-1-ornithine. The conventional alginate microcapsules involve an alginate core coated with poly-1-lysine followed by another coat of alginate. The poly-1-lysine serves to provide structural integrity to the capsule and also provides a semipermeable membrane which can regulate the diffusion of materials into and out of the alginate microcapsule. The size exclusion characteristics of the coating, specifically poly-1-lysine, have been studied and are dependent on the molecular weight of the coating, concentration of poly-1-lysine in the coating solution, and the time of the coating process. In order to determine the permeability of PFC containing microcapsules compared to non-contrast containing capsules, microcapsule preparations were incubated with one of four fluorescently labeled lectins of varying molecular weight. Lectin incubation consisted of either incubation with 15 L (1 mg/L) of FITC-*Triticum vulgare* (WGA, molecular mass=36 kDa), FITC-*Maackia amurensis* I (MAL-I, molecular mass=75 kDa), FITC-*Ricinus communis* (RCA-I, molecular mass=120 kDa), or FITC-*Sambuca nigra* (SNA, molecular mass=150 kDa). All lectins were obtained from EY Lab Inc., except FITC-*Maackia amurensis* I (Vector laboratories). Capsules were incubated for 48 h at 4° C. on a mechanical rocker, after which they were examined microscopically (Olympus X51 and IX71 epifluorescence microscopes equipped with an Olympus DP-70 digital acquisition system) following embedding with Vectashield mounting medium (Vector, Burlingame, Calif.). The results are shown in Table 3, below.

TABLE 3

| | Alginate + PLL (<2 min incubation) | Alginate + PLL + Alginate (5 min incubation) | Alginate + PLL (>10 min incubation) |
|---|---|---|---|
| 36 kD | ✓ | ✓ | ✓ |
| 75 kD | ✓ | ✓ | ✓ |
| 120 kD | ✓ | ✓ | X |
| 150 kD | ✓ | X | X |

Figure 21:
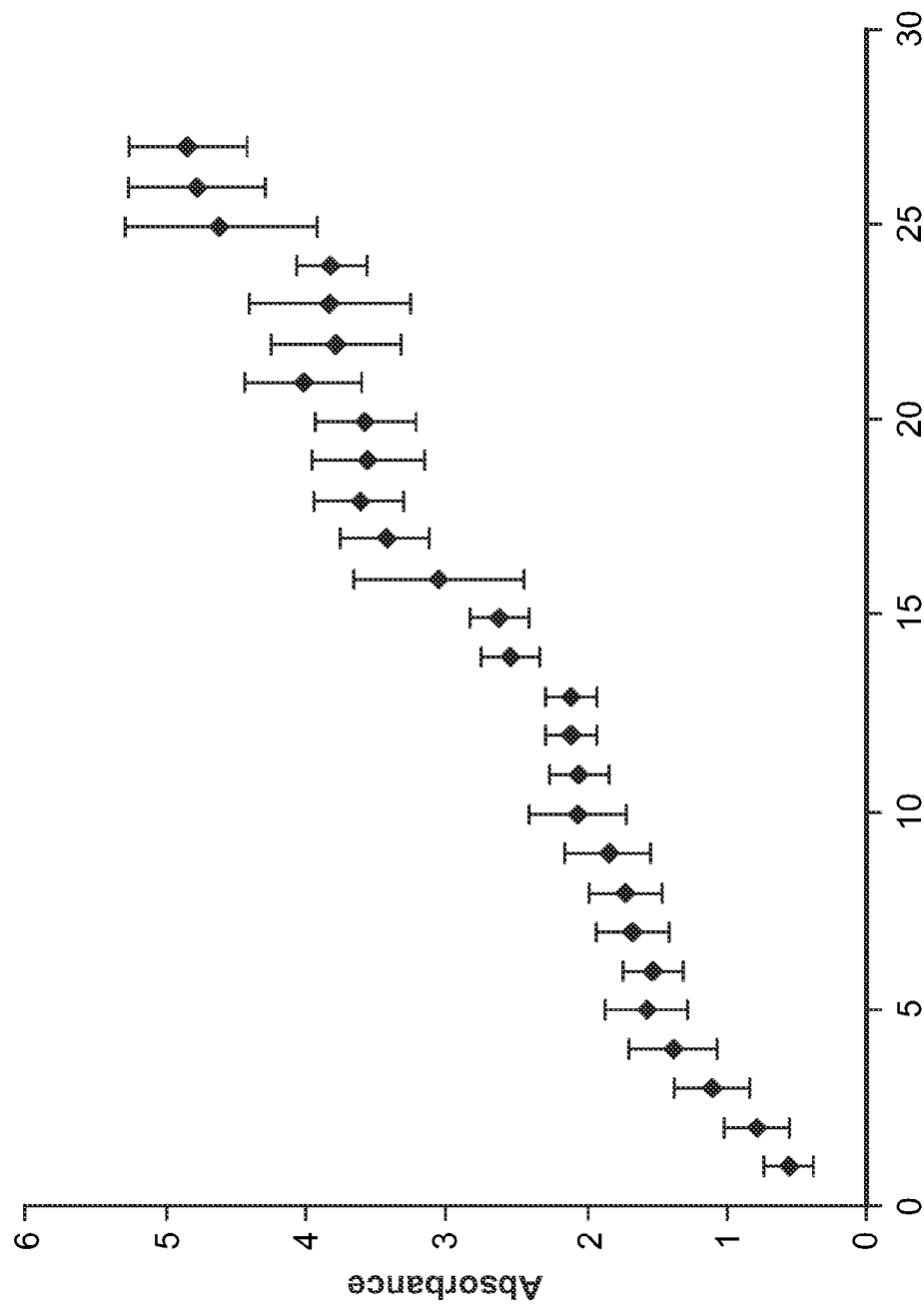
FIG. 21 is a graph showing Botox release from BoCaps measured by spectrophotometric analysis. Specifically, 1 mL of BoCaps was suspended in 20 mL of normal saline. To assess release profile over time, botox capsules were gently pelleted and a sample of supernatant was removed edaily for spectrophotomoteric analysis. The concentration of Botox in the supernatant was measured using a NanoDrop ND-1000 spectrophotomoter with absorbance set at 250 nm and an extinction coefficient of 22 L/gm-cm.

Elution Profile of Encapsulated Botulinum Toxin A (Bo-Caps) and Sodium Morrhuate To demonstrate the elution and release, botulinum toxin A (100 Units, Botox, Allergan Pharmaceuticals) were encapsulted into 10,000 magnetocapsules which compromised 10 cc of volume. After saline washing was performed, the capsules containing Botulinum toxin (Bo-Caps) underwent systemic sampling with spectrophotometer, over a 30 day period (FIG. 21).

Western Blot of Botox-A

Total protein (50 μg/lane) was fractionated by electrophoresis on 7% polyacrylamide gels under non-denaturing conditions, transferred onto nitrocellulose membranes, blocked for 2 h in phosphate-buffered saline (PBS) containing 5% dried skimmed milk powder, and then probed overnight at 4° C. with anti-BotoxA Heavy Chain Monoclonal Antibody (AbCam) diluted 1:1,000. After repeated washings, the membranes were incubated at room temperature for 1 h with horseradish peroxidase-conjugated rabbit anti-mouse IgG (Jackson) diluted 1:1,000. Specific antibody binding was visualized by exposing X-ray film to the membrane. The density of the scanned protein bands was calculated using Image J software (NIH, Bethesda Md.).

Western blot for the heavy chain of Botox-A in the supernatant of EmboCaps revealed that the heavy chain was not denatured (FIG. 22a). Assessment of band intensity revealed that Botox-A was slowly released in the absence of EmboClear (FIG. 22b). The results from the western blot show that the protein was neither degraded nor did it aggregate during the preparation. This was also true for the entire duration of release and after addition of EmboClear on day 12.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCES

1. Gailloud P. Endovascular treatment of cerebral arteriovenous malformations. Tech Vasc Intery Radiol. 2005; 8:118-128.
2. Howington J U, Kerber C W, Hopkins L N. Liquid embolic agents in the treatment of intracranial arteriovenous malformations. Neurosurg Clin N Am. 2005; 16:355-63, ix-x.
3. Taki W, Nishi S, Yamashita K, et al. Selection and combination of various endovascular techniques in the treatment of giant aneurysms. J Neurosurg. 1992; 77:37-42.
4. Mandai S, Kinugasa K, Ohmoto T. Direct thrombosis of aneurysms with cellulose acetate polymer. Part I: Results of thrombosis in experimental aneurysms. J Neurosurg. 1992; 77:497-500.
5. Kinugasa K, Mandai S, Terai Y, et al. Direct thrombosis of aneurysms with cellulose acetate polymer. Part II: Preliminary clinical experience. J Neurosurg. 1992; 77:501-507.
6. Nishi S, Taki W, Nakahara I, et al. Embolization of cerebral aneurysms with a liquid embolus, EVAL mixture: report of three cases. Acta Neurochir (Wien). 1996; 138:294-300.
7. Molyneux A J, Cekirge S, Saatci I, Gal G. Cerebral Aneurysm Multicenter European Onyx (CAMEO) trial: results of a prospective observational study in 20 European centers. AJNR Am J Neuroradiol. 2004; 25:39-51.
8. Weber W, Siekmann R, Kis B, Kuehne D. Treatment and follow-up of 22 unruptured wide-necked intracranial aneurysms of the internal carotid artery with Onyx HD 500. AJNR Am J Neuroradiol. 2005; 26:1909-1915.
9. Dudeck O, Jordan O, Hoffmann K T, et al. Intrinsically radiopaque iodine-containing polyvinyl alcohol as a liquid embolic agent: evaluation in experimental wide-necked aneurysms. J Neurosurg. 2006; 104:290-297.
10. Mottu F, Gailloud P, Massuelle D, Rufenacht D A, Doelker E. In vitro assessment of new embolic liquids prepared from preformed polymers and water-miscible solvents for aneurysm treatment. Biomaterials. 2000; 21:803-811.
11. Piotin M, Mandai S, Murphy K J, et al. Dense packing of cerebral aneurysms: an in vitro study with detachable platinum coils. AJNR Am J Neuroradiol. 2000; 21:757-760.
12. Soga Y, Preul M C, Furuse M, Becker T, McDougall C G. Calcium alginate provides a high degree of embolization in aneurysm models: a specific comparison to coil packing. Neurosurgery. 2004; 55:1401-9; discussion 1409.

13. Piotin M, Mandai S, Sugiu K, Gailloud P, Rufenacht D A. Endovascular treatment of cerebral aneurysms: An in vitro study with detachable platinum coils and tricellulose acetate polymer. AJR Am J Roentgenol. 2001; 176:235-239.
14. Murayama Y, Vinuela F, Tateshima S, Vinuela F J, Akiba Y. Endovascular treatment of experimental aneurysms by use of a combination of liquid embolic agents and protective devices. AJNR Am J Neuroradiol. 2000; 21:1726-1735.
15. Yang X, Wu Z, Li Y, et al. Re-evaluation of cellulose acetate polymer: angiographic findings and histological studies. Surg Neurol. 2001; 55:116-122.
16. Cekirge H S, Saatci I, Ozturk M H, et al. Late angiographic and clinical follow-up results of 100 consecutive aneurysms treated with Onyx reconstruction: largest single-center experience. Neuroradiology. 2006; 48:113-126.
17. Norbash A M, Singer R J. Videographic assessment of the embolic characteristics of three polymeric compounds: ethylene vinyl alcohol, cellulose acetate, and liquid urethane. AJNR Am J Neuroradiol. 2001; 22:334-340.
18. investigators n-BCAt. N-butyl cyanoacrylate embolization of cerebral arteriovenous malformations: results of a prospective, randomized, multi-center trial. AJNR Am J Neuroradiol. 2002; 23:748-755.
19. Chaloupka J C, Vinuela F, Vinters H V, Robert J. Technical feasibility and histopathologic studies of ethylene vinyl copolymer (EVAL) using a swine endovascular embolization model. AJNR Am J Neuroradiol. 1994; 15:1107-1115.
20. Chaloupka J C, Huddle D C, Alderman J, Fink S, Hammond R, Vinters H V. A reexamination of the angiotoxicity of superselective injection of DMSO in the swine rete embolization model. AJNR Am J Neuroradiol. 1999; 20:401-410.
21. Brothers M F, Kaufmann J C, Fox A J, Deveikis J P. n-Butyl 2-cyanoacrylate—substitute for IBCA in interventional neuroradiology: histopathologic and polymerization time studies. AJNR Am J Neuroradiol. 1989; 10:777-786.
22. Jahan R, Murayama Y, Gobin Y P, Duckwiler G R, Vinters H V, Vinuela F. Embolization of arteriovenous malformations with Onyx: clinicopathological experience in 23 patients. Neurosurgery. 2001; 48:984-95; discussion 995-7.
23. Raymond J, Metcalfe A, Desfaits A C, et al. Alginate for endovascular treatment of aneurysms and local growth factor delivery. AJNR Am J Neuroradiol. 2003; 24:1214-1221.
24. Becker T A, Preul M C, Bichard W D, Kipke D R, McDougall C G. Calcium alginate gel as a biocompatible material for endovascular arteriovenous malformation embolization: six-month results in an animal model. Neurosurgery. 2005; 56:793-801; discussion 793-801.
25. Becker T A, Kipke D R, Preul M C, Bichard W D, McDougall C G. In vivo assessment of calcium alginate gel for endovascular embolization of a cerebral arteriovenous malformation model using the Swine rete mirabile. Neurosurgery. 2002; 51:453-8; discussion 458-9.
26. Altes T A, Cloft H J, Short J G, et al. 1999 ARRS Executive Council Award. Creation of saccular aneurysms in the rabbit: a model suitable for testing endovascular devices. American Roentgen Ray Society. AJR Am J Roentgenol. 2000; 174:349-354.
27. Trout, A. T., Kallmes D. F., Kaufmann T. J. New Fractures after Vertebroplasy: Adjacent Fractures Occur Significantly Sooner. AJNR 27:217-23 (2006).
28. Zachos T, Diggs A, Weisbrode S, Bartlett J, Bertone A. Mesenchymal stem cell-mediated gene delivery of bone morphogenic protein-2 in articular fracture model. Molecular Therapy May 2007.
29. Denardo S, Denard G, Natarajan A, Mires L, Foreman A, Gruettner C, Adamson G, Ivkov R. Thermal dosimetry predictive of efficacy of 111In-ChL6 Nanoparticle AMF-Induced Thermoablative Therapy for Human Breast Cancer in Mice. J. Nucl Med 2007; 48:437-444.
30. Wang L S, Khor E, Lim L Y, Chitosan-alginate-CaCl2 system for membrane coat application. J Pharm Sci 2001; 90: 1134-1142.

What is claimed is:

1. A method for dissolving a purified alginate gel crosslinked with a divalent cation in a subject, the method comprising:
   contacting in the subject the purified alginate gel crosslinked with a divalent cation with a composition comprising an alginate lyase, thereby dissolving the purified alginate gel crosslinked with a divalent cation.

2. The method of claim 1, wherein the purified alginate gel is present in the vasculature of a subject having a condition selected from the group consisting of: arteriovenous malformation, vascular occlusion, endovascular repair failure, neurovascular lesions, telangiectasias, varicoceles, varicose veins, inflammatory lesions, hemorrhage, occlusion, embolism, neoplastic growth, venous disease, and phlebitis.

3. The method of claim 2, wherein the endovascular repair failure is endoleakage.

4. The method of claim 2, wherein the vascular occlusion is an embolism.

5. The method of claim 2, wherein the vascular occlusion is a pulmonary embolism or an arterial embolism.

6. The method of claim 1, wherein the purified alginate gel is present in a targeted area of osteoporotic bone.

7. The method of claim 6, wherein the purified alginate gel further comprises an osteogenic agent.

8. The method of claim 6, wherein the osteogenic agent is expressed by a cell.

9. The method of claim 1, wherein the purified alginate gel further comprises a therapeutic agent, or imaging agent.

10. The method of claim 9, wherein the agent is one or more anti-cancer agents.

11. The method of claim 9, wherein the agent is one or more imaging agents.

12. The method of claim 1, wherein the alginate comprises D mannuronic acid and D guluronic acid.

13. The method of claim 1, wherein the alginate comprises an alginic acid.

14. The method of claim 1, wherein the alginate is a commercially available alginate.

15. The method of claim 1, wherein the alginate lyase is a bacterial alginate lyase.

16. The method of claim 15, wherein the bacterial alginate lyase is obtained from a bacteria selected from the group consisting of: *Flavobacterium, Burkholderia, Corynebacterium, Klebsiella, Photobacterium, Pseudoalteromonas, Pseudomonas, Rhodopirellula, Saccharophagus, Sphingomonas, Streptomyces, Vibrio*, and *Aspergillus*.

17. The method of claim 1, wherein the purified alginate gel crosslinked with a divalent cation dissolves within a minute of contacting the purified alginate gel crosslinked with a divalent cation with the composition comprising an alginate lyase.

18. A method for dissolving a purified alginate gel crosslinked with a divalent cation in a subject, the method comprising:
   contacting in the subject the purified alginate gel crosslinked with a divalent cation with a composition comprising an alginate lyase and a divalent metal chelator, thereby dissolving the purified alignate gel crosslinked with a divalent cation.

19. The method of claim 18, wherein the divalent metal chelator is EDTA.

* * * * *